United States Patent [19]
Zimmermann et al.

[11] Patent Number: 5,525,480
[45] Date of Patent: Jun. 11, 1996

[54] N- AND O- SUBSTITUTED AMINOPHENOLS, METHOD AND USE FOR DIAGNOSIS

[75] Inventors: Gerd Zimmermann, Mannheim; Dieter Mangold, Maxdorf, both of Germany

[73] Assignee: Boehringer Mannheim GmbH, Mannheim, Germany

[21] Appl. No.: 257,688

[22] Filed: Jun. 9, 1994

Related U.S. Application Data

[62] Division of Ser. No. 633,231, Dec. 21, 1990, Pat. No. 5,334,505.

[30] Foreign Application Priority Data

Dec. 21, 1989 [DE] Germany ............... 39 42 355.7

[51] Int. Cl.$^6$ .................. C12Q 1/34; C12Q 1/00; A01N 61/00; C07H 1/00
[52] U.S. Cl. ............... 435/18; 435/4; 435/14; 514/1; 514/32; 514/33; 514/25; 514/42; 514/129; 514/130; 514/131; 514/133; 536/1.11; 536/4.1; 536/6; 536/6.1; 536/6.2; 536/22.1; 536/29.1
[58] Field of Search ............... 435/18, 23, 810, 435/4, 7.9, 18, 14; 536/120, 118, 17.3, 1.11, 4.1, 6, 6.1, 6.2, 22.1, 29.1; 514/1, 32, 33, 25, 42, 129, 130, 131, 133

[56] References Cited

U.S. PATENT DOCUMENTS

| | | | |
|---|---|---|---|
| 3,875,013 | 4/1975 | Manautou et al. | 435/18 |
| 4,469,789 | 9/1984 | Berger et al. | 435/23 |
| 4,552,841 | 11/1985 | Ogawa et al. | 435/18 |
| 4,716,222 | 12/1987 | Wallenfels et al. | 536/120 |
| 5,030,721 | 7/1991 | Kasai et al. | 536/17.3 |
| 5,126,329 | 6/1992 | Tani et al. | 536/118 |

FOREIGN PATENT DOCUMENTS

| | | |
|---|---|---|
| 0034323 | 8/1981 | European Pat. Off. |
| 0268167 | 5/1988 | European Pat. Off. |
| 0433853 | 6/1991 | European Pat. Off. |
| 1448348 | 6/1966 | France. |
| 8902473 | 3/1989 | WIPO. |

*Primary Examiner*—Douglas W. Robinson
*Assistant Examiner*—Louise N. Leary
*Attorney, Agent, or Firm*—Felfe & Lynch

[57] ABSTRACT

The present invention provides N- and O-substituted aminophenol derivatives of the general formula

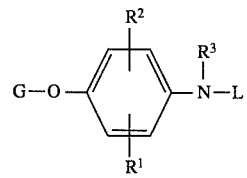

wherein $R^1$, $R^2$, $R^3$, G and L are as hereinbefore defined.

The present invention also provides intermediates for the preparation of these aminophenol derivatives of general formula (I), as well as the use of the aminophenol derivatives of general formula (I) for the determination of hydrolases, as well as for the preparation of agents for carrying out determinations of hydrolysis.

31 Claims, 6 Drawing Sheets

N- AND O- SUBSTITUTED AMINOPHENOLS, METHOD AND USE FOR DIAGNOSIS

This is a divisional application of application Ser. No. 07/633,231, filed Dec. 21, 1990, now U.S. Pat. No. 5,334, 505.

The present invention is concerned with new N- and O-substituted aminophenol derivatives and with a process for the preparation thereof.

The present invention is also concerned with intermediates for the preparation of the N- and O-substituted aminophenol derivatives according to the present invention, as well as with processes for the preparation thereof.

Furthermore, the present invention is concerned with the use of N- and O-substituted aminophenol derivatives as hydrolase substrates.

In addition, the present invention is concerned with a process for the colorimetric determination of a hydrolase by reaction of a chromogenic enzyme substrate with an enzyme, oxidation of a leuko coloured material liberated by the enzyme from the substrate and determination of the resulting colour material as a measure of the amount of the enzyme.

The present invention is also concerned with a diagnostic agent for the determination of a hydrolase, containing a chromogenic enzyme substrate and an appropriate buffer substance.

Finally, the present invention is concerned with the use of an N- or O-substituted aminophenol derivative for the preparation of a diagnostic agent for the determination of a hydrolase.

By hydrolases are, in general, understood enzymes which hydrolytically cleave bonds with the consumption of water. In recent years, in clinical chemistry and in diagnosis, the determination of the activity of such hydrolases has achieved importance which cleave glycosidic and ether bonds. Furthermore, to be here mentioned by way of example are esterases, for example the enzymes cleaving carboxylic esters occurring in leukocytes or phosphates, for example alkaline and acidic phosphates, which hydrolyse phosphoric acid esters. For the diagnosis of diseases of the kidneys and of the urogenital tract, it has proved to be useful to detect leukocytes in urine on the basis of their inherent esterolytic activity. The activity determination of acidic phosphatase is a valuable means for the early diagnosis of prostatic carcinoma. Alkaline phosphatase can be used as a labelling enzyme for enzyme immunoassays.

Glycosidases, for example galactosidases, glucosidases, mannosidases, amylase and N-acetyl-β-D-glucosaminidase cleave glycosidic bonds. In the human and animal organism, they fulfill a plurality of physiological functions. Thus, for example, β-D-galactosidase plays an important part in the metabolism of carbohydrates since, due to it, the hydrolysis of lactose takes place. Furthermore, β-D-galactosidase is the key enzyme in the case of the breakdown of glycolipids, mucopolysaccharides and glycoproteins. As further physiologically important glycosidases, there may be mentioned α-D-galactosidase, α-D- and β-D-glucosidase and also a α-D-mannosidase.

Over and above their physiological value, in recent years, the glycosidases have achieved importance in the diagnostic as well as in the biotechnological fields. Thus, for example, these enzymes are used to an increasing extent as indicator enzymes for enzyme immunoassays. In this connection, β-D-galactosidase is especially preferred.

The presence of the enzyme N-acetyl-β-D-glucosaminidase (β-NAGase) in body fluids is a valuable indicator for diseases or impaired functions in the organism. In the urine, for example, increased values in the case of kidney transplants are an indication of the rejection of the donor kidney. Increased values also occur in the case of a number of diseases and of toxic damage of the kidneys. In the saliva of females, the NAGase activity is an indicator of fertility and pregnancy.

For the determination of the activity of hydrolases, the enzyme-containing sample is reacted with an appropriate substrate. The substrate is cleaved by the enzyme and one of the cleavage products is detected in an appropriate manner. The natural substrates of the enzyme to be detected are often suitable as substrates. However, especially preferred are chromogenic compounds in which one of the cleavage products is a residue which can be detected in the spectroscopically visible or in the ultra-violet region.

As chromogenic substrates for the determination enzymes cleaving ester and glycosidic bonds, in published European Patent Specification No. A-0,274,700 U.S. Pat. No. 4,900,822 there are described dihydroresorufin compounds. After enzymatic cleavage of the substrates, readily water-soluble leuko coloured materials arise which can be oxidised easily by oxidation agents to give coloured materials. Disubstituted dihydroresorufin derivatives are hydrolysed in a multi-step reaction sequence which can give rise to complications in the case of kinetic measurements.

A large number of chromogenic substrates are known for the determination of glycoside bond-cleaving enzymes. Thus, in Biochem. Z., 333, 209/1960, there are described phenyl-β-D-galactoside, as well as some further derivatives substituted on the aromatic ring (for example o-nitrophenyl- and p-nitrophenyl-β-D-galactosides) as substrates for β-D-galactosidase. The phenols liberated by hydrolysis are determined photometrically in the ultraviolet range or, in the case of nitrophenols, in the shortwave visible wavelength range. An oxidative coupling with aminoantipyrine can also follow as indicator reaction (see Analytical Biochem., 40, 281/1971).

For histochemical investigations, naphthyl-β-D-galactosides are used, for example l-naphthyl compounds in Histochemie, 35, 199/1973, the 6-bromo-2-naphthyl derivative in J. Biol. Chem., 195, 239/1952 and naphthyl-β-D-galactoside in Histochemie, 37, 89/1973. For visualisation, the naphthols thereby formed are reacted with various diazonium salts to give azo coloured materials. In the case of such necessary coupling reactions, sample components can, for example, have a disturbing effect when they react with the substances liberated by the enzymatic cleavage instead of the coupling components.

For the detection of the enzyme N-acetyl-β-D-glucosaminidase (NAGase), it is suggested in U.S. patent specification No. 3,968,011 to use those phenol derivatives which are cleaved at the pH values necessary for the enzyme reaction and the reaction products of which form a colour or can be detected or measured at a basic pH value. Therefore, a rebuffering is necessary.

In the same way, in published European Patent Specification No. 0,097,506, NAGase substrates are suggested which, at an acidic pH value, liberate, in the presence of the enzyme, a chromogen, for example p-hiterophenol, which, after rebuffering to a basic pH value, forms a colour which can be measured. In the case of the liberation of umbelliferone, this can be detected fluorimetrically which is, however, very expensive for apparatus and, especially in the case of biological samples, is also subject to disturbances because of the fluorescent background present therein.

In published European Patent Specification No. 0,060, 793 U.S. Pat. No. 4,433,139, sulphophthaleinyl-N-acetyl-β-D-glucosaminides are described as substrates for NAGase. However, the necessity of the measurement of a blank value and the additional handling step which is necessary in order to rebuffer the reaction mixture is disadvantageous.

Published European Patent Specification No. 0,180,961 U.S. Pat. No. 4,754,025 discloses, as β-NAGase substrates, N-acetyl-β-D-glucosaminides substituted in the 2- and 4-positions by halogen or nitro. The process for the determination of NAGase by means of these substrates can admittedly be carried out without additional handling steps and without blank value measurements but the solubility of the substrate is very low even in the presence of wetting agents. In the case of the measurement of NAGase in urine, this results in disturbances due to urine components and, in the case of low enzyme concentrations, the time required for carrying out the test is very great.

Sodium 3,3'-dichlorophenolsulphonphthaleinyl-N-acetyl-β-D-glucosamidine is described in published European Patent Specification No. 0,294,804. Here, too measurements can be carried out directly and without stopping but the detection reaction must be carried out at pH 6.25 since only from there but not at the acidic pH value is the liberated chromogen sufficiently coloured. Since the enzyme in the reaction rate at pH 4.5 to 5 shows a maximum, this results in a retarded enzymatic cleavage of the substrate. In addition, for all previously described analysis processes for the determination NAGase, a spectrophotometric apparatus is necessary.

Substrates which also permit a visual assessment, either directly or after alkali treatment, are described in Federal Republic of Germany Patent Specification No. 28 57 145 U.S. Pat. No. 4,318,986. The coupled coloured materials have the general formula HX—A—Y—NO₂, wherein A is an aromatic nucleus, HX is an auxochromic group and Y is an unsaturated radical. These substrates liberate compounds which indicate the enzyme by a red or blue coloration. However, the process has the disadvantage that, in the presence of the enzyme, only a colour change takes place since the substrates themselves are coloured. In the case of non-pretreated or diluted samples, for example urine, the substrates must be present in high concentrations since otherwise components of the urine drastically slow down the enzymatic cleavage. Even substrates with a weak inherent colour give strongly coloured test strips in the case of the necessary concentrations. A detection via a colour change makes low enzyme concentrations non-detectable or only detectable after a very long period of time.

In published Japanese Patent Specification No. A-64 068389, N- and O-substituted aminophenyl derivatives are suggested as NAGase substrates which, as N-substituents, carry a phenol or naphthol radical with free hydroxyl groups or a quinonimine structure. As a condition, it is stated that one of the two N-substituents present in the molecule can exclusively carry electron-attracting radicals, whereas the other one is substituted by electron donors. These compounds have a very low water solubility. Consequently, they are very subject to disturbance due to sample components. For example, the described compounds are not cleaved by HAGase in urine.

Summarising, the disadvantages of the hydrolase substrates known from the prior art can be stated as follows: Substrates which permit a multiple enzymatic cleavage complicate the kinetic measurement. A light absorption of the radical split off by the enzyme to be determined in the short-wave visible wavelength range (for example yellow-coloured radicals) is, in many samples and especially those of body fluids where many substances are present which also absorb in the short-waved wavelength range, not to be determined free from disturbances. The making visible of a radical which can be split off enzymatically by coupling with a further compound can also be disturbed by sample components. Fluorimetric determinations are expensive for apparatus and, especially in the case of biological samples, are often disturbed by a background fluorescence of the sample material. With hydrolase substrates which, in the case of enzymatic cleavage, merely change their colour or pass through a colour change, determinations of enzymes of low concentration are often only possible with high substrate concentrations, for their reaction much time is required and, under certain circumstances, they can inhibit the enzyme to be determined. Sparing solubility of the hydrolase substrate often leads to a very low sensitivity of the method of determination and increases the time required until the desired result is obtained. Determination processes with hydrolase substrates also require the additional steps such as blank value measurement or rebuffering of the reaction mixture, which requires relatively too much time and, in addition, the carrying out thereof is laborious and, in some cases, complicated so that only experts but not lay persons can carry them out satisfactorily and reproducably. Furthermore, determination methods which require additional handling steps cannot be applied to or can only be applied with difficulty to test carriers, i.e. so-called dry chemical tests, and be carried out with such. Furthermore, determination processes which require, for example, a rebuffering step, do not permit kinetic determinations but rather are purely end-point methods.

The present invention is here helpful. The present invention, as it is hereinafter described and claimed, solves the problems of making available hydrolase substrates which make the determination of hydrolases quick and simple, which permit not only kinetic measurement but also end point determinations, which are also capable of sensitively determining low enzyme concentrations, which can serve for a hydrolase determination which is as free as possible of disturbances, which do not make any expensive apparatus necessary and which an also be used on test carriers.

Thus, the present invention is concerned with the use of N- and O-substituted aminophenol derivatives of the general formula:

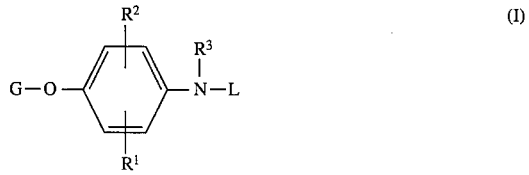

(I)

wherein G is an organic or inorganic acid residue or a glyciside radical, $R^1$ and $R^2$, which are the same or different, are hydrogen or halogen atoms, $SO_3H$, $PO_3H_2$ or a salt of these acid groups, hydroxyl, nitro, carboxyl, carboxamido or cyano or an alkyl, alkenyl, alkoxy, alkylsulphinyl, alkylsulphonyl, alkoxycarbonyl, alkylcarbonyl, aryl or aralkyl radical optionally substituted one or more times by hydroxyl, carboxyl, halogen, cyano, $SO_3H$ or $PO_3H_2$ residues or a salt of these acid residues or, when two substituents are present on neighbouring carbon atoms, these can together present a 1,4-butadiendiyl radical which is optionally substituted one or more times by $SO_3H$, $PO_3H_2$ or a salt of these acid residues, an alkyl and/or a carboxyl group, $R^3$ is a hydrogen atom, CO—COOH, $SO_3H$, $PO_3H_2$ or a salt of these acid residues, an alkylcarbonyl radical optionally substituted one or more times by halogen, COOH, SO₃H and/or PO₃H₂ or a salt of these acid groups or an arylcarbonyl radical optionally substituted one or more times by SO₃H, PO₃H₂ or a salt of these acid residues and L is a radical of the general formula:

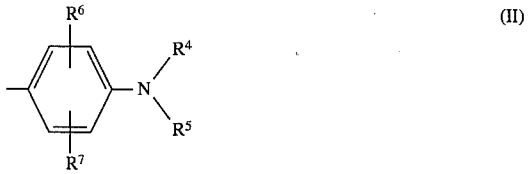

wherein $R^4$ and $R^5$, which can be the same or different, are alkyl radicals or together represent a saturated hydrocarbon chain containing 3 to 6 members which can be interrupted by oxygen, sulphur or nitrogen, whereby alkyl or the hydrocarbon chain is optionally substituted one or more times by hydroxyl, carboxyl, alkoxycarbonyl, alkoxy, SO₃H or PO₃H₂ groups, a salt of these acid residues or halogen and $R^6$ and $R^7$, which can be the same or different, are hydrogen or halogen atoms, hydroxyl, carboxamido or an alkyl, alkoxy, alkylcarbonyl, alkoxycarbonyl, aryl or aralkyl radical optionally substituted one or more times by hydroxyl, carboxyl, halogen, SO₃H or PO₃H₂ or a salt of these acid residues or L is a pyrazolo-heterocyclic radical of the general formula:

in which X-Y is NR⁸—CO or N=CR⁹, in which $R^8$ is an hydrogen atom, or an alkyl radical and $R^9$ is alkyl, alkenyl, alkoxy, alkylthio, aryl, aralkyl, in each case optionally substituted by hydroxyl, dialkylphosphinyl, carboxyl, SO₃H, PO₃H₂, a salt of these acid residues and/or alkoxycarbonyl; amino, which is optionally substituted by one or two alkyl radicals which, in turn, are optionally substituted one or more times by hydroxyl, carboxyl and/or alkoxycarbonyl, and when amino is substituted by two alkyl radicals, these can be joined to form a ring which, apart from the nitrogen atom of the amino group, can optionally also be interrupted by oxygen, sulphur or a further nitrogen atom or amino can optionally be substituted by one or two acyl radicals, alkoxy- and/or aralkoxycarbonyl radicals, H₂N—CO, alkyl-, aralkyl- and/or arylcarbamoyl radicals; or is hydrogen, carboxyl, alkoxycarbonyl, carboxamido or halogen and Z is NR¹⁰—N=N, in which $R^{10}$ is a hydrogen atom or an alkyl or aralkyl radical or Z is an unsaturated chain containing 3 to 5 members of nitrogen atoms or of carbon atoms and optionally one or more nitrogen or sulphur atoms, whereby carbon atoms are optionally substituted by alkyl, alkoxy, hydroxyalkyl, alkylthio, hydroxyl, aralkyl, aryl, carboxyl, carboxamido, alkoxycarbonyl, cyano, amino, which is optionally substituted by one or two alkyl radicals which, in turn, are optionally substituted by one or more hydroxyl, carboxyl and/or alkoxycarbonyl radicals, and/or halogen, as well as nitrogen atoms which are not connected via a double bond are optionally substituted by alkyl or aralkyl or two neighbouring chain substituents optionally form an alkylene radical which, in turn, is optionally substituted or anellated with aryl, and the corresponding tautomeric radicals thereof, as hydrolase substrates.

From published British Patent Specification No. 2,061, 537 and from published Federal Republic of Germany Patent Specification No. 22 60 202 U.S. Pat. No. 3,952,009 are known pyrazolotriazole derivatives as coloured material formers for the production of photographic pictures which correspond to general formula (I) when there G is an alkanecarboxylic acid radical, $R^3$ is a hydrogen atom, an arylcarbonyl radical or an alkylcarbonyl radical optionally substituted one or more times by halogen and L is a pyrazoloheterocyclic radical of general formula (III) in which X-Y is n=CR⁹, $R^9$ has the above-given meaning, and in addition Z is a 1,2,4-triazole ring in which a nitrogen atom not connected via a double bond is substituted by a hydrogen atom. The other compounds of general formula (I) are new.

Thus, the present invention also provides N- and O-substituted aminophenol derivatives of the general formula:

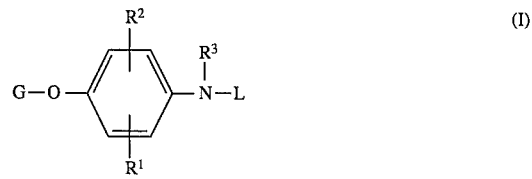

in which G is the residue of an organic or inorganic residue or a glycoside radical, $R^1$ and $R^2$, which can be the same or different, are hydrogen, halogen, SO₃H, PO₃H₂ or a salt of these acid groups, a hydroxyl, nitro, carboxyl, carboxamido or cyano group or an alkyl, alkenyl, alkoxy, alkylsulphinyl, alkylsulphonyl, alkoxycarbonyl, alkylcabonyl, aryl or aralkyl radical optionally substituted one or more times by hydroxyl, carboxyl, halogen, cyano, SO₃H or PO₃H₂ or a salt of one of these acid residues or, when both substitutents are present on neighbouring carbon atoms, together represent a 1,4-butadiendiyl radical which is optionally substituted one or more times by SO₃H, PO₃H₂ or a salt of these acid residues, $R^3$ is hydrogen, CO—COOH, SO₃H, PO₃H₂ or a salt of these acid residues, an alkylcarbonyl radical optionally substituted one or more times by halogen, COOH, SO₃H and/or PO₃H₂ or a salt of these acid residues or an arylcarbonyl radical optionally substituted one or more times by SO₃H, PO₃H₂ or a salt of these acid residues and L is a radical of the general formula:

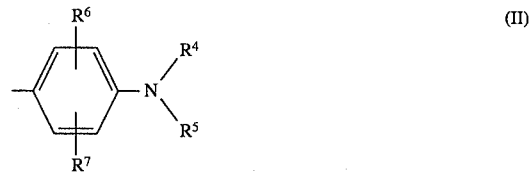

in which $R^4$ and $R^5$, which can be the same or different, are alkyl radicals or together represent a saturated hydrocarbon chain containing 3 to 6 members which can be interrupted by oxygen, sulphur or nitrogen, whereby alkyl or the hydrocarbon chain is optionally substituted one or more times by hydroxyl, carboxyl, alkoxycarbonyl, alkoxy, SO₃H or PO₃H₂ groups, a salt of these acid residues or halogen and $R^6$ and $R^7$, which can be the same or different, are hydrogen halogen, hydroxyl or carboxamido or an alkyl, alkoxy, alkylcarbonyl, alkoxycarbonyl, aryl or aralkyl radical optionally substituted one or more times by hydroxyl, carboxyl, halogen, SO₃H or PO₃H₂ or a salt of one of these acid residues or L is a pyrazolo-heterocyclic radical of the general formula:

in which X-Y is NR⁸—CO or N=CR⁹, whereby $R^8$ is a hydrogen atom or an alkyl radical and $R^9$ is alkyl, alkenyl, alkoxy, alkylthio, aryl aralkyl, optionally in each case substituted by hydroxyl, dialkylphosphinyl, carboxyl, $SO_3H$, $PO_3H_2$, a salt of one of acid residues and/or alkoxycarbonyl; amino, which is optionally substituted by one or two alkyl radicals which, in turn, are optionally substituted one or more times by hydroxyl, carboxyl and/or alkoxycarbonyl, whereby, when amino is substituted by two alkyl radicals, these residues can also be joined to form a ring which, apart from the nitrogen atom of the amino group, can optionally also be interrupted by oxygen, sulphur or a further nitrogen atom or amino is optionally substituted by one or two acyl radicals, alkoxy- and/or aralkoxycarbonyl radicals, $H_2N$—CO, alkyl-, aralkyl- and/or arylcarbamoyl radicals; or is hydrogen, carboxyl, alkoxycarbonyl, carboxamido or halogen, and Z is $NR^{10}$—N=N, whereby $R^{10}$ is hydrogen, alkyl or aralkyl or Z is an unsaturated chain containing 3 to 5 members of nitrogen atoms or of carbon atoms and optionally one or more nitrogen or sulphur atoms, whereby carbon atoms are optionally substituted by alkyl, alkoxy, hydroxyalkyl, alkylthio, hydroxyl, aralkyl, aryl, carboxyl, carboxamido, alkoxycarbonyl, cyano, amino, which is optionally substituted by one or two alkyl radicals which, in turn, are optionally substituted one or more times by hydroxyl, carboxyl and/or alkoxycarbonyl, and/or halogen, as well as nitrogen atoms which are not connected via a double bond are optionally substituted by alkyl or aralkyl or two neighbouring chain substituents optionally form an alkylene radical which, in turn, is optionally substituted or annellated with aryl, and the corresponding tautomeric radicals, with the proviso that when G is an alkanecarboxylic acid radical, $R^3$ is a hydrogen atom, an arylcarbonyl radical or an alkylcarbonyl radical optionally substituted one or more times by halogen and L is a pyrazolo-heterocyclic radical of general formula (III) in which X-Y is $N=CR^9$, whereby $R^9$ has the same meanings as above, Z does not form a 1,2,4-triazole ring in which a nitrogen atom not connected via a double bond is substituted with hydrogen.

The present invention also provides a process for the preparation of these compounds, wherein a compound of the general formula:

in which G is the residue of an organic or inorganic acid or a glycoside radical and D is a reactive group, whereby functional groups in G are optionally protected with protective groups such as are conventional in peptide and carbohydrate chemistry, is reacted with a compound of the general formula:

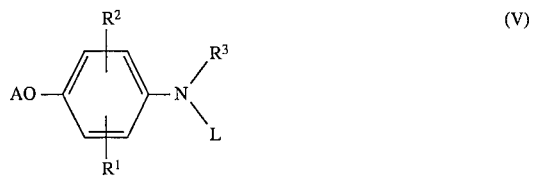

in which $R^1$–$R^3$ and L have the meanings given in general formula (I) and $R^3$ can additionally be an amino protective group and A is a hydrogen atom, an optionally substituted ammonium ion or an alkali metal, and protective groups are optionally subsequently split off.

Furthermore, the present invention provides compounds of the general formula V'

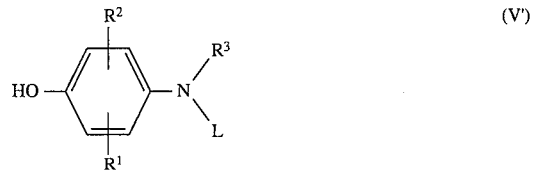

wherein $R^1$–$R^3$ have the meanings given in general formula I and L is a pyrazolo-heterocyclic radical of the general formula:

in which X-Y and Z have the meanings given in general formula (I) with the proviso that when $R^3$ is an aryl-carbonyl radical or an alkylcarbonyl radical optionally substituted one or more times by halogen and X-Y is C=$NR^9$, Z does not form a 1,2,4-triazole ring in which a nitrogen atom not connected via a double bond is substituted by hydrogen.

In addition, the present invention provides a process for the preparation of compounds of general formula (V'), wherein
a) a compound of the general formula:

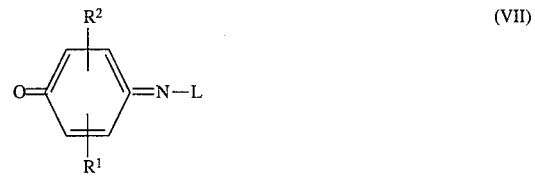

in which $R^1$, $R^2$ and L have the meanings given in general formula (V'), is reduced and, when $R^3$ is not to be a hydrogen atom, the anilino group is acylated and an ester group optionally present is split off; or
b) a compound of general formula (I), in which L is a pyrazolo-heterocyclic radical of the general formula:

in which X-Y, G and Z have the meanings given in general formula (I), is reacted with an appropriate hydrolase.

The present invention also provides compounds of the general formula:

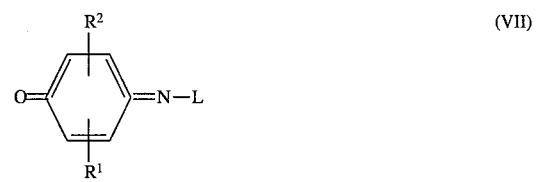

in which $R^1$ and $R^2$ have the meanings given in general formula (I) and L is a pyrazolo-heterocyclic radical of the general formula:

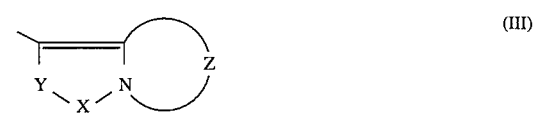

in which X-Y and Z have the meanings given in general formula (I).

Furthermore, the present invention provides a process for the preparation of compounds of general formula (VII), wherein
a) a compound of general formula (I), in which L is a pyrazol-heterocyclic radical of the general formula:

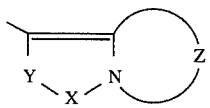 (III)

in which X-Y and Z have the meanings given in general formula (I), is reacted with a hydrolase and the reaction product is oxidised or
b) a compound of the general formula:

 NH₂—L (VIII)

in which L is a pyrazolo-heterocyclic radical of the general formula:

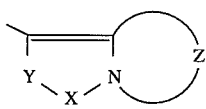 (III)

in which X-Y and Z have the meanings given in general formula (I) is reacted with a phenol of the general formula:

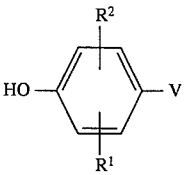 (IX)

in which $R^1$ and $R^2$ have the meanings given in general formula (VII) and V is a hydrogen or halogen atom or a COOH or SO₃H group, in the presence of an oxidation agent, or
c) a compound of the general formula:

L—H (X)

in which L is a pyrazolo-heterocyclic radical of the general formula:

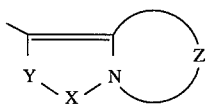 (III)

in which X-Y and Z have the meanings given in general formula (I), is reacted with a compound of the general formula:

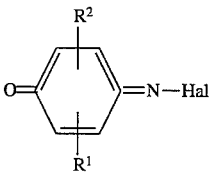 (XI)

in which $R^1$ and $R^2$ have the meanings given in general formula (VII) and Hal is a halogen atom, or
d) a compound of the general formula:

L—E (XXV)

in which E is a nitro or nitroso group and L is a pyrazolo-heterocyclic radical of the general formula:

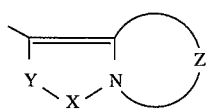 (III)

in which X-Y and Z have the meanings given in general formula (I), is reacted with an organo-metallic compound of the general formula:

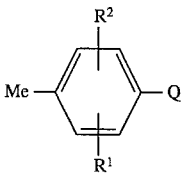 (XXVI)

in which $R^1$ and $R^2$ have the meanings given in general formula (VII), Q is a hydroxyl group or a dialkylamino radical and Me is lithium or magnesium substituted by a halogen atom, and subsequently worked up in an aqueous medium.

The subject of the present invention is also the use of compounds of general formulae (V') and (VII) for the preparation of new compounds of general formula (I).

The subject of the present invention is also a process for the colorimetric determination of a hydrolase by reaction of a chromogenic enzyme substrate with the enzyme, oxidation of a leuko coloured material liberated from the substrate by the enzyme and determination of the resultant coloured material as a measure of the amount of enzyme, wherein, as enzyme substrate, there is used a compound of general formula (I).

In addition, a subject of the present invention is a diagnostic agent for the determination of a hydrolase, containing a chromogenic enzyme substrate and an appropriate buffer substance, wherein, as chromogenic enzyme substrate, there is used a compound of general formula (I).

Finally, a subject of the present invention is the use of a compound of general formula (I) for the production of a diagnostic agent for the determination of a hydrolase.

DESCRIPTION

Figure 1:
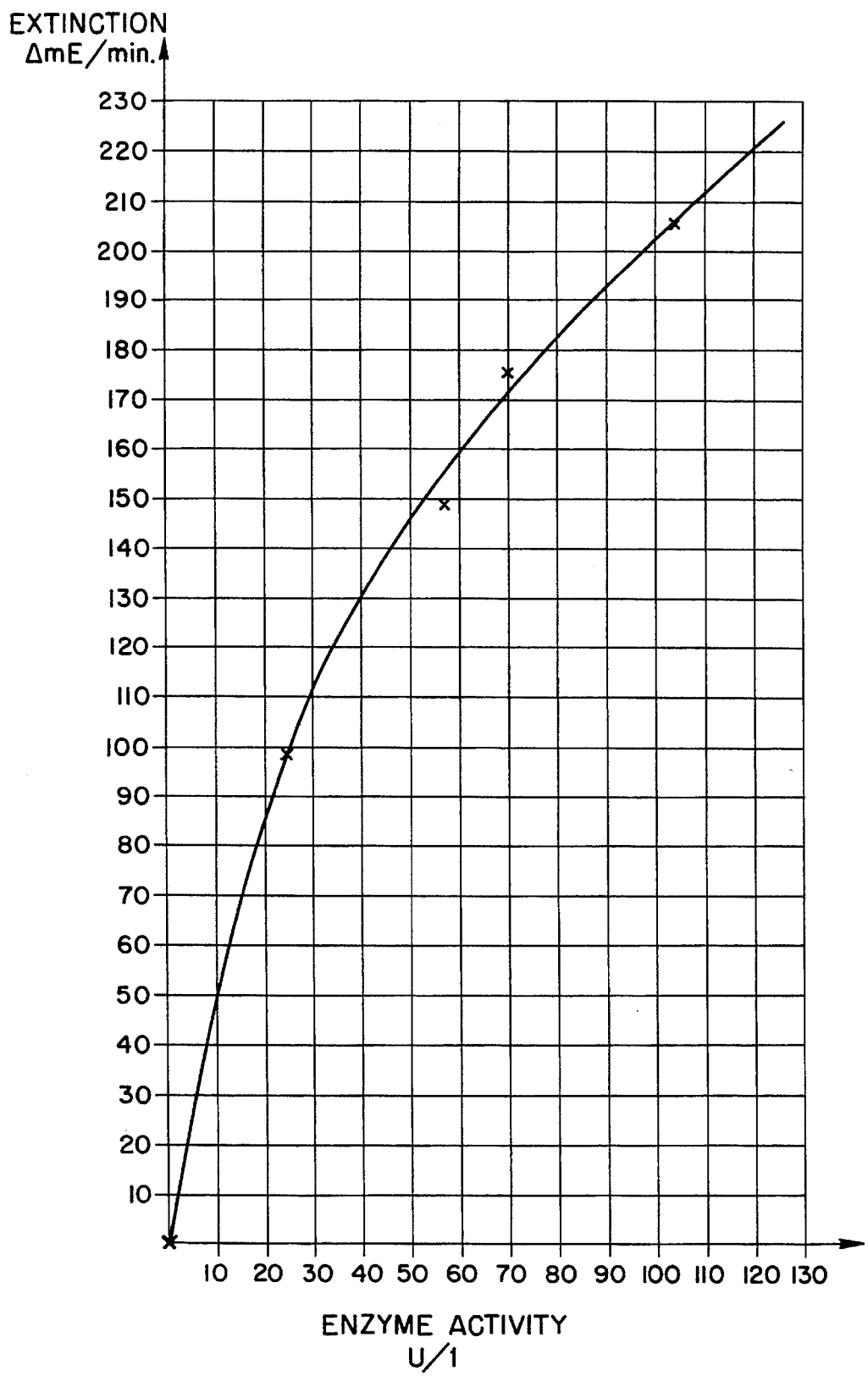
FIG. 1 shows a calibration curve at λmax 560 nm for the substrate from example 4e.

We have found that compounds of general formula (I) with the above-given meaning are hydrolase substrates which solve the defined problems in an outstandingly good manner.

By an inorganic acid residue in the definition of G, there is to be understood, in particular, the ortho- and pyrophosphoric acid and sulphuric acid residue which is attached to the aminophenol base structure via an ester bond. Preferred are the residues PO₃MM' and SO₃M and especially PO₃MM', whereby, in the case of the free acids, M and M' are hydrogen atoms, whereas, when the acids are present as salts, M and M' stand for alkali metal, alkaline earth metal or ammonium ions.

By alkali metal ions in the definitions of M and M', there are to be understood, in particular, lithium, sodium and potassium ions. Alkaline earth metal ions are, in particular, magnesium, calcium or barium ions.

Ammonium ions in the definitions of M and M' can be the unsubstituted ammonium ion $NH_4^+$ or ammonium ions substituted one or more times by alkyl or aralkyl radicals. The alkyl radical is hereby to be understood to be one containing up to 6 carbon atoms, the methyl or ethyl radical being preferred. By an aralkyl radical is to be understood one in which the above-defined alkyl radical is substituted by an aryl radical, whereby aryl is a carbon aromatic or hetero-aromatic radical and preferably one containing 6 to 10 ring atoms, especially a phenyl or naphthyl radical. The preferred aralkyl radical is a benzyl radical. The substituents of substituted ammonium ions can be the same or different. As ammonium ions there can also be used cations of quaternised nitrogen heterocyclic compounds, examples therefor including a piperidinium cation and the pyridinium ion.

By an organic acid residue in the definition of G are to be understood, in particular, the residues of alkanecarboxylic acids, amino acids, and oligopeptides which, with the carboxyl end thereof, are present bound to the aminophenol base structure of general formula (I) as esters.

Alkanecarboxylic acid residues in the definition of G are compounds containing up to 20 carbon atoms. Especially preferred are acetic acid, propionic acid, butyric acid, palmitic acid and stearic acid. Besides saturated acid residues, G can also be an unsaturated acid residue, for example of oleic acid, linoleic acid or linolenic acid.

An amino acid residue is preferably the residue of a naturally-occurring α-amino acid in its L₋ or D-form or also in the racemic form thereof. Especially preferred are the residues of glycine, alanine, valine, leucine, isoleucine, phenylalanine and tyrosine, in which, in each case, the L-form is quite especially preferred.

By an oligopeptide residue is to be understood, for example, a di-, tri-, tetra- or pentapeptide and preferably a di- or tripeptide, whereby the amino acid components are preferably the above-mentioned amino acids.

The amino groups of the amino acids and oligopeptide residues, bound in the manner of an ester to the aminophenol radical, can be present in free or protected form. As protective groups, there are here to be understood all the conventional amino protective groups, especially acyl, oxycarbonyl, thiocarbonyl, sulpho, sulphino, vinyl, cyclohexenyl, phosphoryl and carbamoyl groups. Especially preferred amino protective groups include the tosyl, benzyloxycarbonyl and tert.-butoxycarbonyl radicals.

A glycoside radical in the definition of G can be a mono- or oligosaccharide. The sugar residue can be bound to the aminophenol base structure α- or β-glycosidically. Examples of preferred monosaccharides include galactose, glucose and mannose. N₋acetylglucosamine is especially preferred. Quite especially preferred is β-glycosidically bound N-acetyl-2-D-glucosamine.

However, oligosaccharides have also proved to be suitable as sugar residues. As oligosaccharides are especially designated those which are made up to 2 to 10 and preferably 2 to 7 monosaccharide units. The heptaoses are especially preferred.

From the group of the organic and inorganic acid residues and of the glycoside residues in the meaning of G, the glycoside residues are preferred for compounds of general formula I. The N-acetylglucosamine residue is especially advantageous.

Insofar as nothing is stated to the contrary, the following radicals have the following means in the general formulae used herein: "alkyl", also in alkylsulphinyl, alkylsulphonyl, alkylcarbonyl, alkylthio, alkylcarbamoyl, alkylamino and aralkyl radicals, means a straight-chained or branched alkyl radical containing up to 6 and preferably up to 4 carbon atoms, examples therefor including the methyl, ethyl, propyl, isobutyl and tert.-butyl radicals.

When an amino group is substituted by two alkyl radicals, these radicals can be joined to give a ring which, in all, represents a ring interrupted by a nitrogen atom. Preferred are hereby those amino groups which, in all, represent a five- or six-membered ring and which, in turn, is optionally interrupted by oxygen, sulphur or a further nitrogen atom. The morpholino radical is especially preferred.

A hydroxyalkyl radical is an alkyl radical containing up to 6 and preferably up to 4 carbon atoms substituted by a hydroxyl group. The hydroxyalkyl radical can be the residue of a primary, secondary or tertiary alcohol. Especially preferred are the 2- and 1-hydroxyethyl and the hydroxymethyl radicals.

"Alkoxy", also in alkoxy- and aralkoxycarbon radicals, stands for a straight-chained or branched alkoxy radical containing up to 6 and preferably up to 4 carbon atoms. Examples therefor include the methoxy, ethoxy, propoxy, isobutoxy and tert.-butoxy radicals.

"Aryl", also in arylcarbonyl and arylcarbamoyl radicals, indicates a carbo aromatic or heteroaromatic radical and preferably one with 6 to 10 ring atoms, especially a phenyl or naphthyl radical, which, in addition, can also be substituted by alkyl, alkoxy and/or halogen, the phenyl radical being especially preferred.

An "aralkyl" radical, also in an aralkylcarbamoyl radical, means a radical in which an alkyl radical as defined hereinbefore is substituted by an aryl radical, the benzyl radical being preferred.

An "aralkoxy" radical, for example an aralkoxycarbonyl radical, signifies a radical in which an alkoxy radical as hereinbefore defined is substituted by an aryl radical, the benzyloxy radical being preferred.

"Halogen" stands for a fluorine, chlorine, bromine or iodine atom, fluorine and chloride being preferred.

"Alkenyl" means an unsaturated hydrocarbon radical containing 2 to 6 and preferably 2 to 4 carbon atoms, examples thereof including the vinyl and allyl radicals.

An acyl radical designates a carboxylic acid residue which can contain alkyl, aralkyl or aryl radicals, the acetyl, phenylacetyl and benzoyl radicals being preferred. By an alkylene is to be understood a straight-chained or branched, saturated or unsaturated hydrocarbon radical containing 3 to 5 and preferably 3 or 4 carbon atoms with two free bonding positions. Examples thereof include —CH₂—CH=CH—, $$-CH=C-CH_2-, -CH-CH=CH-,$$
$$\quad\quad | \quad\quad\quad\quad\quad |$$
$$\quad\; CH_3 \quad\quad\quad\; CH_3$$

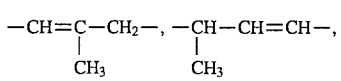—CH=CH—CH=CH—, the butadiendiyl radical (—CH=CH—CH=CH) and the tetramethylene radical (—(CH₂)₄—) being preferred.

By an dialkylphosphinyl group is to be understood the residue

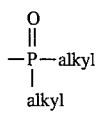

whereby alkyl has the same meanings given above. The dimethylphosphinyl residue is preferred.

As salts of $SO_3H$, $PO_3H_2$ and carboxyl residues, there can be used alkali metal, alkaline earth metal or ammonium salts. By alkali metal salts are to be understood lithium, sodium, potassium, rubibium and caseium salts, whereby lithium, sodium and potassium salts and especially sodium and potassium salts are preferred. Alkaline earth metal salts are those of beryllium, magnesium, calcium, strontium and barium, whereby magnesium and calcium salts and especially calcium salts are preferred. As ammonium salts, there can be used those of the unsubstituted ammonium ion $NH_4^+$. However, it is also possible to use those ammonium salts in which the ammonium ion is substituted by up to 4 alkyl, aryl or aralkyl radicals. For these radicals there apply the above-given definitions, whereby the alkyl radical is preferably the methyl, ethyl or n-propyl radical, the aryl radical is preferably the phenyl radical and the aralkyl radical is preferably the benzyl radical. As ammonium ions there can also be used cations of quaternised nitrogen heterocyclic compounds, examples thereof including the piperidinium cation and the pyridinium ion.

As carboxamido radical, there is to be understood the $CONH_2$ group but also those groups in which the amino group is also substituted by one or two alkyl radicals which optionally are, in turn, substituted by one or more hydroxyl, carboxyl and/or alkoxycarbonyl radicals.

Advantageous are, in particular, those compounds according to the present invention in which $R^3$ is a hydrogen atom or an alkylcarbonyl radical substituted one or more times by halogen, for example trifluoroacetyl. The meaning of hydrogen for $R^3$ is quite especially preferred.

Compounds according to the present invention in which L is a pyrazolo-heterocyclic radical of general formula (III) are preferred. Of these, especially those in which Z is so positioned that at least one double bond of the unsaturated chain is in conjugation with the double bond or with the nitrogen atom in general formula (III).

Furthermore, compounds according to the present invention in which L is a pyrazolo-heterocyclic radical of general formula (III) are especially preferred which, in the unsaturated chain Z, if this contains nitrogen atoms which are not connected via a double bond, are only substituted with alkyl or aralkyl radicals on these nitrogen atoms.

Tautomeric forms are also possible for radical of general formula (III). These are also to be regarded as being covered by general formula (III).

According to the present invention, those compounds of general formula (I) are preferred in which L is a radical of one of the following general formulae (XIII) to (XXIV):

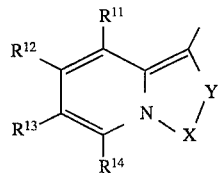

(XIII)

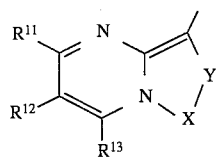

(XIV)

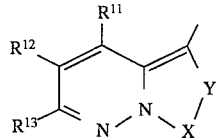

(XV)

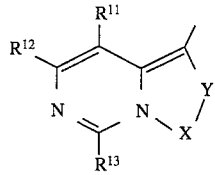

(XVI)

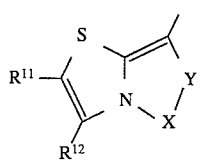

(XVII)

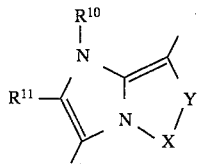

(XVIII)

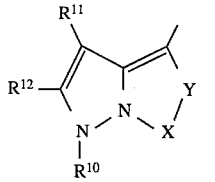

(XIX)

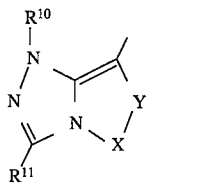

(XX)

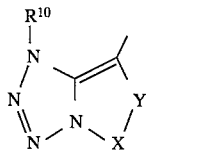

(XXI)

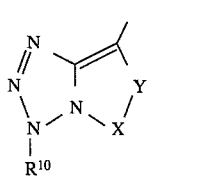

(XXII)

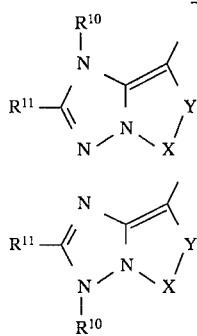

as well as possibly the corresponding tautomeric forms. In the above general formulae, X-Y and $R^{10}$ have the same meanings as hereinbefore. $R^{11}$, $R^{12}$, $R^{13}$ and $R^{14}$, which can be the same or different, stand for hydrogen, hydroxyl, alkyl, alkoxy, alkylthio, aralkyl, aryl, carboxyl, alkoxycarbonyl, carboxamido, cyano, amino, which is optionally substituted once or twice by alkyl radicals which, in turn, are optionally substituted by one or more hydroxyl, carboxyl and/or alkoxycarbonyl groups, or halogen, whereby two neighbouring radicals optionally form an alkylene radical which, in turn, is optionally substituted or anellated with aryl. The definitions of the radicals correspond to those given hereinbefore.

According to the present invention, compounds of general formula (I) are especially preferred in which L is a radical of the groups of general formulae (XIII), (XIV), (XV), (XVII), (XVIII) and (XX) and optionally also the corresponding tautomeric forms thereof. Quite especially preferred are those compounds in which X-Y is $N=CR^9$, wherein $R^9$ can have the meaning give in general formula (III) but is preferably a hydrogen atom or an alkoxy radical.

Outstandingly preferred in the meaning of the present invention is especially the β-glycosidically-bound N-acetyl-2-D-glucosaminide of 4-hydroxyphenyl-2-methylpyrazolo-(1,5-a)pyridin-3-ylamine.

The compounds of general formula (I) are new. They can be prepared by reacting a leuko methine coloured material of the general formula:

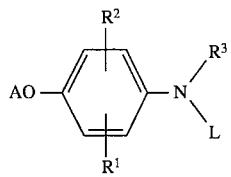

in which $R^1$–$R^3$ and L have the same meanings as given in general formula (I) and A is a hydrogen atom, an optionally substituted ammonium ion or an alkali metal, with a compound of the general formula:

G—D  (IV)

in which G is the residue of an organic or inorganic acid or a glycoside residue having the meanings given in general formula (I), whereby functional groups present in the glycoside residue, for example amino and/or hydroxyl groups, are optionally substituted with protective groups which are conventional in peptide and carbohydrate chemistry, and D is a reactive group, whereafter protective groups are optionally split off.

An unsubstituted ammonium ion is to be understood to be $NH_4^+$. This ion can optionally be substituted one or more times by alkyl or aralkyl radicals with meanings given for A in general formula (V). The substituents of substituted ammonium ions can be the same or different. As ammonium ions, there can also be used quaternised nitrogen-heterocyclic compounds, examples therefor including the piperidinium cation and the pyridinium ion.

As alkali metals in the meaning of A in general formula (V), there can be used lithium, sodium and potassium, sodium being preferred.

D means a reactive group which is able to react with the phenol or phenolate group OA of general formula (V). The choice of the reactive group depends upon the nature of the radical G. If G is a sugar residue, then D is preferably a group which can readily be replaced, for example an acetyl radical or a halogen atom, which can be selected from fluorine, chlorine, bromine and iodine, chlorine, bromine and iodine being preferred.

As protective groups which are conventional in carbohydrate chemistry, there are to be mentioned, in particular, the acetyl, benzoyl, benzyl and trimethylsilyl radicals.

When G is a residue of an amino acid or of a peptide which is to esterified with its carboxyl end with an aminophenol of general formula (V), then, as reactive group D, there can be used all groups which are conventional in peptide chemistry. As reactive derivatives, there can be used, for example, the acid halides, preferably the acid chloride, or the mixed anhydrides or active esters usually employed in peptide syntheses. The same reactive groups can also be used for the binding of alkanecarboxylic acids to the aminophenol structure.

When G is an inorganic acid residue, compounds of general formula (V) are preferably reacted with the corresponding acid halides and especially acid chlorides.

In every case, in the case of the esterification, care is to be taken, when $R^3$ is general formula (V) is a hydrogen atom, to substitute this amino group, before carrying out the esterification reaction, with a protective group, for example a group conventionally used for this purpose in peptide chemistry, whereafter the protective group is again removed.

By way of example, the process for the preparation of compounds of general formula (I) is to be illustrated using the example of the especially preferred compounds in which G is an N-acetyl-β-D-glucosaminide radical. This process can also be used correspondingly for the preparation of other glycoside derivatives of general formula (I).

N-Acetyl-β-D-glucosaminidyl derivatives of general formula (I) according to the present invention can be prepared by reacting a compound of the general formula:

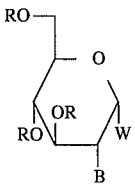

wherein W is a halogen atom, R is a hydroxy protective group conventional in carbohydrate chemistry, B is an azide group, a protected amino group or $NH-COOH_3$ or B and W together signify the group:

with a compound of the general formula:

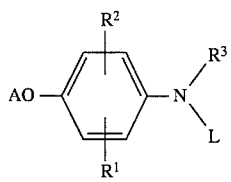

wherein $R^1$–$R^3$ and L have the meanings given for general formula (I) and A is a hydrogen atom, an optionally substituted ammonium ion or an alkali metal, when B is a protected amino group, the amino protective group is removed or when B is an azide group this is converted by reduction into an amino group and the amino group is converted by acetylation into an $NHCOCH_3$ radical and finally the hydroxy protective group is split off.

One possibility is, for example, to react a leuko methine coloured material of the general formula:

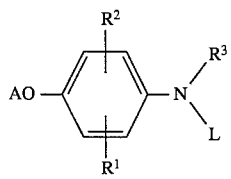

wherein $R^1$–$R^3$ and L have the meanings given for general formula (I), with a per-O-substituted L-halo-N-acetylglucosamine of the general formula:

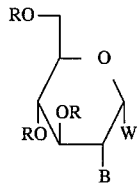

wherein W is a halogen atom, B is $NHCOOH_3$ and A is a protective group which is conventional in carbohydrate chemistry, with Walden inversion on the C-1 atom of the sugar residue, to give a per-O-substituted β-glycoside, whereafter the hydroxy protective groups are split off from the latter according to known methods.

The reaction of compounds of general formulae (V) and (VI) with the above-given meanings to give N-acetyl-β-D-glucosaminides of general formula (I) is preferably carried out in the presence of an acid acceptor, for example an alkali metal hydroxide, carbonate or bicarbonate, in aqueous acetone or under phase transfer conditions in a water/benzene or water/chloroform mixture (cf. Synthesis, 223/1988).

Furthermore, the N-acetyl-β-D-glucosaminides of general formula (I) can be prepared by first converting the leuko coloured materials of general formula (V), in which A is a hydrogen atom, with an alkali metal hydroxide or alcoholate into the corresponding alkali metal salt or with an optionally substituted amine into an ammonium salt, whereby the alkali metal and the ammonium ion can have the above-given meanings, whereafter these are then reacted in a dipolar aprotic solvent, for example acetone, dimethyl sulphoxide, dichloromethane of dimethylformamide, with the per-O-substituted 1-halo-N-acetylglucosamines.

In addition, in the case of the synthesis of N-acetylglucosaminides of general formula (I) from leuko coloured materials of general formula (V) and 1-halo-N-acetylglucosamines, it has proved to be useful to add individual silver salts or mixtures of silver salts (silver oxide, carbonate on Celite®, triflate, salicylate) and/or individual mercury salts or mixtures of mercury salts (mercury bromide, cyanide, acetate, oxide), optionally with the use of a drying agent, for example calcium chloride or Drierit®, in a solvent, for example methylene chloride, chloroform, benzene, toluene or dioxan.

There can also be used an oxazoline of general formula (VI), wherein B and W together signify a group of the formula:

in the presence of an organic acid, for example, p-toluenesulphonic acid, or of a Lewis acid, for example boron trifluoride etherate or ferric chloride, for the synthesis of N-acetylglucosaminides of general formula (I). Examples of such glycosidation reactions are described, for example, in Carbohydrate Research, 136, 309–323/1985 and 64, 334–338/1978.

Finally, processes for the preparation of N-acetylglucosaminides of general formula (I) can be carried out in which the compound of general formula (I), B is an amino group substituted with a protective group, for example a benzyloxycarbonyl, allyloxycarbonyl, dichloroacetamido or phthalimido radical, or a substituent which is stable under the glycosidation conditions from which an amino group can be liberated, for example an azide group. The glycosidation reaction is carried out by splitting off the protective groups according to methods of peptide chemistry or by reduction of the azido group to free the amino group which is then selectively N-acetylated in a final step (see, for example, J. Crg. Chem., 32, 3767/1967).

The splitting off of protective groups takes place is the manner known from carbohydrate chemistry by hydrogenolysis in the case of protective groups of the benzyl type, by the action of sodium methylate, sodium cyanide or sodium bicarbonate in methanol for the splitting off of acyl radicals, for example acetyl radicals. The methods for the splitting off of protective groups are described in Adv. Carbohydr. Chem. Biochem., 39, 13/1981.

The synthesis of 1-halo-N-acetylglucosamines is described, for example, in Org. Synth., Vol. 46, p. 1, Methods in Carbohydrate Chem., 6, 282/1972 and in J. Org. Chem., 26, 445/1961.

The leuko coloured materials required for the preparation of compounds of general formula (I) and which have the general formula:

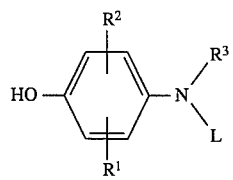

wherein $R^1$–$R^3$ and L have the meanings given for general formula (I), whereby L is preferably a pyrazolo-heterocyclic radical of the general formula:

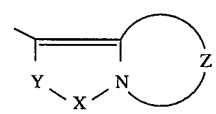

in which X-Y and Z have the meanings given hereinbelow for the corresponding compounds of general formula (I), are, with the exception of those compounds according to published British Patent Specification No. A-2,061,537 in which R³ is an arylcarbonyl radical or an alkylcarbonyl radical optionally substituted one or more times by halogen and in which Z is a 1,2,4-triazole ring, in which a nitrogen atom not connected via a double bond is substituted with hydrogen, are also new.

They can be prepared by reduction of the corresponding coloured materials of the general formula:

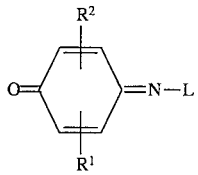
(VII)

wherein R¹, R² and L have the meanings given for compounds of general formula (V'), according to known methods with reducing agents, for example catalytic hydrogenation, sodium borohydride, palladium/hydrazine or sodium dithionite. Such reducing agents are described in Houben-Weyl, Vol. 4/1C and 4/1d.

Acyl radicals R³ such as are given for compounds of general formula (I) can be introduced either at the stage of the leuko coloured materials of general formula (V'), in which R³ is a hydrogen atom, or at the stage of the protected per-C-substituted N-acetylglucosaminide, as occurs in the case of the preparation of compounds of general formula (I), in which G is a glycoside residue. Activated acid derivatives, for example halides, anhydrides and mixed anhydrides are used, such as are known from peptide chemistry.

Starting from compounds of general formula (I), compounds of general formula (V') can, of course, also be obtained by reaction with an appropriate hydrolase.

The coloured materials of general formula (VII) necessary for the preparation of compounds of general formula (V') are also new. They are preferably obtained by the oxidative coupling of an amino compound of the general formula:

$H_2N-L$ (VIII)

in which L has the meaning given in general formula (I) but is preferably a pyrazolo-heterocyclic radical of general formula (III) in which X-Y and Z have the meanings given for compounds of general formula (I), with a phenol of the general formula:

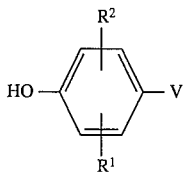
(IX)

in which R¹ and R² have the meanings given in compounds of general formula (I) and V is a hydrogen or halogen atom or a carboxyl or SO₃H group.

For this purpose, an amino compound of general formula (VIII) and a phenol of general formula (IX), preferably in which V is a hydrogen atom, are reacted in the presence of an oxidation agent, or example potassium ferricyanide, potassium peroxodisulphate, potassium peroxomonosulphate, iodine, hydrogen peroxide/peroxidase, lead dioxide, sodium hypochlorite, sodium hypobromite or an organic oxidation agent, for example K-bromosuccinimide or a related compound.

Furthermore, the coloured material or general formula (VII) can also be prepared by the reaction of N-haloimines of the general formula:

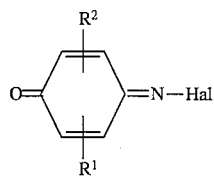
(XI)

in which R¹ and R² have the meanings given for compounds of general formula (I) and Hal is a halogen atom, whereby halogen is fluorine, chlorine, bromine or iodine and preferably chlorine, with compounds of the general formula:

L-H (X)

in which L has the meaning given for general formula (I) but is preferably a pyrazolo-heterocyclic radical of general formula (III), whereby X-Y and Z have the meanings given for general formula (I).

The reaction conditions can be chosen analogously to those described in Houben-Weyl, Vol. 7.3, pp. 296 et seq. Starting from compounds of general formula (I), coloured materials of general formula (VII) can also be obtained by reaction with an appropriate hydrolase and subsequent oxidation. For the oxidation, there can, in principle, be used the same substances which were described for the oxidative coupling between compounds of general formula (VIII) and those of general formula (IX).

Coloured materials of general formula (VIII) can advantageously also be obtained by reaction of a compound of the general formula:

L-E (XXV)

in which E is a nitroso or nitro group and L is a pyrazolo-heterocyclic radical of general formula (III), whereby X-Y and Z have the meanings given for general formula (I), with an organo-metallic compound of the general formula:

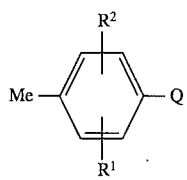
(XXVI)

in which R¹ and R² have the meanings given for general formula (VIII), Me is lithium or magnesium substituted by halogen and Q is a hydroxyl group or a dialkylamino radical, and subsequent aqueous working up of the reaction mixture. Radicals present possibly in the compound of general formulae (XXV) and (XXVI) which are not to react with the Grignard or lithium compound are to be appropriately protected. Information regarding such protective groups is to be found, for example, in T. Greene, "Protecting Groups in Organic Synthesis", pub. John Wiley and Sons, New York, 1981; J. F. W. McOmie, "Protective Groups in Organic Chemistry", pub; Plenum Press, London, 1973. If the compounds of general formula (XXV) do not contain any functional groups (apart from a nitro or nitroso group) which can react with organo-metallic compounds, or example ester groups, then such a reaction is preferred for the preparation of compounds of general formula (VII). Disturbing radicals can possible by protected and, after the reaction with the organo-metallic compound, the protective groups are again removed.

If Q is an N, N-dialkylamino radical and especially a dimethylamino radical, then the coloured materials of the general formula:

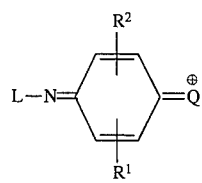

(XXVI')

in which R¹ and R² have the same meanings are given for general formula (XXVI), L is the radical described in more detail for general formula (XXV) and Q is a dialkylamino radical, which are formed as intermediates can be isolated and converted by alkaline hydrolysis, for example with sodium carbonate in water/ethanol, into the desired coloured materials of general formula (VII).

The reaction of nitroso or nitro compounds with organolithium of Grignard compounds is described in Houben-Weyl, Methoden der organischen Chemie, Vol, 10/1, pp. 1087, 1126; J. Chem. Soc., C, 2119/1971 and leads, depending upon on the excess used, to hydroxylamine derivatives or to secondary amines and further products. Surprisingly, we have found that the compounds of general formulae (XXV) and (XXVI), in the case of the use of equimolar amounts and subsequent aqueous working up of the reaction mixture, can be reacted with high yields to give coloured materials of general formula (VII).

For the amino compounds of general formula (VIII), there are the following methods of preparation. When L is the radical of general formula (II), as is defined for compounds of general formula (I), these amino compounds are known or can be prepared analogously to the known compounds. Usually, correspondingly substituted N,N-anilines are used as starting materials which are nitrosated. Reduction of the nitroso group gives the p-phenylenediamine derivatives of the general formula L-NH$_2$ (see J.A.C.S., 73, 3100/1951).

Compounds of general formula (VIII), wherein L is a pyrazolo-heterocyclic radical of general formula (III), can be prepared analogously to known methods by converting a compound of general formula (X), in which L is a pyrazolo-heterocyclic radical of general formula (III), by known methods into the corresponding amino compound. This can be achieved a) by reaction with nitric acid or nitric acid in admixture with sulphuric acid and/or acetic anhydrids to given the corresponding nitro compound or b) by reaction with nitrous acid to given the corresponding nitroso compound or c) by reaction with an aromatic diazonium salt to give the corresponding arylazo compound and subsequent reduction.

Nitro, nitroso and arylazo radicals, i.e. radicals of the general formula aryl-N=N— in which aryl can have the same meanings as described hereinbefore for aryl radicals and other groups containing such radicals, can be converted into amino groups by reduction with reagents such as zinc into an acid, for example hydrochloric acid or acetic acid, sodium dithionite, tin in an acid, for example hydrochloric acid, stannous chloride or by catalytic hydrogenation, for example in the presence of palladium-carbon. Such reactions are described in Houben-Weyl, Methoden der organischen Chemie, Vol. 11/1, p. 341 et seq.

The introduction of nitro, nitroso or arylazo groups starting from compounds of general formula (X) can take place by nitration with nitric acid or nitric acid in admixture with concentrated sulphuric acid or acetic anhydride.

By nitrosation with nitrous acid or by azo coupling with aromatic diazonium salts, the nitroso group or an arylazo radical can be introduced. Examples of such reactions are described in Houben-Weyl, Methoden der organischen Chemie, Vol. 10/1 and 10.3.

If heterocyclic compounds of general formula (X) are present in which H is not a hydrogen atom but rather a carboxyl, alkoxycarbonyl, or alkylcarbonyl radical, then these can be converted by hydrolysis with concentrated hydrochloric acid or, in the case of carboxylic acid, by thermal decarboxylation, into compounds of general formula (X). This is then followed by the introduction of an nitro, nitroso or arylazo radical.

Nitrogen atoms which are not on a double bond and in which the radicals X-Y or Z of general formula (III) occur can optionally be alkylated or aralkylated. The N-alkylation or N-aralkylation can be carried out by reaction of the appropriate compounds of general formula (X) by preferably of those heterocyclic compounds in which H is not a hydrogen atom but rather nitro, nitroso, alkoxycarbonyl, acyl or arylazo, with alkylation or aralkylation agents, for example alkyl or aralkyl halides, dialkyl or diaralkyl sulphates or arylsulphonic acid alkyl esters or aralkyl esters in the presence of a base, for example sodium hydride, a tertiary amine, an alkali metal carbonate or sodium hydroxide, in a solvent, for example dimethylformamide or an aqueous alcoholic system.

The required starting compounds of general formula (X) or those compounds corresponding to general formula (X) in which H is replaced by alkoxycarbonyl or acyl, whereby L is a pyrazolo-heterocyclic radical of general formula (III), have been described or can be synthesised analogously to known compounds. Information regarding the preparation of the heterocyclic systems is contained in the following publications: G. P. Ellis, "Synthesis of fused Heterocycles" in "the Chemistry of Heterocyclic Compounds", E. C. Taylor ed., pub. John Wiley & Sons; P. H. Preston, "Condensed Imidazoles", in "The Chemistry of Heterocyclic Compounds", A. Weissberger and E. C. Taylor eds., 1986, pub. John Wiley & Sons; Adv. of Het. Chem., 36, 343/1984; Chem Pharm. Bull., 22, 482/1974; J. Het. Chem., 12, 481,1975; Chem Pharm. Bull., 22, 1841/1974; Ann., 660, 104/1962; Chem. Pharm. Bull., 23, 452/1975; J. Het. Chem., 10, 411/1973; J. Chem. Soc. Perkin I, 2047/1977.

The compounds of general formula (I) are outstandingly useful as hydrolase substrates. Especially preferred for this use are compounds of general formula (I) as have been described hereinbefore. Quite especially preferred are compounds of general formula (I) in which G is an N-acetyl-β-D-glucosaminidyl radical for use as substrate for the enzyme N-acetyl-β-D-glucosaminidase (NAGase).

For the carrying out of the process according to the present invention for the colorimetric determination of a hydrolase, a compound of general formula (I) is reacted, as enzyme substrate, with the enzyme to be determined, the leuko coloured material resulting from the substrate cleavage is oxidised and the coloured material resulting therefrom is determined visually or photometrically. It represents a measure for the amount of enzyme to be determined.

For the oxidation of the leuko coloured material of general formula (V) first resulting by the action of the hydrolase, there can be used any oxidation agent which does not influence the activity of the enzyme to be determined and which is strong enough to oxidise the resulting leuko coloured material. As a rule, as oxidation agent there is used potassium ferricyanide, perborate, bilirubin oxidase, peroxidase/hydrogen peroxide or, preferably, iodate.

As can be gathered from the above remarks, a reaction of the substrate by the enzyme in the presence of the oxidation agent is preferred. However, it is also possible to carry out the hydrolase reaction and the oxidation separately. However, according to the latter procedure, a kinetic determination is not possible but only an end point determination.

It is self-evident that a buffer system adjusted to the enzyme must be present for carrying out the determination process. Which buffer is the most suitable is known. For example, the determination process according to the present invention for N-acetyl-β-D-glucosaminidase as hydrolase is carried out at a pH value of from 3.5 to 7.0 and preferably of from 4.0 to 6.5.

The diagnostic agent for the determination of a hydrolase according to the present invention contains, besides one or more substrates of general formula (I) according to the present invention, an appropriate buffer system, as well as possibly further appropriate additives conventional for such reagents, for example further adjuvant enzymes, stabilisers and the like. The oxidation agent necessary for the formation of the coloured material after cleavage of the enzyme substrate can be present together with the other substances necessary for the determination process or can be separate therefrom. The reagent according to the present invention can be present in the form of a solution, as a lyophilisate, as a powder mixture, as a reagent tablet or on an appropriate carrier material, whereby the reagent together, separately or, depending upon compatibility and expediency, combined with one another.

The diagnostic agent according to the present invention in the form of a solution preferably contains all the reagents required for the test. As solvent, there can be used water or mixtures of water with a water-soluble organic solvent, for example methanol, ethanol, acetone or dimethylformamide. For reasons of storage stability, it can be advantageous to divide the reagents required for the test into two or more solutions which are first mixed together in the case of carrying out the actual investigation.

For the preparation of the diagnostic agent in the form of a lyophilisate with a total weight of, in each case, about 5 to 20 mg. and preferably of about 10 mg., a solution is dried which contains all reagents needed for the test, as well as conventional structure formers, for example polyvinylpyrrolidone and possibly further filling materials, for example mannitol, sorbitol or xylitol. However, the oxidation agent can be present in the diagnostic agent separated from the other components. This can be achieved by separate lyophilisation or by admixture of the undissolved oxidation agent.

A reagent in the form of a powder mixture or reagent tablet can be prepared by mixing the components of the test with conventional galenical additives and granulating. Additives of this kind include, for example, sugar alcohols, such as mannitol, sorbitol or xylitol, or other soluble insert compounds, such as polyethylene glycol or polyvinylpyrrolidone. In general, the power mixture or reagent tablet has an end weight of about 30 to 200 mg. and preferably of 50 to 80 mg.

Solid reagent mixtures, such as lyophilisates, powder mixtures or tablets, are, before use, dissolved in water or some other appropriate solvent and the reagent solution(s) thus prepared. After mixing the sample with a sufficient amount of the reagent mixture, the resultant colour is measured on a photometer and the particular enzyme concentration calculated via the molar extinction coefficient and the added volumes of reagent or sample. Not only kinetic by also end point measurements are possible.

For the production of the reagent in the form of a test strip, an absorbent carrier, preferably filter paper, cellulose or synthetic material fibre fleece, is impregnated with solutions of the necessary reagents conventionally used for the production of test strips in a ready volatile solvent, for example water, methanol, ethanol or acetone. This can take place in one impregnation step. However, it is often desirable to carry out the impregnation in several steps, whereby solutions are used which, in each case, contain a part of the components of the reagent. Thus, for example, in a first step, impregnation can be carried out with an aqueous solution which contains the oxidation agent, the buffer and possibly other water-soluble additives and then, in a second step, with a solution which contains the hydrolase substrate. The finished test strips can be used as such or can be stuck in known manner on to handles or preferably sealed between synthetic materials and fine meshes according to Federal Republic of Germany Patent Specification No. 21 18 455, U.S. Pat. No. 3,802,842.

Figure 5:
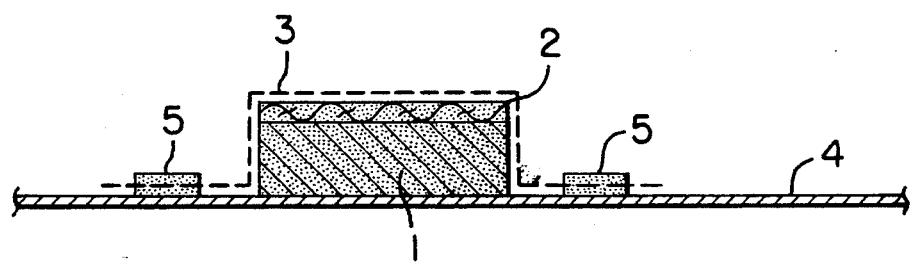
FIG. 5 shows the test carrier having paper, mesh, covering mesh and plastic film.

As preferred diagnostic agent according to the present invention, there is produced a test carrier according to FIG. 5 of the accompanying drawings. This test carrier consists of an absorbent carrier material, such as paper (1), containing a buffer and hydrolase substrate, arranged hereon, in planar contact with the absorbent carrier (1), a mesh (2) containing the oxidation agent, for example a mesh of polymeric material and a covering mesh (3) fixing (1) and (2) on a handle of plastic film (4) in order to simplify handling. This covering mesh (3) can also consist of a polymeric material. The covering mesh (3) itself is fixed by means of a melt adhesive (5) on to the film (4).

For carrying out a hydrolase determination, the sample to be investigated is applied to the covering mesh (3) of the test carrier according to FIG. 5 or this is dipped into the liquid sample to be investigated. The sample quickly penetrates through the covering mesh (3) and, with dissolving of the oxidation agent, through the mesh (2) into the absorbent material (1) where, in the case of the presence of the enzyme, enzymatic cleavage of the there-present enzyme substrate and oxidation of the intermediate formed leuko coloured material to the determinable coloured material takes place.

A semi-quantitative determination is possible by associating the resultant colour with a comparison colour. A quantitative evaluation can take place remission photometrically.

As a rule, the compounds of general formula (I) are sufficiently storage-stable for use in diagnostic agents according to the present invention. However, we have ascertained that the stability of the hydrolase substrates according to the present invention can be still further increased when they are present together with compounds of the general formula:

$$Ar—NH—NH—CONH_2 \quad (XII)$$

wherein $A_r$ is an aryl radical optionally substituted by alkyl, alkoxy or halogen.

In this connection, alkyl, alkoxy, halogen and aryl have the same meanings as given hereinbefore for the substituents in general formula (I). Especially advantageous compounds of general formula (XII) are p-methyl-, o-methoxy-, m-methoxy-, p-methoxy, o-chloro-, m-chloro-, o-chloro-, o-methyl-, m-methyl- and unsubstituted phenylsemicarbazides, as well as naphthyl semicarbazide.

The compounds of general formula (XII) have proved to be quite especially advantageous for increasing the storage stability of N-acetylglucosaminides according to the present invention.

In the scope of the present invention, the compounds of general formula (I) display many advantages. In particular, it is of considerable advantage that the substrates according to the present invention are colourless and, in the case of carrying out the process according to the present invention, coloured substances are formed, the red or blue colour of which can clearly be ascertained. The large wavelength shift, i.e. the difference of the maximum absorption wavelengths of substrate and coloured material formed, makes possible very sensitive determinations. Such determinations are possible especially in biological fluids, for example plasma, serum and, in particular, urine since the resultant colour differs very clearly from the sample material. The coloured materials formed after cleavage of the substrates according to the present invention are formed over a very wide pH range. Above all, it is important that, according to the present invention, coloured materials are formed not only in the neutral and basic pH region but also already at pH values in the rather acidic range, i.e. from pH 3.5, so that no rebuffering is necessary in the case of a determination of "acidic" enzymes, i.e. those enzymes which display their activity maximum in the acidic pH range. This makes the compounds of general formula (I) according to the present invention especially appropriate substrates for "acidic" enzymes, for example NAGase. The carrying out of the hydrolase determination according to the present invention at the pH optimum of the enzymes with non-coloured substrates makes possible the rapid detection even of low enzyme concentrations. Finally, the substrates according to the present invention are suitable not only for wet chemical determinations in solutions but also for dry chemical determinations on test carriers. The evaluation can take place visually or photometrically in transmission or remission.

The following Examples are given for the purpose of illustrating the present invention:

EXAMPLE 1

4-(4'-Dimethylaminophenylamino)-phenyl-2-acetamido-2-deoxy-β-D-glycopyranoside

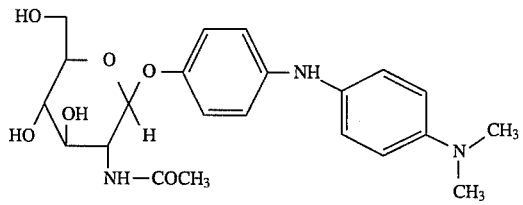

To prepare the starting material N,N-Dimethylindoaniline (Phenol Blue III)—A solution of 0.075 mole of phenol, 4 g (0.1 mole) of sodium hydroxide, and 8 g (0.06 mole) of sodium acetate in 250 c.c of water was stirred mechanically in a salt-ice bath in such a way as to maintain a temperature of 0° to 5° during the reaction. Two dropping funnels were put in place, one containing 100 cc (0.1 mole) of 5% sodium hypochlorite, the other a solution of 0.05 mole of p-aminodimethylaniline hydrochloride in 100 cc of water. The two solutions were then added simultaneously in the course of forty-five to sixty minutes. The solution became blue after the addition of a few drops of the reagents and the dye soon began to separate. Stirring was then continued for fifteen minutes after completion of the addition and the product was then collected and washed several times with water; the dark blue filtrate, probably containing phenol-indophenol formed by alkaline hydrolysis of the product was discarded. The crude dye was crystallized from ethyl acetate, giving fine, intense violet needles, m.p. 161° [as reported by Gnelm and Bots J. Prakt. Chem., 69:162 (1904)] Yield 7.2 g (63%). This is generally the method of Gnelm and Bots, Supra [see also Heller Ann 392:16 (1912) and Cohen and Phillips, Suppl. No. 74 U.S. Pub. Health Reports 1929].

1.1 6 g. N,N-Dimethylindoaniline (J.A.C.S., 61, 376/1939), are added to a solution of 7 g. sodium hydroxide in 250 ml. water. While stirring vigorously, sodium dithionite is added portionwise thereto until the blue colour has disappeared. The solution is filtered, the filtrate is cooled to about 5° C. and mixed dropwise with glacial acetic acid, until the precipitate has come out completely. The precipitate is filtered off and dissolved in 25 ml. concentrated hydrochloric acid. The solution is treated with carbon, filtered and evaporated. The residue is recrystallised from ethanol. There are obtained 3.1 g. (51% of theory) 4-dimethylamino-4'-hydroxydiphenylamine.

1.2 2.6 g. of the leuko coloured material obtained in 1.1, 8.83 g. 2-acetamido-3,4,6-tri-O-acetyl-2-doxyl-α-D-glucosyl chloride and 4.21 g benzyltriethylammonium bromide are added to a mixture of 125 ml. chloroform and 125 ml. water. The mixture is vigorously stirred, mixed with 8.7 g. potassium carbonate and boiled under reflux for 6 hours, whereby after 3 hours, 4.4 g of the halogenase and 4.3 g. potassium carbonate are added thereto. The chloroform phase is separated off, dried with anhydrous sodium sulphate and evaporated.

The residue is chromatographed on silica gel with ethyl acetate. The product-containing fractions are evaporated. There are obtained 500 mg (9% of theory) of the protected sugar derivative of the following formula:

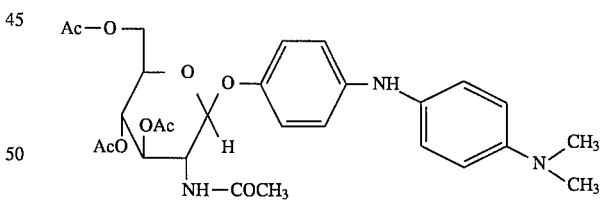

1.3 460 mg. of the protected sugar derivative obtained on 1.2 are dissolved in 10 ml. methanol, mixed with 0.9 g. sodium bicarbonate and vigorously stirred for 3 hours at ambient temperature. The reaction mixture is filtered, the filtrate is evaporated and the residue is chromatographed on silica gel with ethyl acetate/methanol (8:2 v/v). The product-containing fractions are combined and evaporated. The residue is taken up in a little methanol and the solution is mixed with diethyl ether. The precipitate thus obtained is filtered off with suction and washed with diethyl ether. There is obtained 0.34 g. (96% of theory) of the title compound; m.p. 207°–209° C. (decomp.).

EXAMPLE 2

4(N-acetyl-4'-dimethylaminophenyl)-amino-phenyl-2-acetamido-2-deoxy-β-D-glucopyranoside

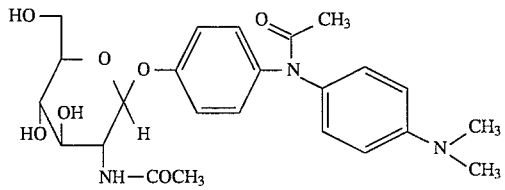

0.3 g. of the protected glycoside obtained in Example 1.2 is mixed with 5 ml. acetic anhydride, heated to 80° C. and maintained at this temperature for 2 hours. The reaction mixture is evaporated and the residue is mixed with diethyl ether. The precipitate obtained is filtered off and, for the splitting off of the protective groups, is treated with sodium bicarbonate, analogously to Example 1.3, in methanol. The crude product is chromatographed over silica gel with toluene/ethyl acetate/methanol (1:1:1 v/c/v). There is obtained 0.1 g (47% of theory) of the title compound; m.p. 142°–144° C. $R_f$ (silica gel, toluene/ethyl acetate/methanol 1:1:1 v/v/v)=0.37.

EXAMPLE 3

4((4'-Dimethylaminophenyl-N-trifluoroacetyl)-amino)-phenyl-2-acetamido-2-deoxy-β-D-glucopyranoside

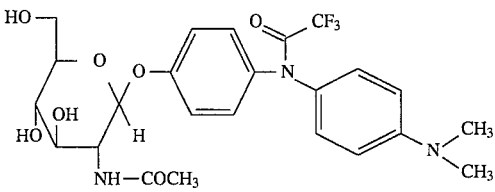

Analogously to Example 2, with the use of trifluoroacetic anhyride instead of acetic anhydride with with a reaction temperature of 0° C., there is obtained the title compound; m.p. 191°–198° C. $R_f$ (silica gel, toluene/ethyl acetate/methanol 2:1:1 v/v/v)=0.35.

EXAMPLE 4

Analogously to Examples 1.2 and 1.3, from the corresponding leuko coloured materials and 2-acetamido-3,4,6-tri-O-acetyl-2-deoxy-α-D-glucosyl chloride, there are obtained the compounds set out in the following Table 1.

TABLE 1

| No. | structure | m.p. °C. | $R_f$ | leuko coloured material component; prepn. see |
|---|---|---|---|---|
| 4 a | 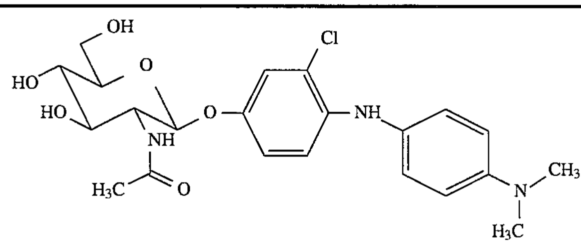 | 180–188 | 0.56[2)] | 4.1 |
| 4 b | 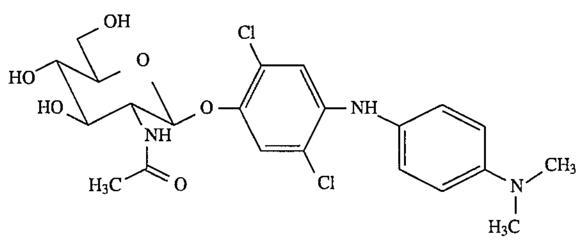 | 197 | 0.27[1)] | 4.2 |
| 4 c | 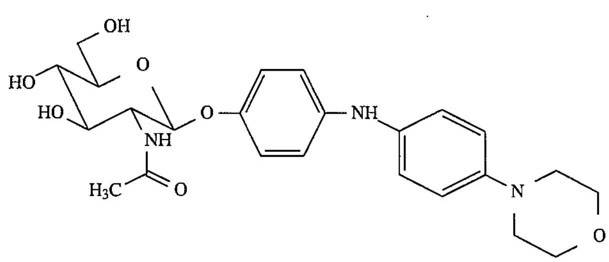 | 205 | 0.16[1)] | 4.2 |

TABLE 1-continued

| No. | structure | m.p. °C. | $R_f$ | leuko coloured material component; prepn. see |
|---|---|---|---|---|
| 4 d | (structure) | 194 | 0.16[1] | 4.2 |
| 4 e | (structure) | 188–191 | 0.35[2] | 4.3 |
| 4 f | (structure) | 195 | 0.35[1] | 4.2 |
| 4 g | (structure) | 210–212 | 0.5[2] | 4.2 |
| 4 h | (structure) | 143 | 0.27[1] | 4.4 |
| 4 i | (structure) | 212 | 0.40[1] | 4.5 |

[1] silica gel, toluene/ethyl acetate/methanol, 2:1:1 v/v/v
[2] silica gel, toluene/ethyl acetate/methanol, 1:1:1 v/v/v Preparation of the Leuko Coloured Material Components.

4.1 4-Dimethylamino-2'-chloro-4'-hydroxydiphenylamine

A solution of 7.7 ml. m-chlorophenol, 4 g. sodium hydroxide and 8 g. sodium acetate in 200 ml. water, cooled to 0° to −5° C., is mixed, with good stirring, simultaneously from two dropping funnels with, in each case, a solution of 10.45 g. N,N-dimethylphenylenediamine hydrochloride in 100 ml. water and 125 ml. of a 4% sodium hypochloride in 100 ml. water and 125 ml. of a 4 % sodium hypochlorite solution in the course of 45 to 60 minutes. The reaction mixture is subsequently stirred for 15 minutes and the precipitate is filtered off and washed several times with water. The residue is dissolved in a mixture of 50 ml. 2N aqueous sodium hydroxide solution, 30 ml. water and 20 ml. methanol and reduced at a temperature of about 40° to 45° C. (bath temperature) to the leuko coloured material by the addition of about 10 to 20 g. sodium dithionite. The reaction mixture is adjusted to pH 6 by the addition of glacial acetic acid and the precipitate obtained is filtered off with suction. For purification, the product is chromatographed over silica gel with ethyl acetate/ligroin (8:2 v/v). There are obtained 3.5 g. of the title compound.

4.2 The leuko coloured materials 4-dimethylamino-2',5'-dichloro-4'-hydroxydiphenylamine, 4-morpholino-4'-hydroxydiphenylamine, 4-dimethylamino-3'-chloro-4'-hydroxydiphenylamine and 4-morpholino-2'-fluoro-4'-hydroxydiphenylamine are obtained analogously to 4.1 by the oxidative coupling of the appropriate phenylenediamine with the correspondingly substituted phenol

4.3 4-Hydoxyphenyl-2-methylpyrazolo[1,5-a]-pyridin-3-yl-amine 4.3.1 7 g. 3-Acetyl-2-methylpyrazolo[1,5-a]pyridine are dissolved in 140 ml. 6N hydrochloric acid and mixed dropwise at 0° C. with a solution of 5.52 g. sodium nitrite in water. After 2 hours, the ice-bath used for cooling is removed, the reaction mixture is left to stand overnight at ambient temperature and then adjusted to pH 9. The precipitated nitroso compound (6.4 g.) is filtered off with suction and dissolved in about 150 ml. 2N hydrochloric acid. The nitroso compound is reduced with stannous chloride analogously to Example 4.4.1.2. The crude product is chromatographed on silica gel with ethyl acetate. The product-containing fractions are evaporated, the residue is dissolved in ethanol and mixed with ethanolic hydrochloric acid. The precipitate which comes put after some time is filtered off with suction and dried. There are obtained 3.1 g. (45% of theory) 3-amino-2-methylpyrazolo-[1,5-a]pyridine hydrochloride; m.p.>275° C.; $R_f$ (silica gel, ethyl acetate/acetone/glacial acetic acid/water 50:25:12.5:12.5 v/v/v/)=0.6

4.3.2 2.82 g. Phenol are dissolved in 75 ml pyridine and the solution is mixed with 450 ml. water. A solution of 5.5 g. 3-amino-2-methylpyrazolo[1,5-a]pyridine hydrochloride from 4.3.1 in 150 ml. water is then added thereto and the reaction mixture is subsequently mixed, while stirring, with a solution of 78 g. potassium ferricyanide in 450 ml. water. The precipitated blue-coloured material is filtered off with suction, washed with water and dried. Yield 4.85 g.

TLC (silica gel, ethyl acetate/methylene chloride 1:1 v/v): $R_f$=0.5.

4.3.2.1 Alternative synthesis of the coloured material N-(2-methylpyrazolo[1,5-a]pyridin-3 -yl)quinonimine From 7.7 g. 4-bromodimethylaniline and 1.4 g. magnesium turnings in 60 ml. dry tetrahydrofuran is prepared the corresponding Grignard compound (see J. Chem. Soc., 465/1961). The reaction solution is sucked off with a syringe and added dropwise to a solution, cooled to −15° C., of 3.05 g. 3-nitroso-2-methylpyrazolo[1,5-a]pyridine (prepared according to Example 4.3.1) in 60 ml. tetrahydrofuran. After warming, the reaction mixture is mixed with 100 ml. ethanol and an excess of sodium carbonate until the reaction is alkaline. For the oxidation of the resultant leuko coloured material, there is added thereto a total of 40 g. potassium ferricyanide and the reaction mixture is then stirred at ambient temperature. After hydrolysis is complete, the reaction mixture is extracted with ethyl acetate. The organic phase is evaporated and the residue is chromatographed on silica gel with the elution agent ethyl acetate/ligroin (1:1 v/v). There are obtained 4.4 g. (98% of theory, referred to the nitroso compound) of the coloured material. $R_f$ (silica gel, methylene chloride/ethyl acetate (1:1 v/v))+0.6.

4.3.3 For reduction to the leuko coloured material, the coloured material is dissolved in 200 ml. ethyl acetate and the solution is mixed with about 100 ml. saturated aqueous sodium carbonate solution. Until decolorised, the solution is vigorously shaken with sodium dithionite. The organic phase is separated off, dried and concentrated to a small volume. This is then mixed with ligroin and the precipitate obtained is filtered off, washed with ligroin and subsequently dried. There are obtained 4.45 of the title compound which is pure enough for further working up. A purification is possible by chromatography over silica gel with methylene chloride/methanol (98:2 v/v). $R_f$ (silica gel, ethyl acetate/methylene chloride (1:1 v/v))=0.6. $R_f$ (silica gel, methylene chloride/methanol (95:5 v/v))=0.3.

4.4 4-Hydroxyphenyl-pyrazolo[1,5-a]-pyridin-3-ylamine 4.4.1 2 g. Pyrazolo[1,5-a]pyridine are dissolved in 30 ml. 6N hydrochloric acid, the solution is cooled to 0° C. and a solution of 6.9 g. sodium nitrite in 30 ml. water is slowly added dropwise thereto. After 1 hour, the nitrosation is complete. About 100 ml. water are added thereto, followed by repeated extraction with ethyl acetate. The organic phase is dried and evaporated. There are obtained 9.6 g. 3-nitrosopyrazolo[1,5-a]pyridine.

4.4.2 9 g. of the nitrose compound obtained according to 4.4.1 are introduced into a solution of 22 g. stannous chloride dihydrate in 180 ml. concentrated hydrochloric acid. The reaction mixture is stirred for 1 hour at ambient temperature and, for the completion of the reduction, mixed with 8 g. stannous chloride dihydrate in 30 ml. concentrated hydrochloric acid. The suspension is poured on to about 150 g. ice, adjusted with sodium hydroxide to pH 12 and quickly extracted with ethyl acetate. The ethyl acetate phase is dried and evaporated. The residue is dissolved in about 350 ml. diethyl ether and mixed with ethereal hydrochloric acid. The precipitate obtained is filtered of, washed with diethyl ether and dried. There are obtained 11.3 g. (100% of theory) 3-amino-pyrazolo[1,5-a]pyridine hydrochloride; m.p. 228°–232° C. $R_f$ (silica gel, ethyl acetate/methanol 9:1 v/v)=0.52.

4.4.3 The leuko coloured material 4-hydroxyphenyl-pyrazolo[1,5-a]pyridin-3-ylamine is obtained analogously to 4.3.2 and 4.3.3 with the use of 3-aminopyrazolo[1,5-a]-pyridine as starting material. $R_f$ (silica gel, ethyl acetate/diethyl ether 1:1 v/v)=0.68.

4.5 4-Hydroxyphenyl-2-methylthiopyrazolo[1,5-a]-pyridin-3-ylamine

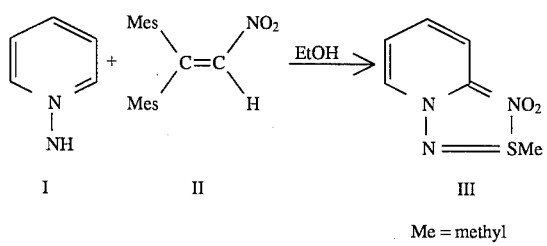

Me = methyl

With 2,2-bis(methylthio)-1-nitroethylene (II) a reaction with Ia afforded 2-methylthio-1-nitropyrazolo[1,5-a] pyridine (III) as yellow needles, M.p. 224.6° in 41% yield. The product where R is H.

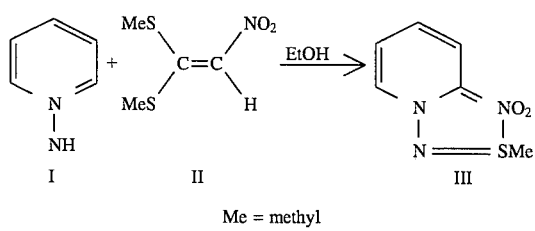

Me = methyl 4.5.1 4 g. 2-methylthio-3-nitropyrazolo[1,5-a]pyridine (see Heterocycles, 6, 379 (1977), Chem. Pharm. Bull. 25 1528/1977) are dissolved in 200 ml. concentrated hydrochloric acid and mixed with 20 g. stannous chloride dihydrate. After 1 hour, 15 g. stannous chloride dihydrate, 15 ml. concentrated hydrochloric acid and 200 ml. water are again added thereto. After a further reaction period of 1 hour, the reaction mixture is poured on to ice, the yellow solution is rendered alkaline with sodium hydroxide and extracted with ethyl acetate. The organic phase is dried and evaporated. The residue is dissolved in a little ethanol and mixed with ethereal hydrochloric acid in order to form the hydrochloride. There are obtained 3.9 g. (95% of theory) 3-amino-2-methylthiopyrazolo[1,5-a]pyridine hydrochloride; m.p. 260° C. $R_f$ (silica gel, methylene chloride/tert.-butyl methyl ether 2:8 v/v)=0.66.

4.5.2 The leuko coloured material 4-hydroxyphenyl-2-methylthiopyrazol[1,5-a]pyridin-3 -ylamine is obtained analogously to 4.3.2 and 4.3.3 with the use of 3-amino-2-methylthiopyrazolo[1,5-a]pyridine. $R_f$ (silica gel, ethyl acetate/ligroin 1:1 v/v)=0.47.

EXAMPLE 5

4-((R,S-2-(1-Hydroxyethyl)-pyrazolo[1,5,a]pyridin-3-yl)-amino)-phenyl- 2acetamido-2-deoxy-β-D-glucopyranoside.

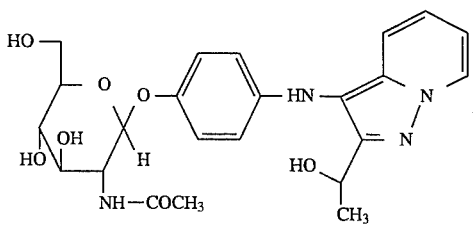

5.1 4-Hydroxyphenyl-2-(1-hydroxyethylpyrazolo[1,5-a]-pyridine-3-yl)-amine 25 g. N-Aminopyridine hydrochloride are dissolved in 250 ml. dry dimethylformamide and mixed, while stirring, with 17.5 g. potassium carbonate. Subsequently, while stirring, 20.2 g. R,S-2-hydroxy-5-oxohex-3-yne (J. Chem. Soc. Perkin I, 1908/1976) are added dropwise thereto. The reaction mixture thereby warms up and is left to stand overnight. After the addition of 1.25 liters water, the reaction mixture is extracted several times with ethyl acetate. The combined extracts are dried and evaporated. The remaining oil is diluted with some diethyl ether. The crystals which precipitate out after some time are filtered off with suction. There are obtained 9.8 g. (42% of theory) R,S-3-acetyl-2-(1-hydroxyethyl)-pyrazolo[1,5-a]pyridine ($R_f$ (silica gel, methylene chloride/ethyl acetate 1:1 v/v=0.35) which is nitrosated analogously to Example 4.3.1. The nitroso compound is suspended in ethanol and mixed with 2 g. palladium on carbon. The reaction mixture is heated to 80° C. and 2.5 ml. hydrazine hydrate are added portionwise thereto. After 10 minutes, the palladium-carbon is filtered off and the filtrate is evaporated. The residue is dissolved in ethanol and mixed with ethanolic hydrochloric acid. There are obtained 6.8 g. R,S-3-amino-2-(1-hydroxyethyl)-pyrazolo[1,5-a]pyridine hydrochloride in the form of crystals, which contain 1.8 mole hydrogen chloride and melt at 229°–231° C. $R_f$ (silica gel, ethyl acetate/methanol 3:1 v/v)=0.65.

Analogously to Example 4.3.2, 3.08 g. phenol are reacted with the amino compound obtained and the blue-coloured material is reduced analogously to Example 4.3.3. The crude product is chromatographed over silica gel with ethyl acetate/methylene chloride (1:1 v/v) as elution agent. There are obtained 3.4 g. of the title compound. $R_f$ (silica gel, ethyl acetate/methyl chloride 1:1 v/v)=0.2

5.2 Analogously to Example 1.2 and 1.3, from the leuko coloured material from 5.1 and 2-acetamido-3,4,8-tri-O-acetyl-2-deoxy-α-D-glucosyl chloride, there is obtained the title compound. $R_f$ (silica gel, toluene/ethyl acetate/methanol 1:1:1 v/v/v)=0.25; m.p. 165°–170° C. (decomp).

To prepare Hex-3-yne-2,5-dioxe: Chromium trioxide (100 g) in concentrated sulphuric acid (90 ml) and water (550 ml) was added with vigorous stirring over 2 hours to hex-3-yne-2,5-diol (28 g) and 5-hydroxyhex-3-yn-2-one (28 g) in acetone (400 ml) at −5° to 0° C. After 1 hour, water (150 ml) was added and the solution extracted with ether. The extract was washed (aqueous NaHCO$_3$), dried (MgSO$_4$) and distilled to give crude hex-3-yne-2,5-dione (3–6 g), B.P. 50° (bath) at 0.15 m Hg ad 5-hydroxy-hex-3-yne-2-one (B.P. 50°–75° at 0.2 mm Hg) 23 g.

EXAMPLE 6

Wet chemical determination of N-acetyl-β-D-glucosaminidase (β-NAGase)

900 μl. of solution of 4 mM substrate in 200 mM citrate buffer (pH 5.) are placed in a cuvette. To this are pipetted:

1. 100 μl. of a 220 mM potassium iodiate solution and 2. 100 μl. of a solution containing β-NAGase, mixed and the kinetics measured at a wavelength corresponding to the substrate. Calibration curves according to FIGS. 1–4 of the accompanying drawings can be obtained with solutions containing known concentrations of NAGase.

6.1 The substrate from Example 4e) gives, at $\lambda_{max}$ 560 nm, a calibration curve for the determination of β-NAGase according to FIG. 1 of the accompanying drawings. In the case of the presence of β-NAGase, the colour of the substrate changes from colourless to blue-violet.

Figure 2:
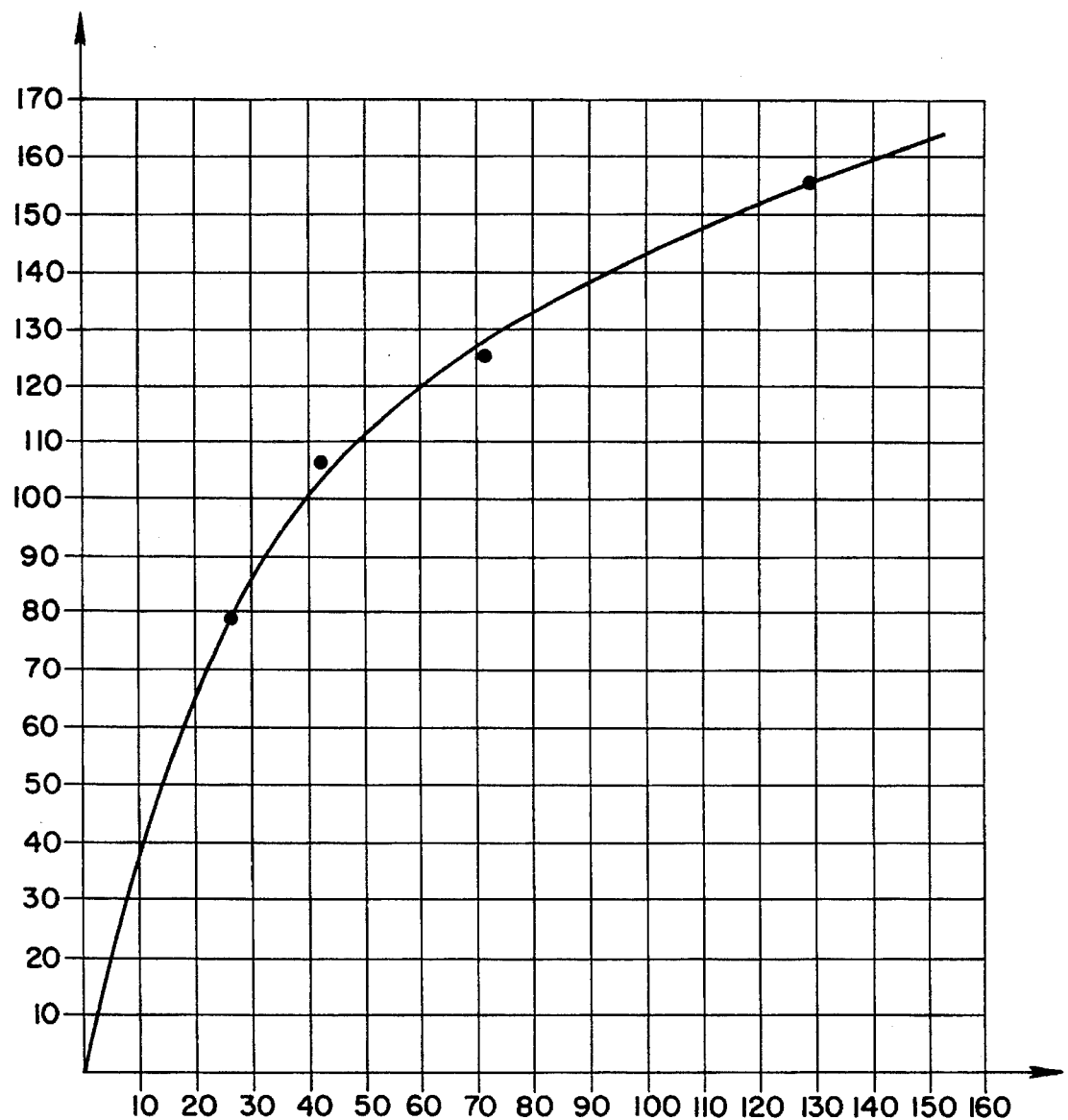
FIG. 2 shows a calibration curve at λmax 573 nm for the substrate of example 4g.

6.2 The substrate from Example 4g) gives, at $\lambda_{max}$ 573 nm, a calibration curve for the determination of β-NAGase according to FIG. 2 of the accompanying drawings. In the case of the presence of β-NAGase, the colour of the substrate changes from colourless to blue-violet.

Figure 3:
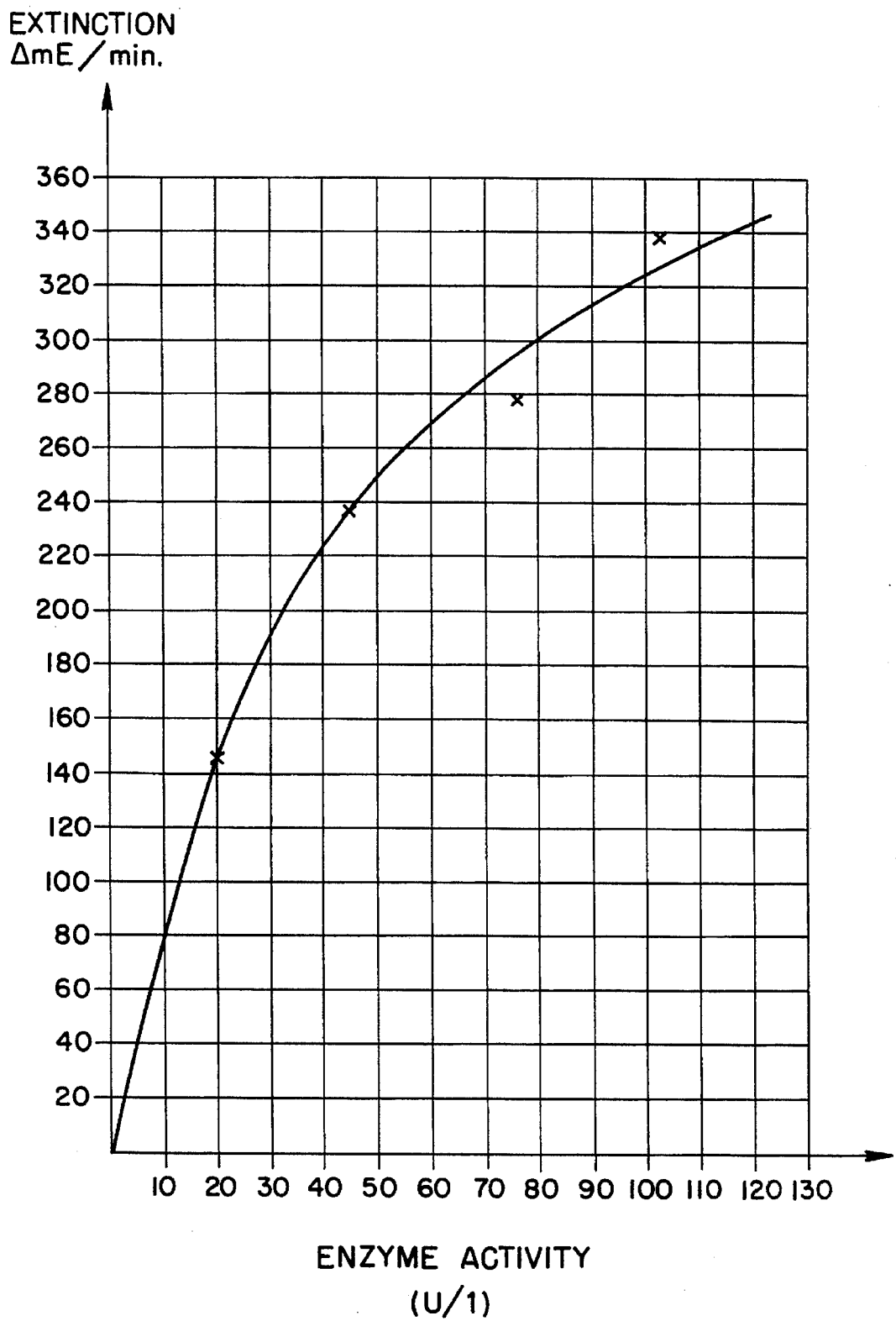
FIG. 3 shows the calibration curve at λmax 525 nm for the substrate of example 4(h)

6.3 The substrate from Example 4b) gives, at $\lambda_{max}$ 525 nm, a calibration curve for the determination of β-NAGase according to FIG. 3 of the accompanying drawings. In the case of the presence of β-NAGase, the colour of the substrate changes from colourless to red-violet.

Figure 4:
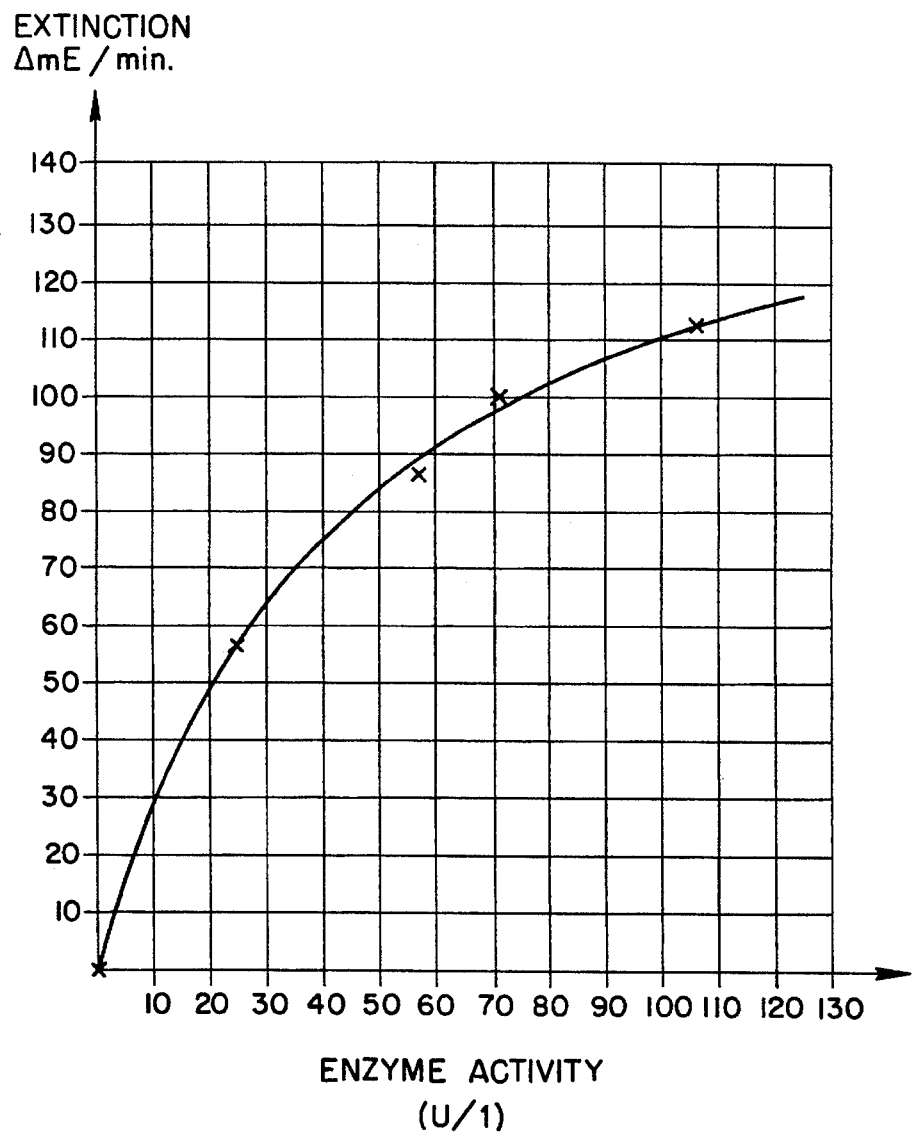
FIG. 4 shows the calibration curve at λmax 565 nm for the substrate of example 5.

6.4 The substrate from Example 5 gives, at $\lambda_{max}$ 565 nm, a calibration curve for the determination of β-NAGase according to FIG. 4 of the accompanying drawings. In the case of the presence of β-NAGase, the color of the substrate changes from colourless to blue-violet.

EXAMPLE 7

Test Strips for the Determination of β-NAGase a) A filter paper of the firm Schleicher & Schüll (23 SL) is successively impregnated with the following solutions and dried:

| | |
|---|---|
| 1. citrate buffer | 200 mMole/liter, pH 5 |
| potassium iodate | 20 mMole/liter |
| 2. indicator | 10 mMole/liter |

As indicator, there is used:

α) the compound of Example 4e)

β) the compound of Example 4h)

When the so-produced test strip is dipped into a solution containing NAGase, then, after about 5 minutes, above about 10 U/liter β-NAGase (the activity is determined according to the present reference method with sulphophthaleinyl-N-acetyl-β-D-glucosaminide as enzyme substrate) there is obtained a coloration of the test strip from colourless to blue when the compound of Example 4e) is used and from colourless to red in the case of using the compound of Example 4b). Higher enzyme activities lead to more intensive coloration.

b) A comparable result is achieved when the test strip from a) above is so modified that the reagent paper is impregnated as above but with a solution without iodate. The oxidation agent is impregnated from a 4C mMole/liter aqueous sodium iodate solution on to a nylon mesh (NY75HC of the firm Zürcher Peuteltuchfabrik, Zürich, Switzerland) with a filament thickness of 60 μm. From the paper (1) containing buffer and indicator, the mesh (2) containing the oxidation agent, a covering mesh (3) of the same material as mesh (2) and a stiff plastic film (4) of polystyrene is produced a test carrier according to FIG. 5 of the accompanying drawings. For this purpose, the paper (1) and the mesh (2) are cut up into 6 mm.×6 mm. sized pieces and fixed with a 12 mm.×6 mm. sized piece of covering mesh (3) by means of melt adhesive (5) on to a 100 mm. ×6 mm. sized piece of plastic film (4).

Upon dipping such a test strip into a solution containing β-NAGase, a coloration takes place from colourless to blue for the compound 4e) and from colourless to red for the compound 4b). Higher enzyme concentrations lead to more intensive coloration.

EXAMPLE 8

N-(p-toluenesulphonyl)-L-alanine-(4-((2-methyl-pyrazolo[I,5-a]pyridin-3-yl)-amino-phenyl ester

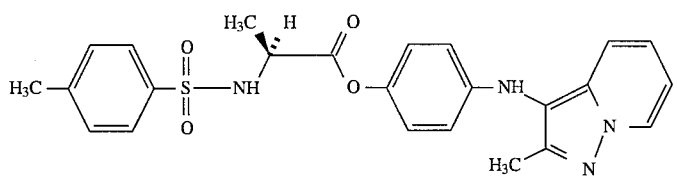

0.48 g. of the leuko coloured material obtained in Example 4.3 is dissolved in 8 ml. pyridine and, while stirring, mixed dropwise with a solution of p-toluene-sulphonyl chloride in 12 ml. chloroform. After briefly afterstirring, the reaction mixture is mixed with water and the organic phase is separated. The organic phase is well washed with water, separated and dried. The residue is chromatographed with the elution agent water/methanol on the adsorber resin HP 20SS (firm Mitsubishi). The product-containing fractions are evaporated and the residue is crystallised from diethyl ether/hexame. THere is obtained 0.54 g. of the title compound; m.p. 68°–78° C. (decomp).

$R_f$=0.7 (silica gel, ethyl acetate/methylene chloride, 1:1 v/v).

EXAMPLE 9

Phosphoric acid mono-)4-((2-methyl-pyrazolo[I,5-a]-pyridin-3-yl)-amino)-phenyl ester, pyridinium salt

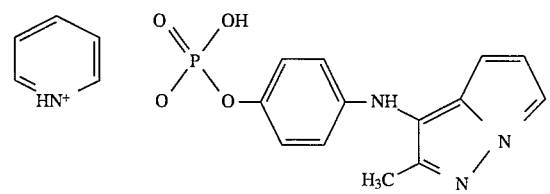

0.33 g. of the leuko coloured material obtained in Example 4.3 is dissolved in 3 ml. pyridine. The solution is cooled to −15° C. and, while stirring, mixed dropwise with a solution of 0.15 ml. phosphorus oxychloride in 2.5 ml. pyridine. The reaction mixture is stirred for 30 minutes at −15° C. and for 2 hours at ambient temperature, mixed with ice, acidified with 2N sulphuric acid to pH 2 and left to stand overnight in a refrigerator. The precipitate obtained is filtered off and the filtrate is passed over a column containing the absorber resin HP 20SS (Mitsubishi). The product is eluted with water. The product-containing fractions are combined, evaporated and the residue crystallised from methanol/diethyl ether. There is obtained 0.06 g. of the title compound: m.p. 158°–161° C. (decomp.).

EXAMPLE 10

(4-(2,4-D-methylpyrazolo[1,5-a]imidazol-3-yl)-amino)-phenyl- 2-acetamido-2-deoxy-β-D-glucopyranoside

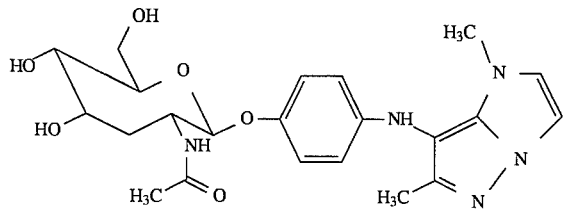

10.1 1.92 g. 1,2-dimethylimidazole are dissolved in 10 ml. methylene chloride and, while cooling with ice, mixed with a solution of O-p-toluenesulphonyl hydroxylamine, which was obtained by the reaction of 15.4 g. O-p-toluenesulphonyl acethydroxamic acid ethyl ester with 118 ml. 60% aqueous perchloric acid. The reaction mixture is stirred for 3 hours at ambient temperature. The precipitate obtained is filtered off and washed with diethyl ether. There are obtained 5 g. (88% of theory) N-amino-1,2-dimethylimidazolium p-toluenesulphonate.

10.2 5 g. of the product obtained in 10.1 are heated with 5.4 g. sodium acetate and 125 ml. acetic anhydride for 1 hour at a bath temperature of 140° C. The reaction mixture is evaporated in a vacuum and the residue is taken up in water. The pH value is adjusted to 9 to 10 and extracted with methylene chloride. The organic phase is dried and evaporated. This residue is chromatographed on silica gel with ethyl acetate. There is obtained 0.45 g. (11% of theory) 3-acetyl-2,4-dimethylpyrazolo[1,5-a]-imidazole; m.p. 165°–167° C.

10.3 The compound obtained in 10 is nitrosated analogously to Example 4.3.1. There is obtained 0.35 g. (94% of theory) of the corresponding nitroso compound; m.p. 179°–183° C. This is dissolved in 100 ml. dilute aqueous sodium bicarbonate solution and reduced with sodium dithionite. The reaction mixture is evaporated and digested with ethanol. The ethanol solution is evaporated and the product is precipitated out by the addition of ethereal hydrochloric acid. There is obtained 0.3 g. (80% of theory) of the amino compound; m.p. 199°–204° C. (decomp.). TLC (silica gel, ethyl acetate/acetone/glacial acetic acid/water 50:25:12.5:12.5 v/v/v/v):$R_f$=0.3

10.4 Analogously to Example 4.3.2, the above-obtained amino compound is reacted with potassium ferricyanide and phenol and the coloured material obtained is reduced analogously to Example 4.3.3. $R_f$ of the leuko coloured material obtained: silica gel, toluene/ethyl acetate/methanol 2:1:1 v/v/v=0.5.

10.5 0.46 g. of the above-obtained leuko coloured material is dissolved in 40 ml. methylene chloride and, while cooling with ice, mixed first with 0.65 ml. diisopropylethylamine and then dropwise with 0.51 ml. trifluoroacetic acid anhydride. After 1 hour, there are again successively added thereto 0.35 ml. diisopropylethylamine and 0.25 ml. trifluoroacetic acid anhydride. After stirring for 30 minutes, the reaction mixture is evaporated and the residue is chromatographed over silica gel with methylene chloride/ethyl acetate (1:1 v/v). There is obtained 0.4 g. N-(2,4-dimethylpyrazolo[1,5-a]imidazol-3-yl)-N-( 4-hydroxyphenyl)-trifluoroacetamide.

$R_f$=0.3 (silica gel, methylene chloride/ethyl acetate 1:1 v/v).

10.6 The above-obtained phenol derivative is glycosidated analogously to Example 1.2 with 2-acetamido-3,4,6-tri-O-acetyl-2-deoxy-α-D-glucosyl chloride. For the splitting off of the protective groups, including the trifluoroacetyl radical, the product purified by chromatography on silica gel (methylene chloride/ethyl acetate 1:1 v/v) is dissolved in methanol and the solution is mixed with a large excess of anhydrous sodium carbonate. The mixture is stirred for 1.5 hours at 45° C., the salts are filtered off with suction, the residue is washed with some methanol and the filtrate is concentrated to about 20 ml. This solution is applied to a column containing the adsorber resin HP 20SS (Mitsubishi) and eluted with a stepped gradient of methanol/water (1:9 to 1:1 v/v). There is obtained the title compound; m.p. 112°–115° C. (decomp.). $R_f$=0.2 (silica gel, toluene/ethyl acetate/methanol 1:1:1 v/v/v).

EXAMPLE 11

4-((2,4-Dimethylpyrazolo[1,5-a]-imidazol-3-yl)-N-trifluoroacetyl)-amino)-phenyl-2-acetamido-2-deoxy-β-D-glucopyranoside

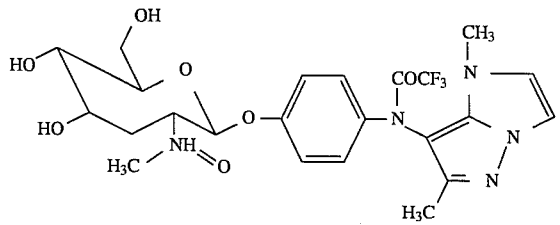

When the splitting off of the protective group of the glycoside obtained in Example 10.6 is carried out with sodium bicarbonate in methanol analogously to Example 1.3, then only the acetyl radicals are split off and, after chromatographic purification analogously to Example 10.6, there is obtained the title compound; m.p. 223°–226° C. (decomp). $R_f$=0.21 (silica gel, toluene/ethyl acetate/methanol 1:1:1 v/v/v).

EXAMPLE 12

Analogously to Example 10.5 and 10.6, starting from the appropriate leuko coloured materials and 2-acetamido-3,4,6-tri-O-acetyl-2-deoxy-α-D-glucosyl chloride, there are obtained the compounds set out in the following Table 2:

TABLE 2

| No. | structure | m.p. °C. | $R_f$ | coloured material component prepn. see |
|---|---|---|---|---|
| 12 a | 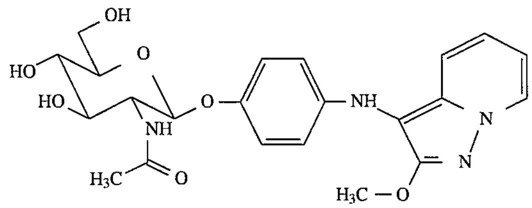 | 198 | 0.43[2] | 12.1. |
| 12 b | 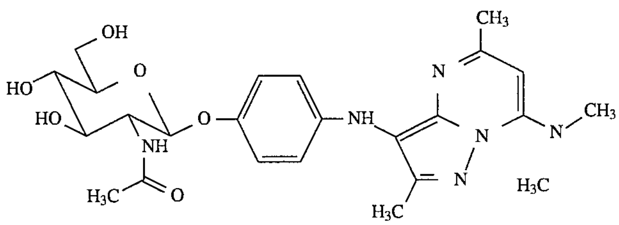 | 173 | 0.24[2] | 12.2. |
| 12 c | 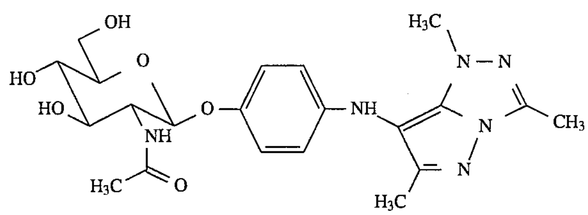 | 220 (decomp.) | 0.31[2] | 12.3. |
| 12 d | 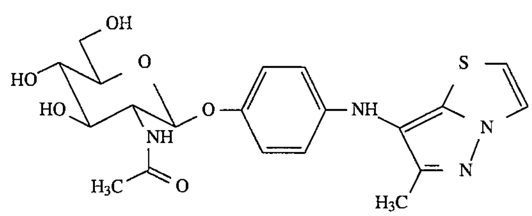 | 193 | 0.39[2] | 12.4. |
| 12 e | 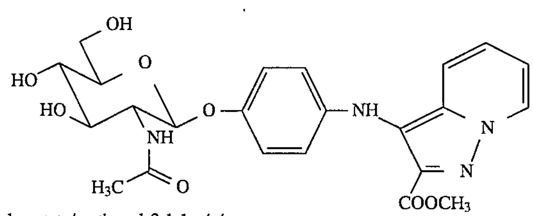 | 228 | 0.37[2] | 12.5. |
| 12 f | 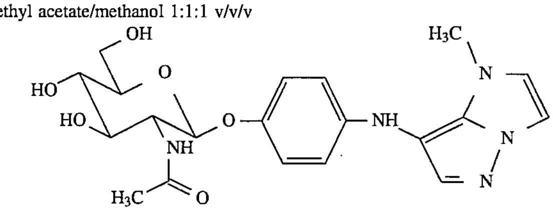 | 148 (decomp.) | 0.17[2] | 12.6. |
| 12 g | 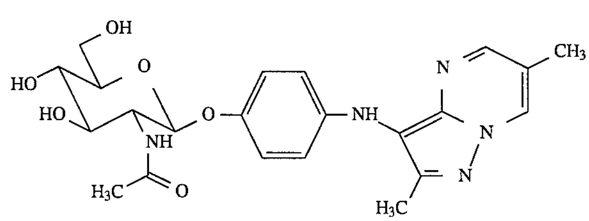 | 248 | 0.26[2] | 12.7. |

[1] silica gel, toluene/ethyl acetate/methanol 2:1:1 v/v/v
[2] silica gel, toluene/ethyl acetate/methanol 1:1:1 v/v/v TABLE 2-continued

| No. | structure | m.p. °C. | $R_f$ | coloured material component prepn. see |
|---|---|---|---|---|
| 12 h | 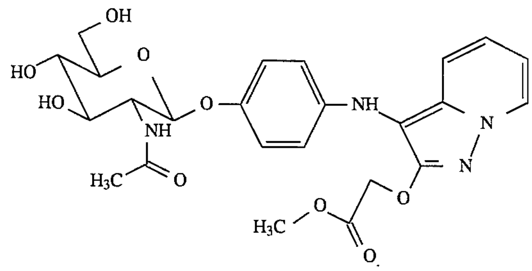 | 188–199 (decomp.) | 0.4[2)] | 12.8. |
| 12 i | 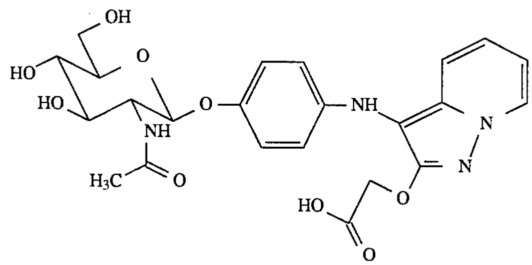 | 251–254 (decomp.) | 0.4[3)] | 12.8. |
| 12 j | 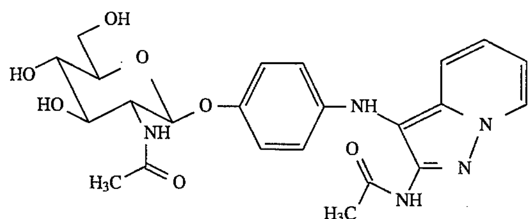 | 271–273 (decomp.) | 0.3[2)] | 12.9. |
| 12 k | 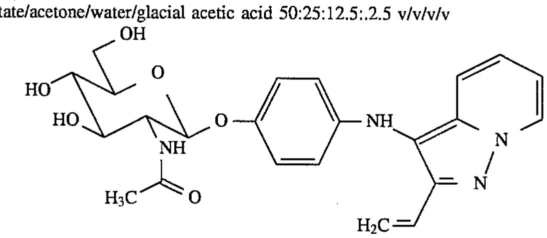 | 227–231 (decomp.) | 0.35[2)] | 12.10. |
| 12 l | 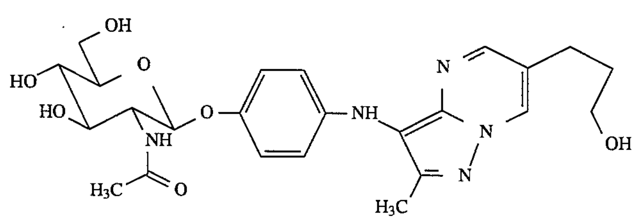 | 188 | 0.43[4)] | 12.11. |

[1)] silica gel, toluene/ethyl acetate/methanol, 2:1:1 v/v/v
[2)] silica gel, toluene/ethyl acetate/methanol, 1:1:1 v/v/v
[3)] silica gel, ethyl acetate/acetone/water/glacial acetic acid 50:25:12.5:.2.5 v/v/v/v TABLE 2-continued

| No. | structure | m.p. °C. | $R_f$ | coloured material component prepn. see |
|---|---|---|---|---|
| 12 m | 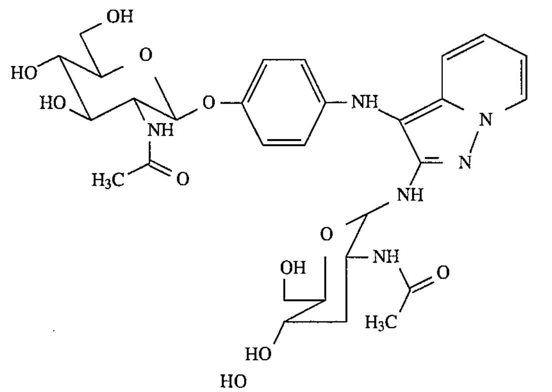 | 214–216 (decomp.) | 0.3[3)] | 12.12. |
| 12 n | 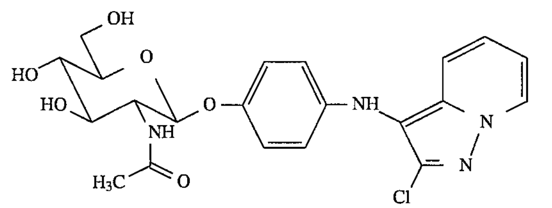 | 185–187 (decomp.) | 0.4[2)] | 12.13. |
| 12 o | 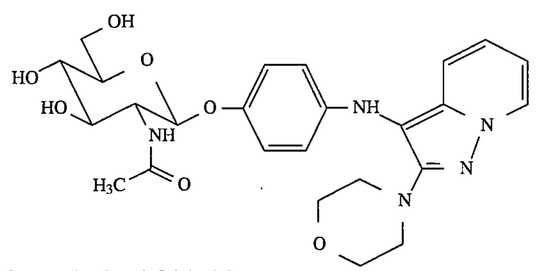 | 270–273 (decomp.) | 0.4[2)] | 12.14. |
| 12 p | 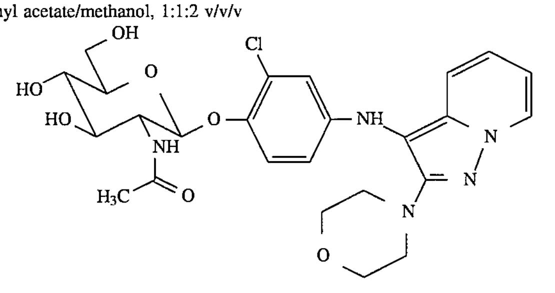 | 258–260 (decomp.) | 0.45[2)] | 12.14. |
| 12 q | 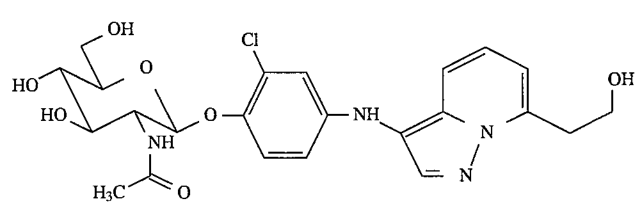 | 239 | 0.34[2)] | 12.15. |

[1)] silica gel, toluene/ethyl acetate/methanol, 2:1:1 v/v/v
[2)] silica gel, toluene/ethyl acetate/methanol, 1:1:1 v/v/v
[3)] silica gel, ethyl acetate/methanol, 1:1 v/v
[4)] silica gel, toluene/ethyl acetate/methanol, 1:1:2 v/v/v TABLE 2-continued

| No. | structure | m.p. °C. | $R_f$ | coloured material component prepn. see |
|---|---|---|---|---|
| 12 r | 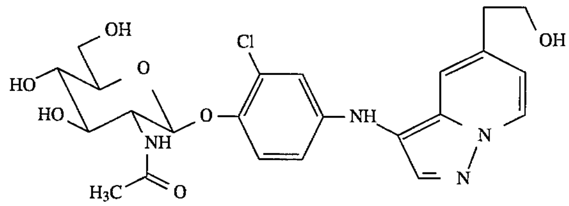 | 220 | $0.27^{2)}$ | 12.16. |
| 12 s | 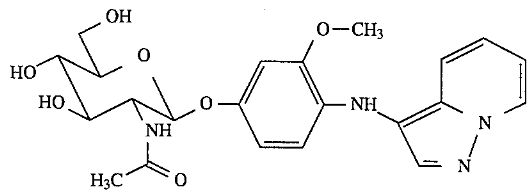 | 140 (decomp.) | $0.38^{2)}$ | 12.17. |
| 12 t | 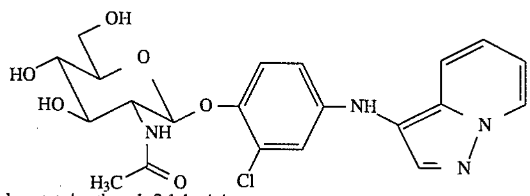 | 196–200 (decomp.) | $0.4^{2)}$ | 12.17. |
| 12 u | 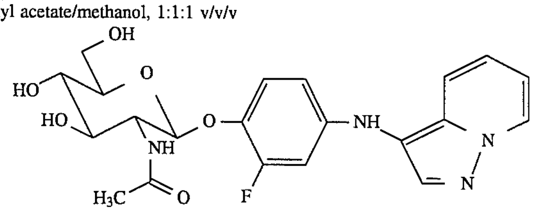 | 221–224 (decomp.) | $0.4^{2)}$ | 12.17. |
| 12 v | 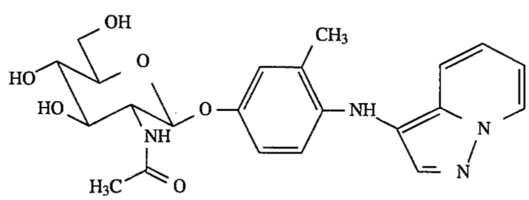 | 150 (decomp.) | $0.39^{2)}$ | 12.17. |
| 12 w | 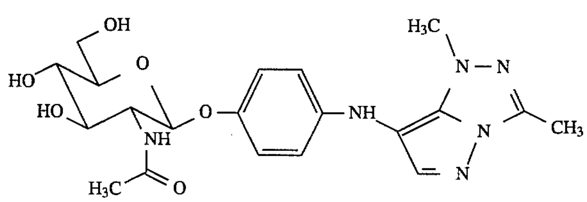 | 154 | $0.30^{2)}$ | 12.18. |
| 12 x | 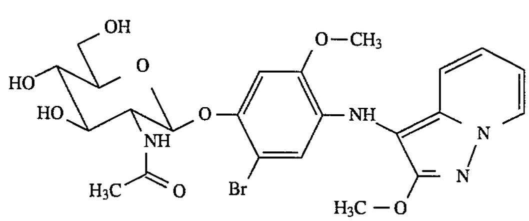 | 184–185 | $0.54^{2)}$ | 12.19. |

[1)] silica gel, toluene/ethyl acetate/methanol, 2:1:1 v/v/v
[2)] silica gel, toluene/ethyl acetate/methanol, 1:1:1 v/v/v TABLE 2-continued

| No. | structure | m.p. °C. | $R_f$ | coloured material component prepn. see |
|---|---|---|---|---|
| 12 y | 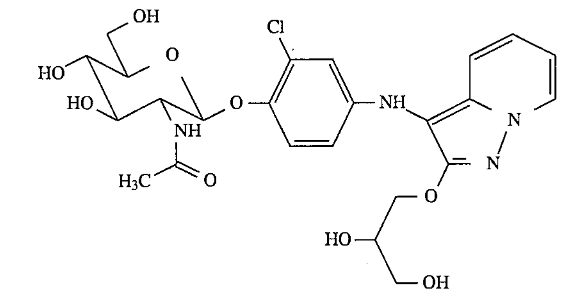 | 215–220 (decomp.) | 0.25[2)] | 12.20. |
| 12 z | 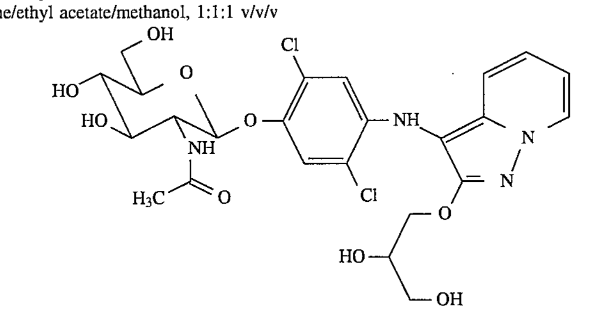 | 214–216 (decomp.) | 0.3[2)] | 12.20.3. |
| 12 aa | 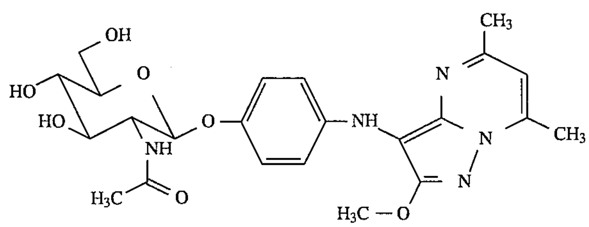 | 162 | 0.37[2)] | 12.21. |

[1)]silica gel, toluene/,ethyl acetate/methanol, 2:1:1 v/v/v
[2)]silica gel, toluene/ethyl acetate/methanol, 1:1:1 v/v/v Preparation of leuko coloured material components 12.1  4-Hydroxyphenyl-2-methoxypyrazolo/[1,5-a]pyridin-3-yl-amine 12.1.1  3-Amino-2-methoxy-pyrazolo[1,5-a]pyridine hydrochloride 2-Hydroxypyrazolo[1,5-a]pyridine (I). After a mixture of ethyl 2-pyridylacetate (3.00 g), HAS (0.60 g) and water (3 ml) was stirred at room temperature for 30 h, it was extracted with $CH_2CL_2$. The aqueous layer was made alkaline with 10% $Na_2CO_3$ to pH 9 and was extracted with $CH_2CL_2$. The organic extracts were combined, and after drying over $MgSO_4$ the solvent was evaporated. The residual oil was shaken with $Et_2O$-10% $Na_2CO_3$. After the ether-layer was dried over $MgSO_4$, the solvent was evaporated to give the starting ethyl 2-pyridylacetate (2.11 g, 70.5% yield). The pH of the basic aqueous layer was adjusted to 5 by adding AcOH to precipitate brown powder (0.36 g, 45.9% yield, based upon the consumed starting material). Recrystallization from benzene-hexane gave 2-hydroxypyrazolo[1,5-a]pyridine (0.32 g, 40.7%) mp 127°–128° C., as colorless leaflets. UV $\lambda_{max}^{meOh}$ (log $\epsilon$): 232 (4.59), 280.5 (3.09), 310 (3.10) IR vmax$^{CHCl_3}$ cm$^{-1}$: 3000, 1635, 1535, 1258. Found: C, 62.53; H, 4.48; N, 20.98%. Calcd for $C_7H_6ON_2$: C, 62.68; H, 4.51; N, 20.98%.

2-Methoxypyrazolo[1,5-a]pyridine (V). To a solution of I(134 mg) in MeOH (5 ml) was added an excess solution of $CH_2N_2$ in ether and the mixture was left to stand in an icebox for a day. Evaporation of the solvent gave colorless oil (135 mg) which exhibited a single spot on a TLC plate ($R_f$=0.89, 5% MeOH—$CHCL_3$ silica gel G. F. nach Stahl). Purification by passing a short column of $SiO_2$ gave colorless oil (118 mg, 80.5% yield). UV $\lambda_{max}^{MeOH}$ nm (log $\epsilon$): 234 (4.57), 282 (3.30), 307 (3.31). IR $v_{max}^{CHCl_3}$ cm$^{-1}$: 3000, 1640, 1540, 1360 Found: C, 64.57; H, 5.31; N, 18.71%. Calcd for $C_8H_8ON_2$: C, 64.85; H, 5.44; N, 18.91%.

1.48 g. 2-methoxypyrazolo[1,5-a]pyridine (see Bull. Chem. Soc. Jap., 49, 1980/1976as above) are dissolved, while cooling with ice, in 20 ml. concentrated nitric acid and mixed dropwise with 10.5 ml. fuming nitric acid. The reaction mixture is stirred for 30 minutes in an ice-bath and for 1 hour at ambient temperature. The reaction mixture is poured on to ice, the precipitate obtained is filtered off with suction and washed with water. There is obtained 1 g. (52% of theory) 2-methoxy-3-nitropyrazolo[1,5-a]pyridine; m.p. 213°–216° C.

0.8 g. of the above-obtained nitro compound is suspended in 80 ml. 2N hydrochloric acid and mixed with zinc dust, while stirring vigorously. After several additions of zinc dust, there is obtained, after about 1 hour, a clear solution over a bottom deposit of excess zinc. This is filtered off and the filtrate is adjusted to pH 7 with sodium hydroxide. The mixture is then extracted with ethyl acetate, the organic phase is evaporated and the remaining oil is filtered with ethanol through a short column of silica gel. The eluate is evaporated, the residue is dissolved in diethyl ether and mixed with ethereal hydrochloric acid. The precipitate obtained is filtered off with suction and again recrystallised from isopropanol. There is obtained 0.33 g. (42% of theory) of the title compound (12.1.1); m.p. 238°–241° C. TLV (silica gel, acetone/methylene chloride/glacial acetic acid, 50:45:5 v/v/v): $R_f$=0.6.

12.1.2 Analogously to Example 4.3.2, from the amino compound obtained there is obtained, by oxidative coupling with phenol, the coloured material which is reduced analogously to Example 4.3.3 and then trifluoroacetylated analogously to Example 10.5.

12.2   4-Hydroxyphenyl-2,5-dimethyl-7-dimethylaminopyrazolo[1,5-a]pyrimidin-3-ylamine 12.2.1 3-Amino-2,5-dimethyl-7-dimethylaminopyrazolo [1,5-a]pyrimidine hydrochloride 1.6 g. 2,5-dimethyl-7-hydroxypyrazolo[1,5-a]pyrimidine are heated under reflux for 40 minutes with 16.6 ml. phosphorus oxychloride and 0.8 ml. N,N-dimethylaniline. The excess phosphorus oxychloride is distilled off and the residue is poured on to ice. The mixture is extracted with methylene chloride, the organic phase is washed with an aqueous solution of sodium carbonate, dried and evaporated. The residue is dissolved in 28 ml. ethanol and mixed with 2 g. of a 40% solution of dimethylamine in water. The mixture is stirred for 2.5 hours at ambient temperature, evaporated and the residue is chromatographed over silica gel with ethyl acetate. There is obtained 0.86 g. (46% of theory) 2,5-dimethyl-7-(N,N-dimethylamino)-pyrazolo[1,5-a]pyrimidine which is nitrosated analogously to Example 4.3.1.

The nitroso compound obtained (1 g.) is dissolved in 20 ml. ethanol, mixed with 0.16 g. palladium/carbon and mixed at the boiling temperature with 0.4 ml. hydrazine hydrate. The reaction mixture is further boiled under reflux for 15 minutes, filtered with suction and the filtrate concentrated somewhat. The residue is dissolved in a little ethanol and mixed with ethereal hydrochloric acid in order to precipitate out the hydrochloride. There is obtained 0.8 g. 3-amino-2, 5-dimethyl-7-(dimethylaminopyrazolo[1,5-a]pyrimidine hydrochloride. $R_f$=0.54 (silica gel, chloroform/methanol/ methyl ethyl ketone/glacial acetic acid/water 75:35:25:5:8 v/v/v/v/v).

12.2.2 6.94 g. Phenol are dissolved in 124 ml. pyridine and 743 ml. water. A solution of 11.4 g. of the above-obtained amino compound in 248 ml. water are added thereto. Finally, one mixes with a solution of 0.33 g. peroxidase (from horseradish, Boehringer Mannheim GmbH, Mannheim, Germany) and immediately adds dropwise thereto 11.23 ml. 30% hydrogen peroxide. There are obtained 12.9 g. of blue N-(2,5-dimethyl-6-dimethylaminopyrazolo[1,5-a]pyrimidin-3-yl)-quinonimine. $R_f$=0.43 (silica gel, ethyl acetate/methylene chloride 95:5 v/v). The coloured material is reduced analogously to Example 4.3.3 and trifluoroacetylated analogously to Example 10.5. If the coloured material does not precipitate out, then it is extracted with ethyl acetate. Under certain circumstances, it it is recommended to work up to the leuko coloured material by the addition of sodium dithionite and aqueous sodium carbonate solution analogously to Example 4.3.3.

12.3 4-hydroxyphenyl-2,4,6-trimethylpyrazolo[3,2-c]-s-triazol-3-yl)-amine

Starting from 4-ethoxycarbonyl-3-methylpyrazolo-5-yl-hydrazine (see Chem. Ber., 89, 2552/1956 as above), there is prepared 2,6-dimethyl-4H-pyrazolo[3,2-c]-s-triazole-3-carboxylic acid ethyl ester in the manner described in Example 6 of published Federal Republic of Germany Patent Specification No. A-18 10 462.

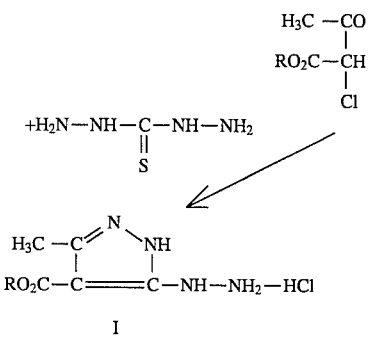

To prepare 4-ethoxycarboxyl-3-methyl-pyrazole-5-yl hydrazine I,

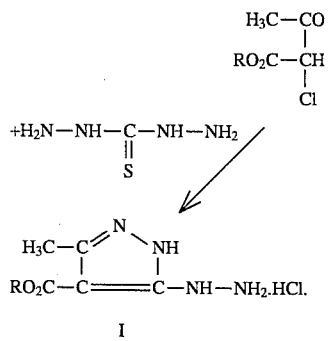

For the synthesis of 4-ethoxy carbonyl-3-methyl-pyrazolo- 5-yl-hydrazine 10.6 g thiocarbohydrazide ($H_2N=NH=CSNHNH_2$) are suspended in 100 ccm of ethanol and 30 ccm hydrochloric acid are added while boiling. Under stirring 16.5 g ethyl α-chloro-acetoacetate dissolved in 20 ccm ethanol are added dropwise within 30 minutes. After cooling a crystal mask of the product separates which can be recrystallized from ethanol.

Summary of Example 6 (DE 1810462)

4-ethoxycarbonyl-3-methylpyrazolo-5-yl-hydrazine was mixed with acetate acid and acetic acid anhydride and heated on a steam bath. After boiling of the reaction mixture it was poured into water. The acetic hydrazide which crystallizes from the solution was isolated. This compound together with dry benzene and phosphoryloxychloride was heated under reflux. After the benzene was removed by distillation, the oil residue was mixed with water and the mixture extracted with ethylacetate. Evaporation of the ethylacetate yields 2,6-dimethyl-4H-pyrazolo-[3,2-c]-s-triazole-3-carboxylic acid ethyl ester which can be purified by recrystallization from ethanol.

0.4 g. of this ester is dissolved in 15 ml. dry dimethylformamide and mixed with 0.46 g. p-toluene-sulphonic acid methyl ester. Into this mixture is introduced portionwise 0.11 g. 55% sodium hydride, followed by stirring for 1 hour at ambient temperature. The reaction mixture is poured on to ice and 5 g. sodium chloride are added thereto. The reaction mixture is then extracted several times with ethyl acetate and the extract is dried and evaporated. The remaining oil is purified by chromatography on silica gel with ethyl acetate/ ligroin as elution agent.

As intermediate, there is thus obtained 2,4,6-trimethylpyrazolo[3,2-c]-s-triazole-3-carboxylic acid ethyl ester ($R_f$=0.52; silica gel, ethyl acetate/ligroin 1:1 v/v), which is saponified and simultaneously decarboxylated by boiling with concentrated hydrochloric acid. There is obtained 2,4,6-trimethylpyrazolo[3,2-c]-s-triazole ($R_f$=0.24; silica gel, ethyl acetate/ligroin 1:1 v/v) as pale yellowish oil which, after some time, crystallises.

1.83 g. of this heterocyclic compound is dissolved in 40 ml. glacial acetic acid and mixed with 1 g. sodium acetate and 3.3 g. p-methoxybenzenediazonium tetrafluoroborate. The reaction mixture is stirred at 40° C. and after, after 3 hours, 0.2 g. sodium acetate and 0.66 g. of the diazonium salt are again added thereto for completion of the reaction. After a further 3 hours at 40° C., the reaction mixture is poured on to ice. It is then extracted with ethyl acetate and the crude product obtained is purified by chromatography on silica gel with ethyl acetate/ligroin (1:1 v/v). There are obtained 3.7 g. of the lemon yellow azo compound.

3.1 g. of the azo compound are dissolved in 50 ml. glacial acetic acid and, with gentle cooling, mixed with 5 g. zinc powder. After 1 hour, the reaction mixture is filtered and the filtrate is evaporated. For purification, the crude product is dissolved in dioxan and mixed with 3.9 g. tert.-butyl dicarbonate. After a reaction period of 2 hours, the reaction mixture is evaporated and the residue is chromatographed on silica gel with ligroin/acetone (7:3 v/v). There is obtained 1.5 g. of the corresponding N-tert.-butoxycarbonyl compound which, for splitting off the amino protective group, is dissolved in 25 ml. ethanolic hydrochloric acid. After 1 hour, the solution is evaporated at ambient temperature and the residue is recrystallized from methanol/diethyl ether. There is obtained 1.6 g. of the title compound (12.2.1); m.p. 240° C. $R_f$=0.5 (silica gel; ethyl acetate/acetone/glacial acetic acid/water 50:25:12.5:12,5 v/v/v/v).

12.3.2 The above-obtained amino compound is coupled with phenol to give the coloured material analogously to Examples 4.3.2 and 4.3.3, reduced and the leuko coloured material trifluoroacetylated analogously to Example 10.5.

12.4 4-Hydroxy-2-methylpyrazolo[3,2-b]thiazol-3-ylamine

The leuko coloured material is obtained analogously to Examples 4.3.1, 4.3.2 and 4.3.3, starting from 3-acetyl-2-methylpyrazolo[3,2-b]thiazole (see Chem. Pharm. Bull., 22, 482/1974) and trifluoroacetylated analogously to Example 10.5.

To form 3-acetyl-2-methyl pyrazolo[3,2-]thiazole, the n-amino compound as shown was cyclized by treatment with acetic anhydride and anhydrous sodium acetate to the pyrazolo derivative (42%, mp 130°–131° C.)

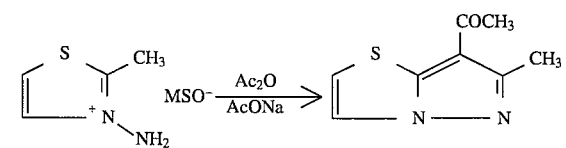

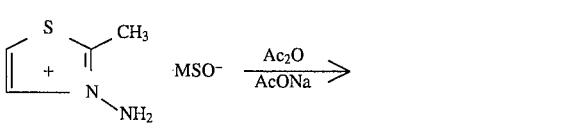

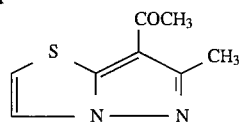

12.5 4-Hydroxyphenyl-2-carboxylic acid methyl ester pyrazolo[1,5-a]pyridin-3-ylamine Starting from 2-pyrazolo[1,5-a]pyridine-carboxylic acid ethyl ester (compound 6 of the scheme below)

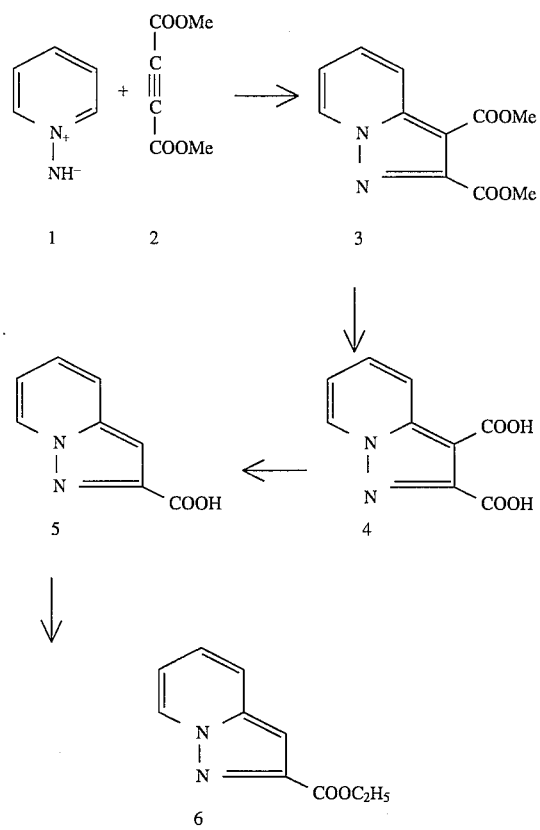

(see J. Het. Chem., 18, 1149/1981), the leuko coloured material component is obtained analogously to Example 4.3.1 (nitrosation), 12.1 (reduction with zinc/hydrochloric acid), 12.2.2 (oxidative coupling with phenol) and 4.3.3 (reduction to the leuko coloured material, the leuko coloured material then being trifluoroacetylated analogously to Example 10.5. In the case of the splitting off of the acetyl protective groups in the least reaction step, the ethyl ester is transesterified to give the methyl ester.

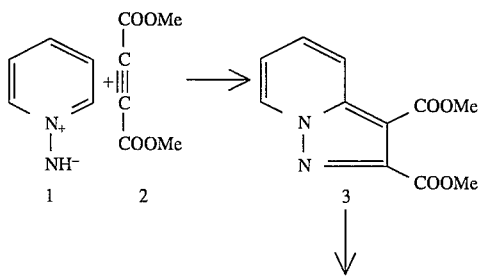

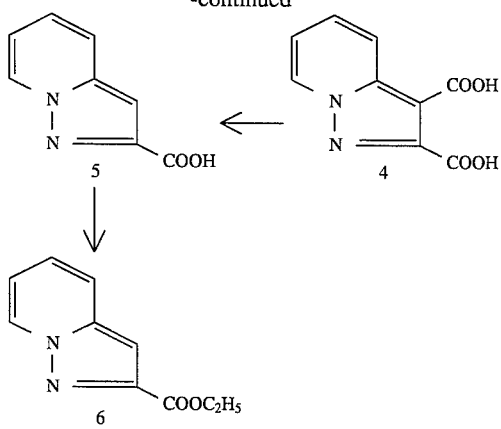

To prepare compound 6, a solution of 8.1 g pyrazolo[1,5-a]pyridine-2-carboxylic acid (5), 50 ml of absolute ethanol and 0.2 g of p-toluenesulfonic acid monohydrate was refluxed in a flask fitted with a soxhlet extractor containing 50 g of 3 angstrom molecular sieves (Linde). The solution was refluxed 24 hours, cooled and diluted with 200 ml of water. The solution was then extracted three times with 100 ml portions of chloroform and the chloroform extracts washed successively with 200 ml of water, 200 ml of 1N sodium bicarbonate solution, 200 ml of water and 200 ml of a mixture of 150 ml of saturated salt solution and 50 ml of water. The chloroform solution was then dried over sodium sulfate and the solvent removed to give 11.3 g of an orange oil. The oil was distilled under reduced pressure and the fraction boiling at 80°–90° (0.05 torr) was collected. This colorless oil crystallized on standing to give 7.26 g (76%) of colorless product, mp 40°–43°; nmr (deutoeriochloroform): $\delta 1.43$ (t, 3, J=3 Hz, $CH_3$), 4.50 (q, 2, J=3.5 Hz, $CH_2$), 7.10 (m, 2, $C_4$—H+$C_3$—H), 7.12 (s, 1, $C_6$—H), 7.64 (d, 1, J=4 Hz, $C_2$—H), 8.59 (d, 1, J=3.5 Hz, $C_5$—H); ir (chloroform); 1720 (C=O), 1636 (C=N).

12.6  4-Hydroxy-4-methylpyrazolo[1,5-a]imidazol-3-ylamine 12.6.1  3-Amino-4-methylpyrazolo[1,5-a]imidazole hydrochloride Synthesis of ethoxymethylenecyanoacetate from organikum p 476:

0.75 mole of ortho-formic acid-triethylester, 0.5 mole of 2-cyano-acetic acid-ethylester and 1 mole of acetic acid anhydride are mixed, subsequently heated for 1 hour to 140° C. and additionally for 1 hour to 150° C. Vacuum distillation leads to a product which distills between 173° C. and 174° C. at 15 Torr.

Analogously to the process described in "Organikum" (pub. VEB Deutscher Verlag der Wissenschaften, Berlin) on pages 514–515, 65 g. ethyl ethoxymethylenecyanoacetate is reacted with 55 g. 2,2-diethoxyethylhydrazine to give 100.2 g. 5-amino-1-(2,2-diethoxyethyl)-pyrazole-4-carboxylic acid which is dissolved in 4 liters ethanol and mixed with 2 liters 20% sulphuric acid. The reaction mixture is heated under reflux for 3 hours and neutralised by the addition of solid sodium bicarbonate. The precipitated salt is filtered off and the filtrate is evaporated. The residue is extracted several times with boiling methylene chloride. The filtrates are combined and evaporated to give 58.2 g. (86% of theory) pyrazolo[1,5-a]imidazole-3-carboxylic acid ethyl ester; m.p. 126°–127° C.; $R_f$=0.64 (silica gel, ethyl acetate).

18.7 g. of the above-obtained carboxylic acid ester are dissolved in 190 ml. dimethylformamide and mixed with 17 g. p-toluenesulphonic acid methyl ester. While stirring, 3.98 g. 55% sodium hydride are introduced portionwise. The reaction mixture is stirred for 30 minutes at ambient temperature and extracted with ethyl acetate. There are obtained 21.9 g. (100% of theory) 4-methylpyrazolo[1,5-a]imidazole-3-carboxylic acid ethyl ester which is saponified by boiling with 600 ml. concentrated hydrochloric acid. At the same time, the resultant carboxylic acid is decarboxylated to give 16.7 g. (83% of theor) 4-methylpyrazolo[1,5-a]imidazole dihydrochloride; $R_f$=0.39 (silica gel, methylene chloride with 5methanol).

12.8 g. Aniline was diazotised in a solution of 12.9 ml concentrated sulphuric acid in 64 ml. water by the addition of a solution of 9.5 g. sodium nitrite in 42 ml. water. The solution is adjusted to pH 5 by the addition of sodium hydroxide and mixed dropwise at 5° to 10° C. with as a solution of 16.5 g. of the above-obtained 4-methylpyrazolo [1,5-a]imidazole in 165 ml. water and 14 ml. glacial acetic acid. The reaction mixture is stirred for 1 hour at 5° to 10° C. and for 3 hours at ambient temperature and then the precipitate obtained is filtered off with suction. There are obtained 12 g. 4-methyl-3-phenylazopyrazolo[1,5-a]imidazole which is reduced with sodium dithionite analogously to Example 12.3 and purified. There are obtained 3.3 g. 3-amino-4-methyl-pyrazolo[1,5-a]imidazole hydrochloride; m.p. above 210° C. (decomp.); $R_f$=0.23 (silica gel, ethyl acetate/acetone/glacial acetic acid/water 50:25:12.5:12.5 v/v/v/v).

12.6.2 The further working up to give the leuko coloured material takes place analogously to Example 12.3.2.

12.7 4-Hydroxyphenyl-2,6-dimethylpyrazolo[1,5-a]pyrimidin-3-ylamine 12.7.1 3-Amino-2,6-dimethylpyrazolo[1,5-a]pyridimine hydrochloride

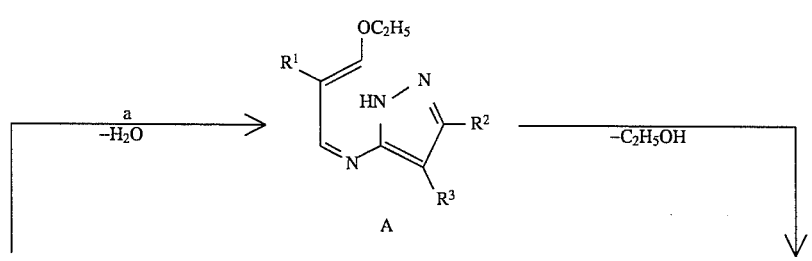

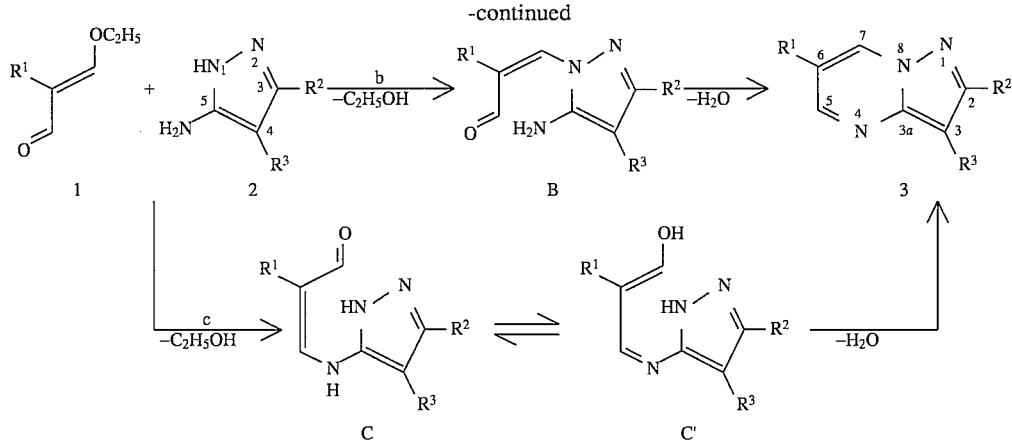

$R_1R_2=CH_3$

Starting Material=3

$R_3=NO_2$, m. P272.5

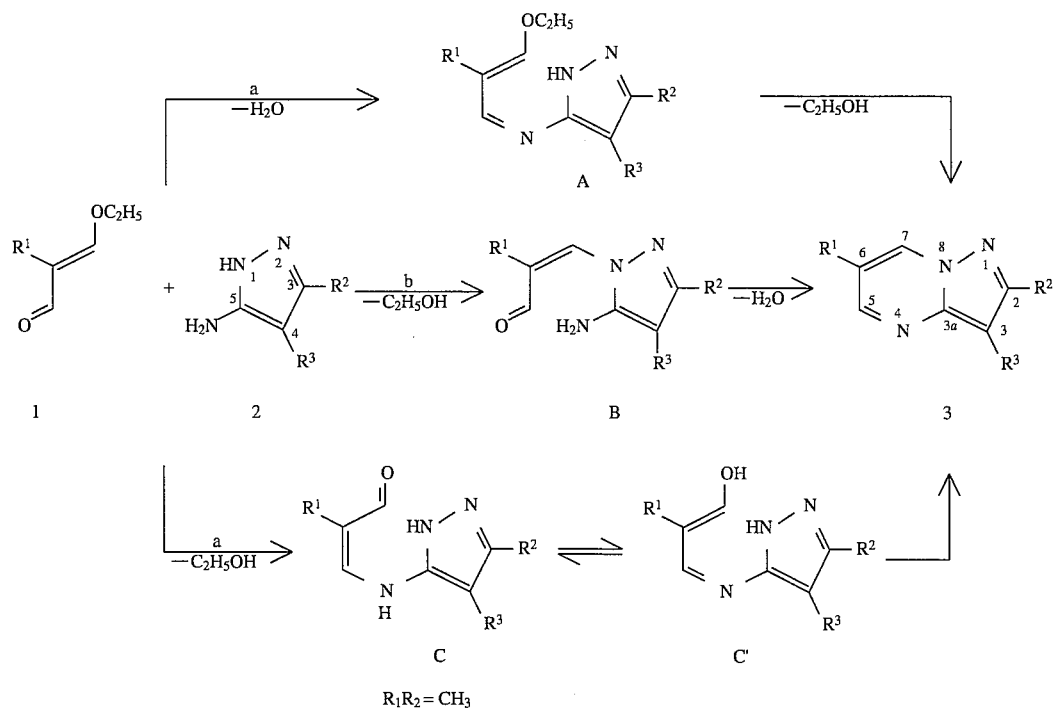

$R_1R_2 = CH_3$ via method a, b or c
pyrazolo[1,5a]pyrimidine
General Procedure

The 5-amino-1H-pyrazol (2) (0,06) mol) and 2-allyl-3-ethoxy-acrolin (1) (0,06 mol) in concentration acetic acid (70 ml) are refluxed for 3 hours. After cooling the mixture is treated as follows:

Variant A: The reaction solution is concentrated until dryness under reduced pressure, the residue is dried in a dessicator over solid sodium hydroxide and crystallized in methanol.

Variant B: After concentrating and drying of the reaction product, it is distilled in a vacuum over sodium hydroxide.

Variant C: After concentrating and drying of the reaction product it is sublimed in high vacuum over sodium hydroxide.

Variant D: The product crystallizes. It is filtered, dried and purified by soxhlet-extraction with methanol.

3.2 g. 2,6-Dimethyl-3-nitropyrazolo[1,5-a]pyrimidine (see Synthesis, Communications Page 673/1982) are dissolved in 320 ml. ethanol and mixed with 320 ml. 5% sodium bicarbonate solution in water. To this mixture are added portionwise, while stirring and cooling, 14.2 g. sodium dithionite until the thin layer chromatogram indicates the absence of starting material. The reaction mixture is concentrated somewhat and extracted three times with ethyl acetate. The organic phase is dried and evaporated. The residue is dissolved in a little ethanol and mixed with an equimolar amount of hydrogen chloride in diethyl ether. The precipitated crystals are filtered off with suction. There are obtained 2.9 g. (80% of theory) of the title compound (12.7.1); m.p. 224° C. (decomp.). TLC (silica gel, chloroform/methanol/methyl ethyl ketone/glacial acetic acid/water 75:35:25:5:8 v/v/v/v/v): $R_f$=0.73.

12.7.2 The leuko coloured material is obtained by oxidative coupling with phenol analogously to Example 4.3.2 and reduction analogously to Example 4.3.3, followed by trifluoroacetylation analogously to Example 10.5.

12.8 4-Hydroxyphenyl-2-ethoxycarbonylmethoxypyrazolo[1,5-a]-pyridin-3-ylamine

Analogously to Example 12.1, starting from 2-ethoxycarbonylmethoxypyrazolo[1,5-a]pyridine, prepared analogously to the 2-methoxy compound (see Bull. Chem. Soc. Jap., 49, 1980/1976) by alkylation of the 2-hydroxyheterocyclic compound, there is obtained the N-trifluoroacetylated leuko coloured material. In the case of splitting off the acetyl protective groups from the last reaction step, a part of the carboxylic acid ester is saponified. The ester and acid can be smoothly separated by chromatography over the adsorber resin HP 20SS (Mitsubishi) (elution agent: methanol/water).

12.9 4-Hydroxyphenyl-2-acetaminopyrazolo[1,5-a]pyridin- 3-ylamine

To obtain starting material:

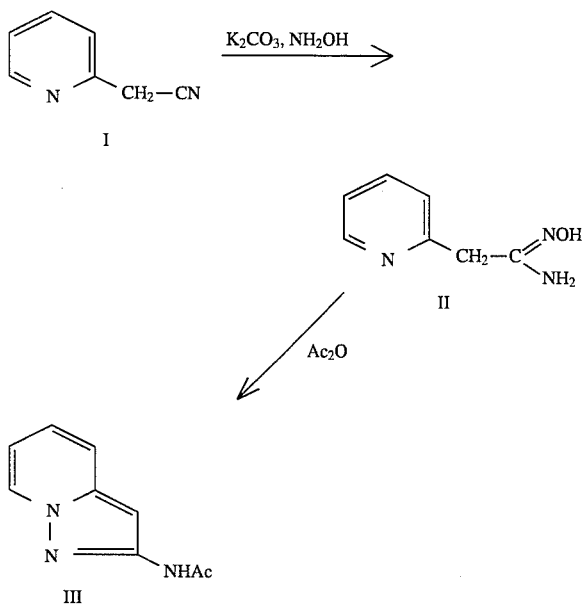

Compound II, prepared from pyridine-2-acetonitrile (I) and hydroxylamine, was treated with excess acetic anhydride at 100° C. for 30 minutes and the reaction products were separated by chromatography on alumina.

The 2-acetamidopyrazolo[1,5-a]pyridine (III) was obtained in 29.7% yield.

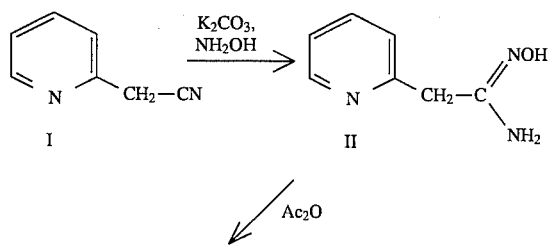

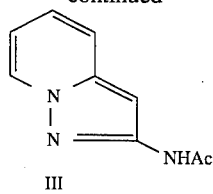

4 g. 2-Actamidopyrazolo[1,5-a]pyridine (see Chem. Pharm. Bull., 21, 2146/1973) are nitrosated analogously to Example 4.3.1. The nitroso compound is reduced analogously to Example 5.1 with palladium-carbon/hydrazine hydrate. There are obtained 3.9 g. (67% of theory) 2-acetamido-3-aminopyrazolo[1,5-a]pyridine hydrochloride; m.p. 255°–259° C., (decomp.). $R_f$=0.5 (silica gel, ethyl acetate/acetone/glacial acetic acid/water 50:25:12.5:12.5 v/v/v/v).

The amino compound is coupled with phenol analogously to Example 4.3.2 to give the coloured material which is reduced analogously to Example 4.3.3 and N-trifluoroacetylated analogously to Example 10.5.

12.10 4-Hydroxyphenyl-2-vinylpyrazolo[1,5-a[pyridin-3-ylamine 25 g. R,S-3-acetyl-2-(1-hydroxyethyl)-pyrazolo[1,5-a]-pyridine (from Example 5.1) are mixed with 50 ml. concentrated sulphuric acid and heated for 2 hours at a bath temperature of 95° C. The reaction mixture is poured on to a large amount of ice, rendered alkaline with sodium hydroxide and extracted with ethyl acetate. The crude product is chromatographed over silica gel with ligroin/ethyl acetate (95:5 to 90;10 v/v). There are obtained 3.4 g. 2-vinylpyrazolo[1,5-a]pyridine ($R_f$=0.6; silica gel, ligroin/ethyl acetate 3:1 v/v), which is reacted with phenyl diazonium salt analogously to Example 12.3.1, reduced and purified. There is thus obtained the corresponding aminopyrazole. $R_f$=0.65; silica gel, ligroin/acetone/glacial acetic acid 50:45:5 v/v/v).

The amino compound is coupled with phenol analogously to Example 12.2.2 to give the coloured material which is reduced analogously to Example 4.3.3 and N-trifluoroacetylated analogously to Example 10.5.

12.11 4-Hydroxyphenyl-6-(3-acetoxypropyl)-2-methylpyrazolo[1,5-a]pyrimidin-5-ylamine 12.11.1 6-(3-Acetoxypropyl)-2-methylpyrazolo[1,5-a]pyrimidine 6-(3-Acetoxypropyl) pyrazolo[1,5-a]pyrimidine general procedure. The 5-amino- 1-H-pyrazol 2 (0,05 mol) and 5-formyl-3,4-dihydro-2H-pyrane 4 (5,6 g; 0,05 mol) are refluxed for one hour in concentrated acetic acid. The reaction scheme is shown above in example 12.7.1. Here compound 3 $R_1$=ACO propyl, $R_2$=$CH_3$ and $R_3$=$NO_2$. After cooling the mixture is treated as follows:

Variant A: If the product crystallizes, it is sucked off, washed with ethanol and dried under reduced pressure.

Variant B: If the product doesn't crystallize the mixture is evaporated to dryness and the residue is kept over sodium hydroxide in a desiccator for two weeks. If the residue crystallizes, the crystals are crystallized in ethanol.

Variant C: If the residue doesn't crystallize according to variant B, it is distilled under reduced pressure.

Analogously to Example 12.7.1, by the reduction of 6-(3-acetoxypropyl)-2-methyl-3-nitropyrazolo[1,5-a]pyrimidine (see Synthesis, communications 673/1982), there is obtained the title compound (12.11.1). $R_f$=0.21 (silica gel, methylene chloride/methanol 90:1 v/v).

12.11.2 The amino compound is coupled with phenol analogously to Example 4.3.2 to give the coloured material which is reduced analogously to Example 4.3.3 and N-trifluoroacetylated analogously to Example 10.5.

12.12 4-Hydroxyphenyl-2,3-diaminopyrazolo[1,5-a]pyridin-3-ylamine

The 2-acetaminopyrazolo-[1,5-a]pyridine starting material of example 12.9 was subjected to acid hydrolysis to yield the 2-amino derivative:

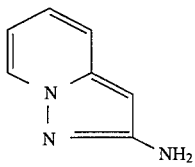

2-aminopyrazolo[1,5-a]pyridine.

This is the starting material for examples 12.13.1 and 12.14.1 as well

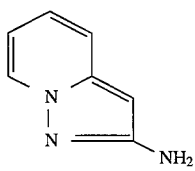

2.66 g. 2-Aminopyrazolo[1,5-a]pyridine (see Chem. Pharm. Bull., 21, 2146/1973) are reacted with p-methoxybenzenediazonium salt analogously to Example 12.3.1, the resultant azo compound is reduced with sodium dithionite and the crude product obtained is purified to give 2,3-diaminopyrazolo[1,5-a]pyridine; m.p. 190° C.; $R_f$=0.6 (silica gel, ligroin/acetone/glacial acetic acid 60:40:1 v/v/v).

The diamino compound is coupled with phenol analogously to Example 4.3.2 to give the coloured material which is reduced analogously to Example 4.3.3 and N-trifluoroacetylated analogously to Example 10.5.

In the case of subsequent glycosidation, the leuko coloured material is glycosidated not only on the phenolic hydroxyl group but also on the 2-amino group.

12.13 4-Hydroxyphenyl-2-chloropyrazolo[1,5-a]pyridin-3-ylamine 12.13.1 3-Amino-2-chloropyrazolo[1,5-a]pyridine hydrochloride 2-Aminopyrazolo[1,5-a]pyridine (see Chem. Pharm. Bull., 21, 2146/1973) is reacted with p-methoxybenzenediazonium salt analogously to Example 12.3.1. 0.53 g. of the 3-azo compound obtained is suspended in 10 ml. 6N hydrochloric acid and mixed at +5° C., while stirring, with a solution of 104 mg. sodium nitrite in 0.2 ml. water. After 30 minutes, a cold solution of 198 mg. cuprous chloride in 6 ml. 6N hydrochloric acid is added thereto and the reaction mixture is stirred for 40 hours at ambient temperature. The reaction mixture is mixed with water and extracted 3 or 4 times with ethyl acetate. After purification of the crude product by chromatography over silica gel (elution agent: ethyl acetate/ligroin 1:1 v/v), there are obtained 320 mg. 2-chloro-3-(p-methoxyphenylazo)pyrazolo[1,5-a]pyridine ($R_f$=0.65; silica gel, ethyl acetate/ligroin 1:1 v/v) which is reduced with sodium dithionite analogously to Example 12.3.1. There is obtained the title compound; m.p. 249°–251° C. (decomp.); $R_f$=0.2 (silica gel, ethyl acetate/ligroin 1:1 v/v).

12.13.2 The amino compound is coupled with phenol analogously to Example 4.3.2 to give the colored material which is reduced analogously to Example 4.3.3 and N-trifluoroacetylated analogously to Example 10.5.

12.14 4-Hydroxyphenyl-2-morpholinopyrazolo[1,5-a]pyridin- 3-ylamine 12.14.1 3-Amino-2-morpholinopyrazolo[1,5-a]-pyridine hydrochloride 2-Aminopyrazolo[1,5-a]pyridine (see Chem. Pharm. Bull., 21, 2146/1973) is reacted with p-methoxybenzene diazonium salt analogously to Example 12.3.1. 4 g. of the azo compound are dissolved in 100 ml. dimethylformamide and mixed with 5.33 g. β,β'-dibromodiethyl ether and 2 g. sodium hydride (55%). The reaction mixture is stirred for 1.5 hours at ambient temperature and water and ethyl acetate added thereto. The organic phase is separated off and the aqueous phase is again extracted with ethyl acetate. The combined organic phases are dried and evaporated. The residue obtained is triturated with hexane. There are obtained 4.75 g. 3-(4-methoxyphenyl)-azo-2-morpholinopyrazolo[1,5-a]pyridine; $R_f$=0.7 (silica gel, ethyl acetate/methylene chloride 1:1 v/v).

The azo compound is reduced with zinc and glacial acetic acid analogously to Example 12.3.1, purified and the tert.-butoxycarbonyl radical split off with hydrochloric acid in ethanol. There are obtained 2.43 g. of the title compound (12.14.1); m.p. 105°–110° C. (decomp.). $R_f$=0.4 (silica gel, ethyl acetate).

12.14.2 The amino compound is coupled with phenol analogously to Example 4.3.2 to give the coloured material which is reduced analogously to Example 4.3.3 and trifluoroacetylated analogously to Example 10.5.

Analogously thereto, by coupling with p-chlorophenol, there is obtained the corresponding halogen-containing leuko coloured material 3-chloro-4-hydroxyphenyl- 2-morpholinopyrazolo[1,5-a]pyridin-3-ylamine.

12.15  3-Chloro-4-hydroxyphenyl-7-( 2-hydroxyethyl)pyrazolo[1,5-a]pyridin-3-ylamine 12.15.1 3-Amino-7-(2-hydroxyethyl)-pyrazolo[1,5-a]pyridine 19.1 g. 2-hydroxyethylpyridine are dissolved in 50 ml. methylene chloride and mixed, while cooling with ice, with a solution of O-p-toluenesulphonylhydroxylamine which, according to the procedure give in the literature, is obtained by reacting 40 g. O-p-toluenesulphonylacethydroxamic acid ethyl ester with 300 ml. 60% perchloric acid.

The reaction mixture is stirred for 15 minutes in an ice-bath and for 1 hour at ambient temperature and then evaporated to dryness. The residue is dissolved in 40 ml. dimethylformamide and mixed with 28 g. potassium carbonate. 15 g. Ethyl propiolate are added dropwise thereto and, at the same time, air is passed into the reaction mixture. After a reaction period of 1 hour, the mixture is evaporated and chromatographed over silica gel with ligroin/ethyl acetate (1:1 v/v). There are obtained 10.8 g. of an oily, yellow-brown substance which is dissolved in 200 ml. concentrated hydrochloric acid and heated under reflux for 3 hours. The reaction mixture is rendered alkaline with an aqueous solution of sodium hydroxide while cooling with ice and the product is extracted with ethyl acetate. There are obtained 4.6 g. of a brown oil.

Analogously to Examples 4.4.1 and 4.4.2, there is obtained the title compound (12.15.1); m.p. 208° C. $R_f$=0.38 (silica gel, ethyl acetate/methanol 9:1 v/v).

12.15.2 Analogously to Example 4.3.2, by coupling with 2-chlorophenol there is obtained the coloured material which is acetylated on the hydroxyethyl radical by reaction with acetic anhydride in the presence of a catalytic amount of p-dimethylaminopyridine, reduced analogously to Examples 4.3.3 and trifluoroacetylated analogously to Example 10.5.

12.16  3-Chloro-4-hydroxphenyl-5-(2-hydroxethyl)pyrazolo[1,5-a]pyridin-3-ylamine Analogously to Example 12.15, there is obtained the N-trifluoroacetylated leuko coloured material starting from 4-hydroxyethylpyridine.

12.17 Analogously to Examples 4.3.2 and 4.3.3, the leuko coloured materials 2-methoxy-4-hydroxyphenylpyrazolo[1,5-a]pyridin-3-ylamine, 3-chloro-4-hydroxyphenylpyrazolo[1,5-a[pyridin-3-ylamine, 3-fluoro-4-hydroxyphenylpyrazolo[1,5-a]pyridin-3-ylamine and 2-methyl-4-hydroxyphenylpyrazolo[1,5-a]pyridin-3-ylamine are obtained by the oxidative coupling of 3-aminopyrazolo[1,5-a]pyridine (see Example 4.4.2) with the appropriately substituted phenols. The N-trifluoroacetylation is carried out analogously to Example 10.5.

12.18 4-Hydroxphenyl-4,6-dimethylpyrazolo[3,2-c]-s-triazol-3-ylamine 12.18.1 3-Amino-4,6-dimethylpyrazolo[3,2-c]-s-triazole hydrochloride General procedure for the synthesis of 3- or 5-amino-pyrazolo-4-carbonic acid derivatives:

In a 100 ml flask, to a mixture of 20 mmol of the nitrite component and 20 ml ethanol, the hydrazine (30 mmol 80% hydrazine hydrate resp. 20 mmol phenyl hydrazine in 5 ml ethanol) is added portion wise while stirring. The mixture is refluxed for one hour by heating on a water bath, is allowed to get cold; a sample is taken which is diluted with water. If the product is precipitating during rubbing, the whole reaction mixture is added while stirring into a double volume of water and is sucked off after 2 hours. If there is no precipitate, the mixture is concentrated on a water bath to dryness, the residue is rubbed well with a small volume of water which is then sucked off. After that, the product is crystallized.

24.4 g. Ethyl 3-aminopyrazole-4-carboxylate (see Organikum, p. 514, pub VEB Verlag der Wissenschaften, Berlin) are suspended in 100 ml. concentrated hydrochloric acid and diazotised at 0° to 5° C. by the addition of a solution of 10.35 g. sodium nitrite in 50 ml. water. Thereafter, there is added a solution of 100 g. stannous chloride in 100 ml. concentrated hydrochloric acid and the reaction mixture is further stirred for 2 hours in an ice-bath. The yellow precipitate obtained is filtered off, dissolved in 150 ml. water and mixed with 20 ml. acetic anhydride. The reaction mixture is heated to a bath temperature of 80° C. and mixed portionwise over the course of 2 hours with, in all, 25 g. sodium bicarbonate. The neutral solution is then continuously extracted with ethyl acetate for 24 hours. After drying and evaporating the organic phase, there are obtained 17 g. 3-acethydrazinopyrazole- 4-carboxylic acid ethyl ester ($R_f$=0.33; silica gel, acetone/methylene chloride/glacial acetic acid 50:45:5 v/v/v) which is cyclised with phosphorus oxychloride analogously to the procedure described in Example 6 of published Federal Republic of Germany Patent Specification No. 18 10 462. There are obtained 4.8 g. (32% of theory) 6-methylpyrazolo[3,2-c]s-triazole-3-carboxylic acid ethyl ester, $R_f$=0.70; silica gel, toluene/ethyl acetate/methanol 2:1:1 v/v/v).

The above-obtained heterocyclic compound is methylated analogously to Example 12.3.1 and the product is purified by chromatography over silica gel with ethyl acetate/ligroin (2:1 v/v). The ester is saponified by heating for 6 hours with 6N hydrochloric acid and the carboxylic acid formed as intermediate is decarboxylated. The acid is neutralised by the addition of sodium carbonate and the product is extracted with ethyl acetate. There is obtained 1.1 g. of oily 4,6-dimethylpyrazolo[3,2-c]-s-triazole. $R_f$=0.26; silica gel, ethyl acetate/ligroin 1:1 v/v).

The heterocyclic compound is nitrosated analogously to Example 4.4.1 and the nitroso group is reduced with palladium-carbon/hydrazine analogously to Example 5.1. The title compound (12.18.1) is obtained as hydrochloride; m.p. 190° C. (decomp.). $R_f$=0.53; silica gel, ethyl acetate/acetone/glacial acetic acid/water 50:25:12.5:12,5 v/v/v/v).

12.18.2 The amino compounds is coupled with phenol analogously to Example 4.3.2 to give the coloured material which is reduced according to Example 4.3.3 and N-trifluoroacetylated according to Example 10.5.

12.19 5-Bromo-2-methoxy-4-hydroxyphenyl-2-methoxypyrazolo[1,5-a]pyridin-361 -ylamine Starting from 2-bromo-5-methoxyphenol, the leuko coloured material is obtained analogously to Example 12.1.3.

12.20 3-Chloro-4-hydroxyphenyl-2-(2,3-dihydroxypropyl)-pyrazolo[1,5-a]-pyridin-3-ylamine The scheme for the synthesis of the starting material is as follows:

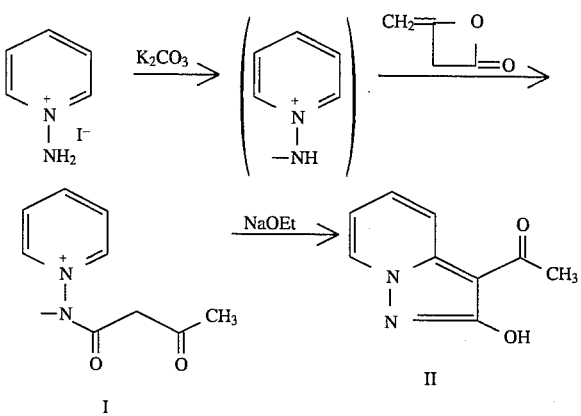

To prepare 3-acetyl-2-hydroxypyrazolo[1,5-a]pyridine (II)—To a solution of I (1.7 g) in abs. EtOH (20 ml), was added an NaOEt—EtOH solution prepared from Na (0.25 g) and abs. EtOH (10 ml). After stirring for 1 hr at room temperature, the solvent was distilled off under reduced pressure. The residue was diluted with $H_2O$ and neutralized with 10% HCl. The crystalline substance separated with collected by suction, and recrystallized from MeOH—AcOEt to give colorless needles, of mp 211°. Yield, 1.0 g (60%). Anal. Calcd. for $C_9H_8O_2N_2$ (II): C, 61.36; H, 4.58; N, 15.90. Found: C, 61.2;H, 4.96; N, 15.64. IR vcm$^{-1}$ 1638. NMR ($CF_3CO_2H$) ppm: 2.98 (3H, s) 7.48–8.90 (4H, m).

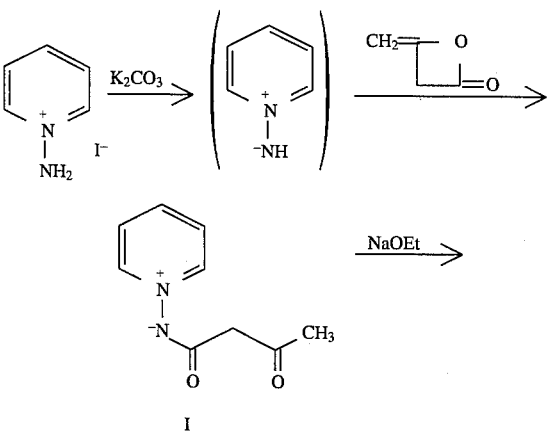

-continued

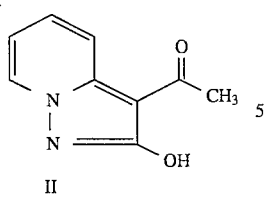

II

Synthesis of the starting material

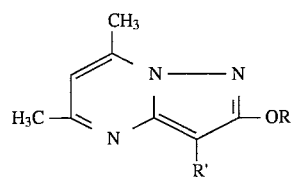

where $R=CH_3$ and $R'=H$ was effected wherein a suspension of

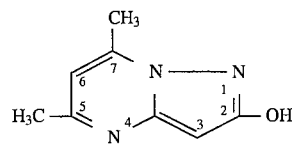

12.20.1 7 g. 3-Acetyl-2-hydroxypyrazolo[1,5-a]pyridine (see Chem. Pharm. Bull, 23, 452/1975) are O-alkylated analogously to Example 12.3.1 in dimethylformamide with 14.3 g. R,S-(2,2-dimethyl-1,3-dioxolan-4-yl)-methyl-p-toluene sulphonate and sodium hydride as base. The crude product is purified by chromatography over silica gel with ethyl acetate/ligroin as elution agent. There is obtained 1.47 g. 3-acetyl-2-(R,S-2,2-dimethyl-1,3-dioxolan-4-yl)methoxy)-pyrazolo[1,5-a]pyridine. $R_f$=0.45; silica gel, ethyl acetate/ligroin 1:1 v/v).

12.20.2 Analogously to Examples 4.3.1 and 4.3.2, from the above-obtained compound there is obtained the coloured material by coupling with 2-chlorophenol, whereby, in the case of the nitrostation, the ketal is cleaved and at the coloured material stage, the two free aliphatic hydroxyl groups are protected by means of acetic anhydride and p-dimethylaminopyridine as catalyst.

Analogously to Example 4.3.3, the coloured material is reduced to the leuko coloured material and N-trifluoroacetylated corresponding to Example 10.5. In the case of the splitting off after the glycosidation, the acetoxy radicals are also split off.

12.20.3 Analogously to Examples 12.20.1 to 12.20.2, the leuko coloured component is also obtained with 2,5-dichlorophenol.

12.21 4-Hydroxyphenyl-2-methoxy-5,7-dimethyl-pyrazolo[1,5-a]pyrimidin-3-ylamine indioxane is mixed while stirring and cooling with a solution of diazomethane (excess) in ether and it is continued to be stirred until the production of nitrogen stops.

After filtration, the solvent is evaporated and the crystalline residue is slowly crystallized in petroleum ether (60°–90°). White, rosette-like needles, mp. 95°–96°. Yield: 88% of theory $C_9H_{11}N_3O$ (177.2) Literature: C 61.00 H 6.76 N 23.71 Found: C 60.85 H 6.08 N 23.77

Analogously to Example 4.3.1, starting from 2-methoxy-5,7-dimethylpyrazolo[1,5-a]pyrimidine (see Anm. Chem., 647, 116/1961), where is obtained 3-amino-3,7-dimethyl-2-methoxypyrazolo[1,5-a]pyrimidine hydrochloride (m.p. 187°–190° C.) which is coupled with phenol analogously to Example 4.3.2 to give the coloured material which is reduced analogously to Example 4.3.3 and trifluoroacetylated analogously to Example 10.5.

EXAMPLE 13

Analogously to Example 11, there are obtained the compounds set out in the following Table 3:

TABLE 3

| No. | structure | m.p. °C. | $R_f$ | coloured material component, prepn. see |
|---|---|---|---|---|
| 13.1. | 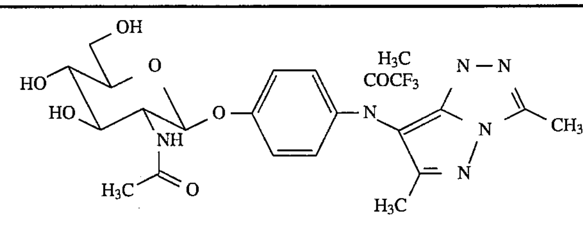 | 157 226 (decomp.) | 0.39[1] | Example 12.3 |
| 13.2. | 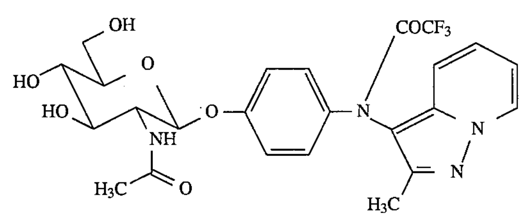 | 212–215 (decomp.) | 0.40[2] | Example 4.3 trifluoro-acetylation anaolmous to Example 10.5 |

EXAMPLE 14

4-(2-Methylpyrazolo[1,5-a]pyridin-3-ylamino)-phenyl-β-D-galactoside

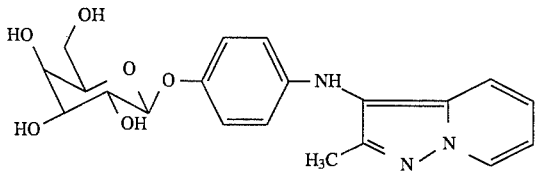

Analogously to Examples 1.2 and 1.3, with the use of the leuko coloured material obtained in Example 4.3 and 2,3,4,6-tetra-O-acetyl-α-D-galactosyl bromide, there is obtained the title compound; m.p. 137° C. $R_f$=0.5 (silica gel, toluene/ethyl acetate/methanol 1:1:1 v/v/v).

EXAMPLE 15

Test strips for the determination of leukocyte esterase (leukocyte test)

A filter paper of the firm Schleicher & Schüll (23 SL) is successively impregnated with the following solutions and dried:
1. borate buffer 50 mMole/liter, pH 8
2. indicator from Example 8 in methanol, 4 mMole/liter.

A mesh of nylon (NY 75 HC of the firm Züricher Beuteltuchfabrik, Zürich, Switzerland) with a filament thickness of 60 μm. is impregnated with a 50 mMole/liter potassium iodate solution and dried.

From the paper (1) impregnated with buffer and indicator, iodate fabric (2), covering mesh (3), also made of nylon (NY 75 HC) and a stiff plastic film (4), there is produced a test strip analogous to FIG. 5 of the accompanying drawings.

EXAMPLE 16

Determination of alkaline phosphatase a) Test strips

As described in Example 15, a filter paper of the firm Schleicher & Schüll (23 SL) is impregnated with:
1. hepes buffer, 50 mMole/liter, pH 7.5
2. indicator of Example 9 in methanol, 4 mMole/liter dried and covered by a mesh of iodate fabric produced as in Example 15.

Upon dipping such a test strips into an alkaline phosphatase solution, a coloration takes place from colourless to blue. An activity of 176 U/liter is to be detected by coloration after 5 minutes.

b) Wet chemical determination

Figure 6:
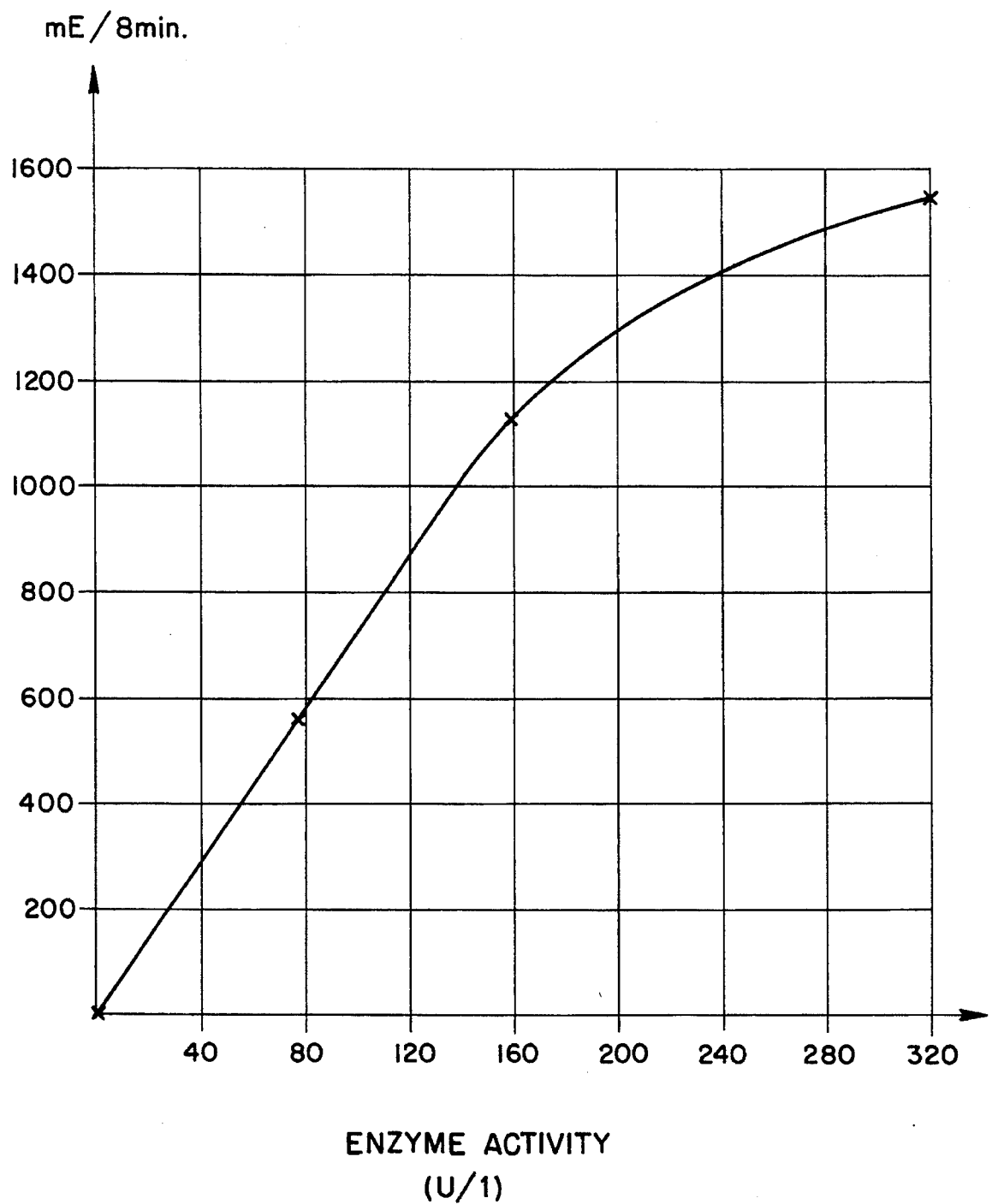
FIG. 6 is a calibration curve having known enzyme-containing solutions.

900 μl. of a solution of 4 mMole/liter of substrate from Example 9 in hepes buffer (50 mMole/liter) (pH 7.5) is taken. There is pipetted thereto:
1. 100 μl. of a 220 mMole/liter potassium iodate solution and
2. 100 μl. of an alkaline phosphatase-containing solution, mixed and the kinetics measured at a wavelength of 573 nm. A calibration curve according to FIG. 6 of the accompanying drawings can be prepared with known enzyme-containing solutions. In the case of this calibration curve, blank values have been deducted (corresponding process without enzyme).

EXAMPLE 17

Determination of β-D-galactosidase

Figure 7:
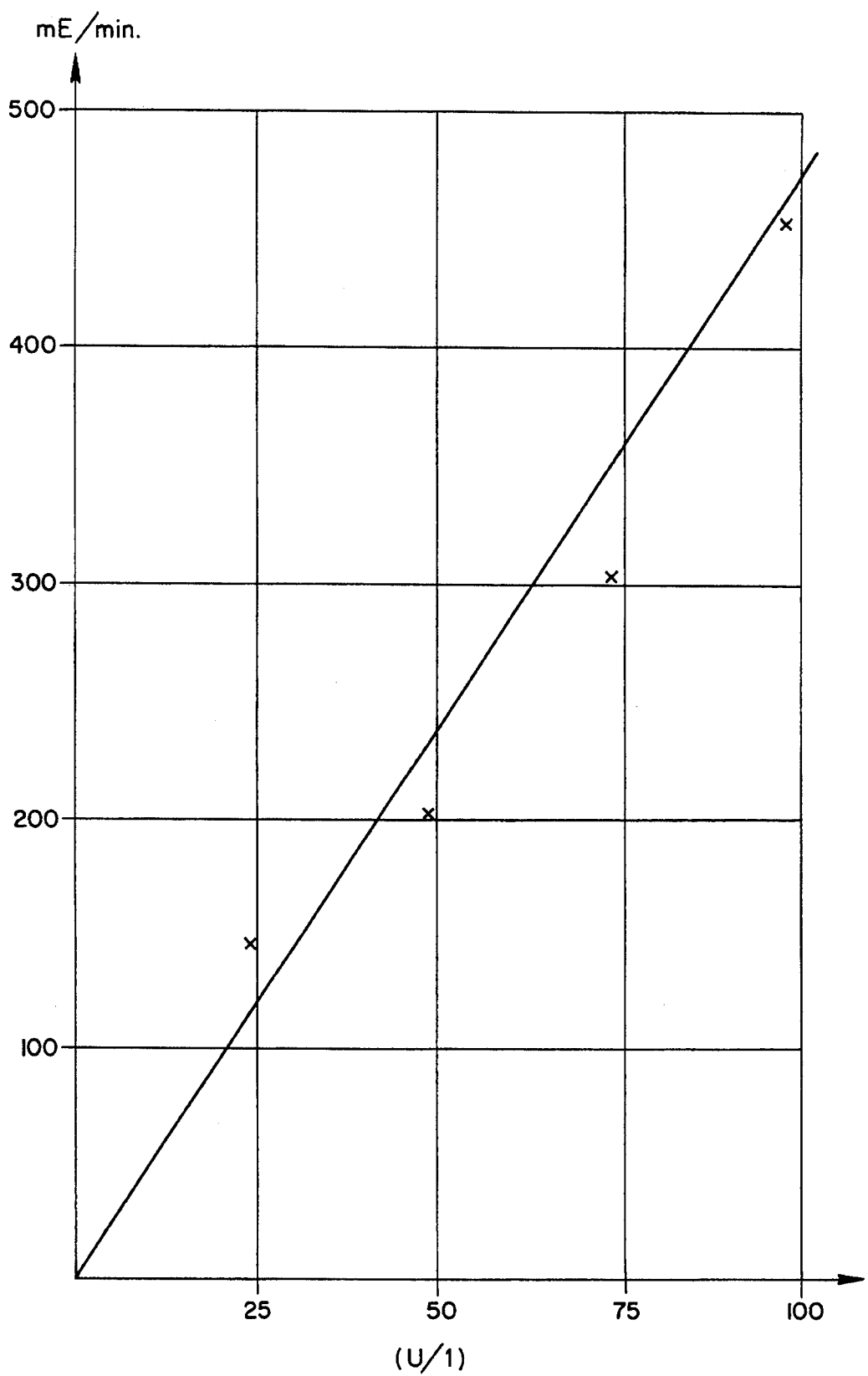
FIG. 7 is a calibration curve having known β-galactosidase-containing solutions.

900 μl. of a solution of 4 mMole/liter of substrate from Example 14 in 5C mMole/liter hepes buffer (pH 7.5) are placed in a cuvette and there are pipetted thereto:
1. 100 μl. of a 220 mMole/liter potassium iodate solution and
2. 100 μl. of a β-D-galctosidase-containing solution, mixed and the kinetics measured at a wavelength of 560 nm. A calibration curve according to FIG. 7 of the accompanying drawings can be obtained with known β-galctosidase-containing solutions.

EXAMPLE 18

Test strips for the determination of N-acetyl-β-D-glucosaminidase (NAGase)

A filter paper of the firm Schleicher & Schüll (23 SL) is successively impregnated with the following solutions and dried:
1. citrate buffer 200 mMole/liter, pH 5
2. indicator 10 mMole/liter and phenylsemicarbazide 4 mMole/liter in methanol.

A mesh of nylon (NY 75 HC of the firm Züricher Beuteltuchfabrk, Zürich, Switzerland) with a filament thickness of 60 μm. is impregnated with a 4 mMole/liter aqueous potassium iodate solution and dried.

From the paper (1) impregnated with buffer and indicator, iodate fabric (2), covering mesh (3) (also of nylon NY 75 HC) and a stiff plastic film (4), there is produced a test strip analogous to FIG. 5 of the accompanying drawings.

Upon dipping such a test strip into MAGase-containing solution (20 U/liter), a coloration of the strip takes place. In the following is shown which indicators give which colours:

| substrate of Example | coloration from | to |
|---|---|---|
| 12a | colourless | red |
| 12c | colourless | red |
| 12d | colourless | red |
| 12e | colourless | violet |
| 12g | colourless | red |
| 12h | colourless | red |
| 12i | colourless | red |
| 12j | colourless | red |
| 12k | colourless | blue-grey |
| 12l | colourless | red |
| 12m | colourless | orange |
| 12n | colourless | red |
| 12t | colourless | red |
| 12u | colourless | red |
| 12v | colourless | red |
| 12y | colourless | red |

It will be understood that the specification and examples are illustrative but not limitative of the present invention and that other embodiments within the spirit and scope of the invention will suggest themselves to those skilled in the art.

We claim:

1. An N- and O-substituted aminophenol derivative of formula:

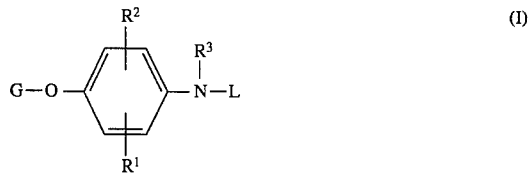

wherein

G is the residue of an organic or inorganic acid or a glycoside residue, $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighbouring carbon atoms, together represent a 1,4-butadiendiyl radical which is unsubstituted or substituted at least once by $SO_3H$, $PO_3H_2$ or a salt of the acid groups, an alkyl or a carboxyl group, $R^3$ is hydrogen, —CO—COOH, $SO_3H$, $SO_3H$, $PO_3H_2$ or a salt of the acid groups, an alkylcarbonyl radical unsubstituted or substituted at least once by halogen, COOH, $SO_3H$ or $PO_3H_2$ or a salt of the acid groups or an arylcarbonyl radical unsubstituted or substituted at least once by $SO_3H$, $PO_3H_2$ or a salt of the acid groups, and L is a pyrazolo-heterocylic radical of the general formula:

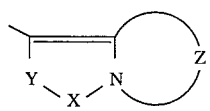

(III)

wherein

X-Y signifies $NR^8$—CO or $N=CR^9$, wherein $R^8$ is hydrogen or an alkyl and $R^9$ is alkyl, alkenyl, alkoxy, alkylthio, aryl, aralkyl, in each case substituted or substituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2N$—CO, alkyl, aralkyl- or arylcarbamoyl radicals; or $R^9$ hydrogen, carboxyl, alkoxycarbonyl, carboxamido or halogen, and Z signifies $NR^{10}$—N=N, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxylalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bone are unsubstituted or substituted by alkyl or aralkyl or two neighbouring chain substituents form an alkylene which, alkylene is unsubstituted or substituted or anellated with aryl and tautomers thereof, with the proviso that when G is an alkanecarboxylic acid radical, $R^3$ is hydrogen, an arylcarbonyl radical or an alkylcarbonyl radical unsubstituted or substituted at least once by halogen and L is pyrazolo-heterocyclic radical of formula (III), wherein X-Y signifies $N=CR^9$, whereby $R^9$ has the above-given meaning, Z does not form a 1,2,4-triazole ring in which a nitrogen atom not connected via a double bond is substituted with hydrogen.

2. The compound of claim 1 wherein G is a galactoside, glycoside, mannoside, N-acetylglucosaminide or an oligosaccharide radical consisting of 2 to 10 monosaccharide units.

3. The compounds of claim 1 wherein G is an N-acetyl-β-D-glucosaminidyl radical.

4. The compounds of claim 1 wherein G is $PO_3MM'$, $SO_3M$, a carboxyl-bound alkanecarboxylic acid, amino acid or oligopeptide residue and M and M' are hydrogen, alkali metal, alkaline earth metal or ammonium ions.

5. The compound of claim 1 wherein alkanecarboxylic acid residues of G are acetic, propionic, butyric, palmitic, stearic, oleic, linoleic or linolenic; and amino acid residue of G is glycine, alanine, valine, leucine, isoleucine, phenylalanine or tyrosine and a glycoside radical of G is β-glucosidically bound N-acetyl-2-D-glucosamine.

6. The compound of claim 1 wherein alkyl alone or combined is methyl, ethyl, propyl, isobutyl or tert.-butyl the twice-substituted amino is morpholino, hydroyalkyl is 2-hydroxyethyl, 1-hydroxyethyl or hydroxymethyl, aryl is phenyl, aralkyl is benzyl, aralkoxy is benzyloxy, alkenyl is vinyl or allyl, halogen is fluorine or chlorine, acyl is acetyl, phenylacetyl or benzoyl, alkylene is butadiendiyl, dialkylphosphinyl is dimethylphosphinyl and L is a pyrazoloheterocyclic radical of formula III wherein X-Y is $N—CR^9$ wherein $R^9$ is hydrogen or alkoxy.

7. The compound of claim 1 wherein L is from the group consisting of formulas (XIII) to XXIII and XXIV as follows:

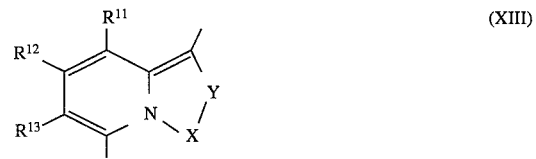

(XIII)

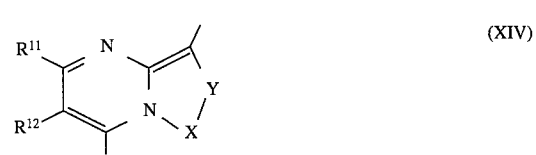

(XIV)

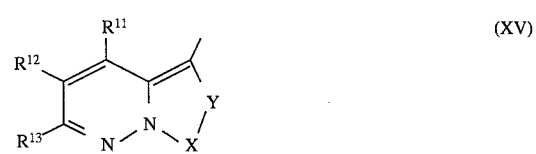

(XV)

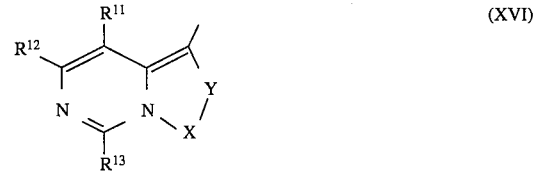

(XVI)

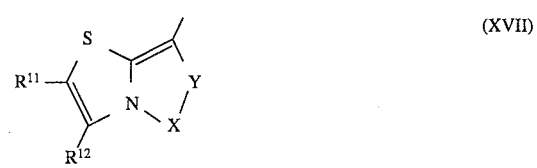

(XVII)

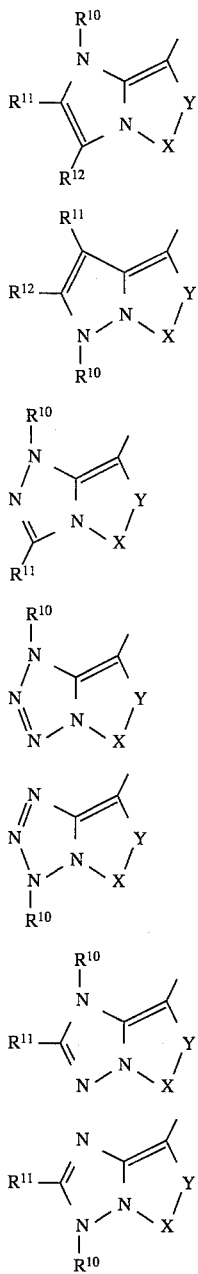

(XVIII)

(XIX)

(XX)

(XXI)

(XXII)

(XXIII)

(XXIV)

and tautomers thereof.

8. The compound of claim 1 wherein L is selected from the group consisting of formulas XIII, XIV, XV, XVII, XVIII, XX and tautomers thereof.

9. A compound of formula:

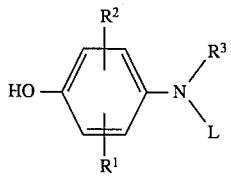

(V')

in which $R^1$–$R_3$ have the meanings given in claim 1 and L is a pyrazolo-heterocyclic radical of formula:

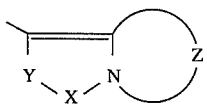

(III)

wherein X-Y and Z have the meanings given in claim 1, with the proviso that when $R^3$ is an arylcarbonyl radical or an alkylcarbonyl radical unsubstituted or substituted at least once by halogen and X-Y is C=$NR^9$, then Z does not form a 1,2,3-triazole ring in which a nitrogen atom not connected via a double bond is substituted with a hydrogen atom.

10. A compound of formula:

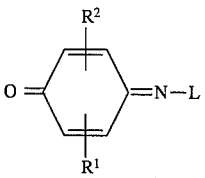

(VII)

wherein $R^1$ and $R^2$ have the meanings given in claim 1 and L is a pyrazolo-heterocyclic radical of the general formula

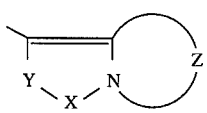

(III)

in which X-Y and Z have the meanings given in claim 1.

11. A method for the preparation of a compound of claim 1 or 2 comprising using a compound of claim 9 or 10.

12. A compound of claim 1 prepared by the process of claim 25.

13. A compound of claim 3 prepared by the process of claim 26.

14. The aminophenol derivative designated β-glucosidically-bound-N-acetyl-2-D-glucosaminide of 4-hydroxyphenyl-2-methylpyrazolo-[1,5-a]pyridine-3-ylamine or of 4-hydroxyphenyl-pyrazolo-[1,5-a]-pyridine-3-ylamine.

15. A diagnostic agent for determination of a hydrolase, comprising a chromogenic enzyme substrate and an appropriate buffer substance wherein the chromogenic substrate is a compound of the formula

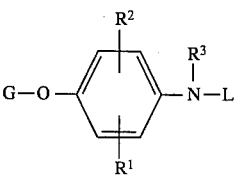

(I)

wherein

G is the residue of an organic or inorganic acid or a glycoside residue, $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighboring carbon atoms, together represent a 1,4-butadienydiyl radical which is unsubstituted or substituted at least once by $SO_3H$, $PO_3H_2$ or a salt of the acid groups, an alkyl or a carboxyl group, $R^3$ is hydrogen, —CO—COOH, $SO_3H$, $PO_3H_2$ or a salt of the acid groups, an alkylcarbonyl radical unsubstituted or substituted at least once by halogen, COOH, $SO_3H$ or $PO_3H_2$ or a salt of the acid groups or an arylcarbonyl radical unsubstituted or substituted at least once by $SO_3H$, $PO_3H_2$ or a salt of the acid groups, and L is a radical of the formula:

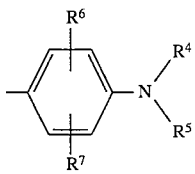 (II)

wherein $R^4$ and $R^5$, which are the same or different, are alkyl or together represent a saturated 3–6 member hydrocarbon chain which is uninterrupted or interrupted by oxygen, sulphur or nitrogen and wherein alkyl or the hydrocarbon chain is unsubstituted or substituted at least once by hydroxyl, carboxyl, alkoxycarbonyl, alkoxy, $SO_3H$ OR $PO_3H_2$, a salt of one of the acid groups or halogen, and $R^6$ and $R^7$, which can be the same or different, are hydrogen or halogen, hydroxyl or carboxamido or an alkyl, alkoxy, alkylcarbonyl, alkoxycarbonyl, aryl or aralkyl radical unsubstituted or substituted at least once by hydroxyl, carboxyl, halogen, $SO_3H$ or $PO_3H_2$ or a salt of one of the acid groups, or L is a pyrazol-heterocylic radical of the general formula:

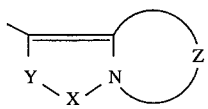 (III)

wherein

X-Y signifies $NR^8$—CO or N=$CR^9$, wherein $R^8$ is hydrogen or an alkyl and $R^9$ is alkyl, alkenyl, alkoxy, alkylthio, aryl, aralkyl, in each case unsubstituted or substituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2N$—CO, alkyl-, aralkyl- or arylcarbamoyl radicals; or $R^9$ hydrogen, carboxyl, alkoxycarbonyl, carboxamido or halogen, and Z signifies $NR^{10}$—N=N, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bond are unsubstituted or substituted by alkyl or aralkyl or two neighboring chain substituents form an alkylene which, alkylene is unsubstituted or substituted or anellated with aryl and tautomers thereof, with the proviso that when G is an alkanecarboxylic acid radical, $R^3$ is hydrogen, an arylcarbonyl radical or an alkylcarbonyl radical unsubstituted or substituted at least once by halogen and L is pyrazolo-heterocyclic radical of formula (III), wherein X-Y signifies N=$CR^9$, whereby $R^9$ has the above-given meaning, Z does not form a 1,2,4-triazole ring in which a nitrogen atom not connected via a double bond is substituted with hydrogen with the proviso that when G is alkanecarboxylic acid radical, $R^3$ is hydrogen, an alkylcarbonyl radical or an alkylcarbonyl radical unsubstituted or substituted at least once by halogen and L is a pyrazolo-heterocyclic radical of formula III wherein X-Y is N=$CR^9$, wherein $R^9$ has the meaning in claim 1 then Z can form a 1,2,4-triazole ring in which a nitrogen atom not connected by a double bond is substituted by hydrogen.

16. The diagnostic agent of claim 15, comprising an oxidizing agent.

17. The diagnostic agent of claim 15 further comprising an 1-arylsemicarbazide of the formula:

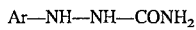

Ar—NH—NH—CONH$_2$ (XII)

wherein Ar is an aryl radical unsubstituted or substituted by alkyl, alkoxy or halogen.

18. The diagnostic agent of claim 17 designated o-methyl, p-methyl, o-methoxy, m-methoxy-, p-methoxy, o-chloro-m-chloro, m-methyl- and unsubstituted phenyl semicarbazides and naphthyl semicarbazide.

19. The diagnostic agent of claim 15 wherein the components are in carrier-bound form.

20. The diagnostic agent of claim 17 wherein the components are in carrier-bound form.

21. An N- and O-substituted aminophenol derivative of formula:

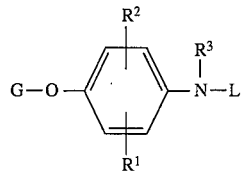 (I)

wherein

G is the residue of an organic or inorganic acid or a glycoside residue, $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighbouring carbon atoms, together represent a 1,4-butadiendiyl radical which is unsubstituted or substituted at least once by $SO_3H$, $PO_3H_2$ or a salt of the acid groups, an alkyl or a carboxyl group, $R^3$ is an alkylcarbonyl substituted at least once by halogen, and L is a radical of the formula:

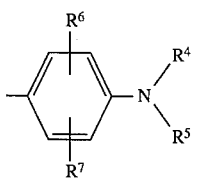

wherein $R^4$ and $R^5$, which are the same or different, are alkyl or together represent a saturated 3–6 member hydrocarbon chain which is uninterrupted or interrupted by oxygen, sulphur or nitrogen and wherein alkyl or the hydrocarbon chain is unsubstituted or substituted at least once by hydroxyl, carboxyl, alkoxycarbonyl, alkoxy, $SO_3H$ OR $PO_3H_2$, a salt of one of the acid groups or halogen, and $R^6$ and $R^7$, which can be the same or different, are hydrogen or halogen, hydroxyl or carboxamido or an alkyl, alkoxy, alkylcarbonyl, alkoxycarbonyl, aryl or aralkyl radical unsubstituted or substituted at least once by hydroxyl, carboxyl, halogen, $SO_3H$ or $PO_3H_2$ or a salt of one of the acid groups, or L is a pyrazolo-heterocylic radical of the general formula:

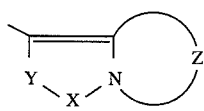

wherein

X–Y signifies $NR^8$—CO or N=$CR^9$, wherein $R^8$ is hydrogen or an alkyl and $R^9$ is alkyl, alkenyl, alkoxy, alkylthio, aryl, aralkyl, in each case unsubstituted or substituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2N$—CO, alkyl-, aralkyl- or arylcarbamoyl radicals; or $R^9$ hydrogen, carboxyl, alkoxycarbonyl, carboxamido or halogen, and Z signifies $NR^{10}$—N=N, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bone are unsubstituted or substituted by alkyl or aralkyl or two neighbouring chain substituents form an alkylene which, alkylene is unsubstituted or substituted or anellated with aryl and tautomers thereof, with the proviso that when G is an alkanecarboxylic acid radical, $R^3$ is hydrogen, an arylcarbonyl radical or an alkylcarbonyl radical unsubstituted or substituted at least once by halogen and L is pyrazolo-heterocyclic radical of formula (III), wherein X–Y signifies N=$CR^9$, wherein $R^9$ has the above-given meaning, Z does not form a 1,2,4-triazole ring in which a nitrogen atom not connected via a double bond is substituted with hydrogen.

22. An N- and O-substituted aminophenol derivative of formula:

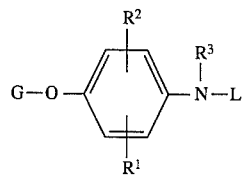

wherein

G is a glycoside residue or an inorganic acid residue, $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighbouring carbon atoms, together represent a 1,4-butadienyl radical which is unsubstituted or substituted at least once by $SO_3H$, $PO_3H_2$ or a salt of the acid groups, an alkyl or a carboxyl group, $R^3$ is hydrogen, —CO—COOH, $SO_3H$, $PO_3H_2$ or a salt of the acid groups, an alkylcarbonyl radical unsubstituted or substituted at least once by halogen, COOH, $SO_3H$ or $PO_3H_2$ or a salt of the acid groups or an arylcarbonyl radical unsubstituted or substituted at least once by $SO_3H$, $PO_3H_2$ or a salt of the acid groups, and L is a radical of the formula:

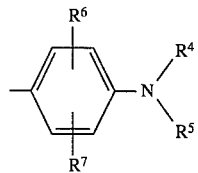

wherein $R^4$ and $R^5$, which are the same or different, are alkyl or together represent a saturated 3–6 member hydrocarbon chain which is uninterrupted or interrupted by oxygen, sulphur or nitrogen and wherein alkyl or the hydrocarbon chain is unsubstituted or substituted at least once by hydroxyl, carboxyl, alkoxycarbonyl, alkoxy, $SO_3H$ OR $PO_3H_2$, a salt of one of the acid groups or halogen, and $R^6$ and $R^7$, which can be the same or different, are hydrogen or halogen, hydroxyl or carboxamido or an alkyl, alkoxy, alkylcarbonyl, alkoxycarbonyl, aryl or aralkyl radical unsubstituted or substituted at least once by hydroxyl, carboxyl, halogen, $SO_3H$ or $PO_3H_2$ or a salt of one of the acid groups, or L is a pyrazolo-heterocylic radical of the general formula:

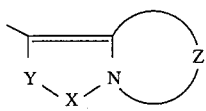
(III)

wherein

X-Y signifies $NR^8$—CO or N=$CR^9$, wherein $R^8$ is hydrogen or an alkyl and $R^9$ is alkyl, alkenyl, alkoxy, alkylthio, aryl, aralkyl, in each case unsubstituted or substituted by hydroxyl, dialkylphosphinyl, carboxyl $SO_3H$, $PO_3H_2$, a salt of one of the acid group or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2N$—CO, alkyl-, aralkyl- or arylcarbamoyl radicals; or $R^9$ hydrogen, carboxyl, alkoxycarbonyl, carboxamido or halogen, and Z signifies $NR^{10}$—N=N, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bone are unsubstituted or substituted by alkyl or aralkyl or two neighbouring chain substituents form an alkylene which, alkylene is unsubstituted or substituted or annellated with aryl and tautomers thereof, with the provisio that when G is an alkanecarboxylic acid radical, $R^3$ is hydrogen, an arylcarbonyl radical or an alkylcarbonyl radical unsubstituted or substituted at least once by halogen and L is pyrazolo-heterocyclic radical of formula (III), wherein X-Y signifies N=$CR^9$, whereby $R^9$ has the above-given meaning, Z does not form a 1,2,4-triazole ring in 23. The compound of claim 22 wherein G is a galactoside, glycoside, mannoside, N-acetylglucosaminide or an oligosaccharide radical consisting of 2 to 10 monosaccharide units.

24. The compounds of claim 22 wherein G is an N-acetyl-β-D-glucosamindyl radicals.

25. A process for the preparation of a compound of the formula wherein

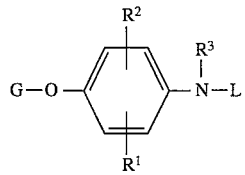
(I)

G is the residue of an organic or inorganic acid or a glycoside residue, $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighboring carbon atoms, together represent a 1,4-butadiendiyl radical which is unsubstituted or substituted at least once by $SO_3H$, $PO_3H_2$ or a salt of the acid groups, an alkyl or a carboxyl group, $R^3$ is hydrogen, —CO—COOH, $SO_3H$, $PO_3H_2$ or a salt of the acid groups, an alkylcarbonyl radical unsubstituted or substituted at least once by halogen, COOH, $SO_3H$ or $PO_3H_2$ or a salt of the acid groups or an arylcarbonyl radical unsubstituted or substituted at least once by $SO_3H$, $PO_3H_2$ or a salt of the acid groups, and L is a radical of the formula:

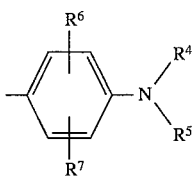
(II)

wherein $R^4$ and $R^5$, which are the same or different, are alkyl or together represent a saturated 3–6 member hydrocarbon chain which is uninterrupted or interrupted by oxygen, sulphur or nitrogen and wherein alkyl or the hydrocarbon chain is unsubstituted or substituted at least once by hydroxyl, carboxyl, alkoxycarbonyl, alkoxy, $SO_3H$ OR $PO_3H_2$, a salt of one of the acid groups or halogen, and $R^6$ and $R^7$, which can be the same or different, are hydrogen or halogen, hydroxyl or carboxamido or an alkyl, alkoxy, alkylcarbonyl, aryl or aralkyl radical unsubstituted or substituted at least once by hydroxyl, carboxyl, halogen, $SO_3H$ or $PO_3H_2$ or a salt of one of the acid groups, or L is a pyrazolo-heterocyclic radical of the general formula:

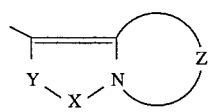
(III)

wherein

X-Y signifies $NR^8$—CO or N=$CR^9$, wherein $R^8$ is hydrogen or an alkyl and $R^9$ is alkyl, alkenyl, alkoxy, alkylthio, aryl, aralkyl, in each case unsubstituted or unsubstituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radical can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2N$—CO, alkyl-, aralkyl- or arylcarbamoyl radicals; or $R^9$ hydrogen, carboxyl, alkoxycarbonyl, carboxamido or halogen, and Z signifies $NR^{10}$—N=N, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bond are unsubstituted or substituted by alkyl or aralkyl or two neighboring chain substituents form an alkylene which, alkylene is unsubstituted or substituted or anellated with aryl and tautomers thereof, with the proviso that when G is an alkanecarboxylic acid radical, $R^3$ is hydrogen, an arylcarbonyl radical or an alkylcarbonyl radical unsubstituted or substituted at least once by halogen and L is pyrazolo-heterocyclic radical of formula (III), wherein X-Y signifies $N=CR^9$, whereby $R^9$ has the above-given meaning, Z does not form a 1,2,4-triazole ring in which a nitrogen atom not connected via a double bond is substituted with hydrogen, comprising reacting a compound of formula:

G—D  (IV)

wherein G is the residue of an organic or inorganic acid or a glycoside residue and D is a reactive group and wherein any functional groups of G are unprotected or protected with protective groups of peptide carbohydrate chemistry with a compound of the formula:

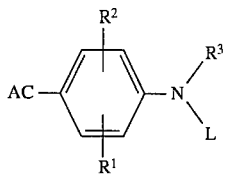

(V)

26. The process of claim 25 further comprising for the preparation of a compound wherein G is an N-acetyl-β-D glucosaminidyl radical reacting as a compound of formula (IV), a compound of formula:

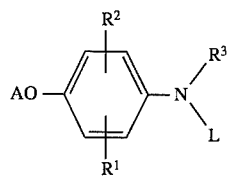

(VI)

wherein W is halogen, R is a hydroxyl protective group conventional in carbohydrate chemistry and B is an azide group, a protected amino group or NH—$COCH_3$ or B and W together form the group:

with a compound of formula:

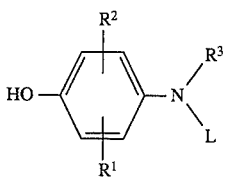

(V)

in which $R^1$–$R^3$, L and A have the meanings given above, and removing the amino protective group when B is a protected amino group or converting azide to amino when B is an azide by reduction into an amino group and converting the amino group by acetylation into an —$NHCOCH_3$ radical and removing subsequently the hydroxyl protective groups.

27. A process for the preparation of a compound of the formula

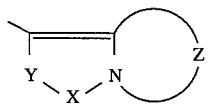

(V')

in which $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighboring carbon atoms, together represent a 1,4-butadiendiyl radical which is unsubstituted or substituted at least once by $SO_3H$, $PO_3H_2$ or a salt of the acid groups, an alkyl or a carboxyl group, $R^3$ is hydrogen, —CO—COOH, $SO_3H$, $PO_3H_2$ or a salt of the acid groups, an alkylcarbonyl radical unsubstituted or substituted at least once by halogen, COOH, $SO_3H$ or $PO_3H_2$ or a salt of the acid groups or an arylcarbonyl radical unsubstituted or substituted at least once by $SO_3H$, $PO_3H_2$ or a salt of the acid groups, and L is a pyrazolo-heterocyclic radical of formula:

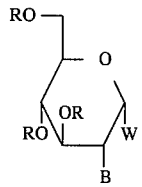

(III)

wherein X-Y signifies $NR^8$—CO or $N=CR^9$, wherein $R^8$ is hydrogen or an alkyl and $R^9$ is alkyl, alkenyl, alkoxy, alkylthio, aryl, aralkyl, in each case unsubstituted or substituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, H$_2$N—CO, alkyl-, aralkyl- or arylcarbamoyl radicals; or R$^9$ hydrogen, carboxyl, alkoxycarbonyl, carboxamido or halogen, and Z signifies NR$^{10}$—N=N, wherein R$^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bond are unsubstituted or substituted by alkyl or aralkyl or two neighboring chain substituents form an alkylene which, alkylene is unsubstituted or substituted or anellated with aryl and tautomers thereof, with the proviso that when R$^3$ is an arylcarbonyl radical or an alkylcarbonyl radical unsubstituted or substituted at least once by halogen and X-Y is C=NR$^9$, then Z does not form a 1,2,3-triazole ring in which a nitrogen atom not connected via a double bond is substituted with a hydrogen atom comprising reducing a compound of formula:

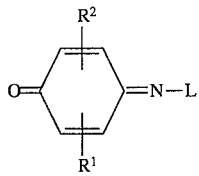
(VII)

in which R$^1$, R$^2$ and L have the meanings given above, and, when R$^3$ is not hydrogen, acylating the anilino group and subsequently cleaving any ester bond present, or reacting a compound of claim 1, in which L is a pyrazolo-heterocyclic radical of formula:

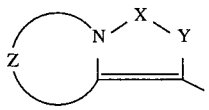
(III)

in which X-Y have the meanings given above and G is the residue of an organic or inorganic or a glycoside residue, with an appropriate hydrolase.

28. A process for the preparation of a compound of the formula

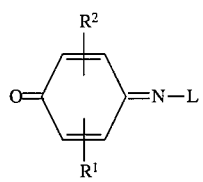
(VII)

wherein R$^1$ and R$^2$, which are the same or different, are hydrogen or halogen, SO$_3$H, PO$_3$H$_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, SO$_3$H or PO$_3$H$_2$ or a salt of one of the acid residues or, when two substituents of R$^1$ and R$^2$ are present on neighboring carbon atoms, together represent a 1,4-butadiendiyl radical which is unsubstituted or substituted at least once by SO$_3$H, PO$_3$H$_2$ or a salt of the acid groups, an alkyl or a carboxyl group, comprising reacting a compound of the formula

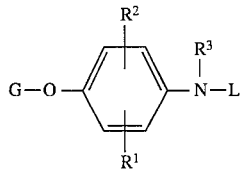
(I)

wherein

G is the residue of an organic or inorganic acid or a glycoside residue, L is a pyrazolo-heterocyclic radical of formula:

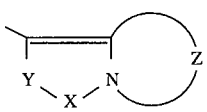
(III)

in which X-Y signifies NR$^8$—CO or N=CR$^9$, wherein R$^8$ is hydrogen or an alkyl and R$^9$ is alkyl, alkenyl, alkoxy, alkylthio, aryl, aralkyl, in each case unsubstituted or substituted by hydroxyl, dialkylphosphinyl, carboxyl SO$_3$H, PO$_3$H$_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, H$_2$N—CO, alkyl-, aralkyl- or arylcarbamoyl radicals; or R$^9$ hydrogen, carboxyl, alkoxycarbonyl, carboxamido or halogen, and Z signifies NR$^{10}$—N=N, wherein R$^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bond are unsubstituted or substituted by alkyl or aralkyl or two neighboring chain substituents form an alkylene which, alkylene is unsubstituted or substituted or annellated with aryl and tautomers thereof, with a hydrolase and oxidizing the reaction product to produce the compound of the formula (VII).

29. A process for the preparation of a compound of the formula

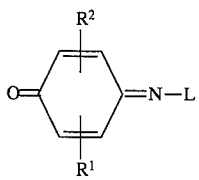 (VII)

wherein $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighboring carbon atoms, together represent a 1,4-butadiendiyl radical which is unsubstituted or substituted at least once by $SO_3H$, $PO_3H_2$ or a salt of the acid groups, an alkyl or a carboxyl group, comprising reacting a compound of formula:

 (VIII)

wherein L is a pyrazolo-heterocyclic radical of formula:

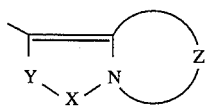 (III)

X-Y signifies $NR^8$—CO or $N=CR^9$, wherein $R^8$ is hydrogen or an alkyl and $R^9$ is alkyl, alkenyl, alkoxy, alkylthio, aryl, aralkyl, in each case unsubstituted or substituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2N$—CO, alkyl-, aralkyl- or arylcarbamoyl radicals; or $R^9$ hydrogen, carboxyl, alkoxycarbonyl, carboxamido or halogen, and Z signifies $NR^{10}$—$N=N$, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bond are unsubstituted or substituted by alkyl or aralkyl or two neighboring chain substituents form an alkylene which, alkylene is unsubstituted or substituted or anellated with aryl and tautomers thereof, with a phenol of formula:

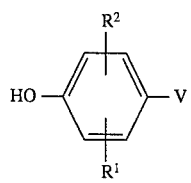 (IX)

wherein $R^1$ and $R^2$ have the meanings given above and V is a hydrogen or halogen atom or a COOH or $SO_3H$ group, in the presence of an oxidation agent.

30. A process for the preparation of a compound of the formula

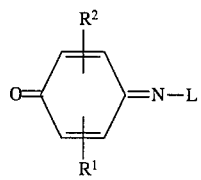 (VII)

wherein $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one acid residues or, when two substituents of $R^1$ and $R^2$ are present on neighboring carbon atoms, together represent a 1,4-butadienyl radical which is unsubstituted or substituted at least once by $SO_3H$, $PO_3H_2$ or a salt of the acid groups, an alkyl or a carboxyl group, comprising reacting a compound of formula:

 (X)

in which L is a pyrazolo-heterocyclic radical of formula:

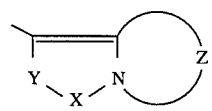 (III)

wherein X-Y signifies $NR^8$—CO or $N=CR^9$, wherein $R^8$ is hydrogen or an alkyl and $R^9$ is alkyl, alkenyl, alkoxy, alkylthio, aryl, aralkyl, in each case unsubstituted or substituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2N$—CO, alkyl-, aralkyl- or arylcarbamoyl radicals; or $R^9$ hydrogen, carboxyl, alkoxycarbonyl, carboxamido or halogen, and Z signifies $NR^{10}$—$N=N$, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bond are unsubstituted or substituted by alkyl or aralkyl or two neighboring chain substituents form an alkylene which, alkylene is unsubstituted or substituted or anellated with aryl and tautomers thereof, with a compound of formula:

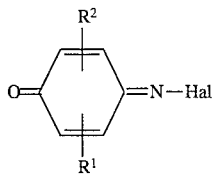  (XI)

wherein $R^1$ and $R^2$ have the meanings given above and Hal is halogen.

31. A process for the preparation of a compound of the formula

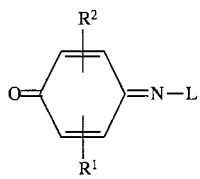  (VII)

wherein $R^1$ and $R^2$, which are the same or different, are hydrogen or halogen, $SO_3H$, $PO_3H_2$ or a salt of the acid residues, hydroxyl, nitro, carboxyl, carboxamido or cyano or alkyl, alkenyl, alkoxy, alkylsulphinyl, alkylsulphonyl, alkoxycarbonyl, alkylcarbonyl, aryl or aralkyl unsubstituted or substituted at least once by hydroxyl, carboxyl, halogen, cyano, $SO_3H$ or $PO_3H_2$ or a salt of one of the acid residues or, when two substituents of $R^1$ and $R^2$ are present on neighboring carbon atoms, together represent a 1,4-butadiendiyl radical which is unsubstituted or unsubstituted at least once by $SO_3H$, $PO_3H_2$ or a salt of the acid groups, an alkyl or a carboxyl group, comprising reacting a compound of formula:

L—E  (XXV)

wherein E is a nitro or nitroso group and L is a pyrazoloheterocyclic radical of formula:

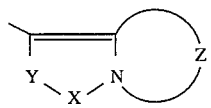  (III)

wherein X-Y signifies $NR^8$—CO or N=$CR^9$, wherein $R^8$ is hydrogen or an alkyl and $R^9$ is alkyl, alkenyl, alkoxy, alkylthio, aryl, aralkyl, in each case unsubstituted or substituted by hydroxyl, dialkylphosphinyl, carboxyl $SO_3H$, $PO_3H_2$, a salt of one of the acid groups or alkoxycarbonyl; amino, which is unsubstituted or substituted by one or two alkyl radicals which alkyls are unsubstituted or substituted by at least one hydroxyl, carboxyl or alkoxycarbonyl radical and wherein when amino is substituted by two alkyl radicals, the alkyl radicals can be joined to form a ring which, apart from the first nitrogen atom of the amino group, is uninterrupted or is interrupted by oxygen, sulphur or a second nitrogen atom, or amino is unsubstituted or substituted by one or two acyl radicals, alkoxy- or aralkoxycarbonyl radicals, $H_2H$—CO, alkyl-, aralkyl- or arylcarbamoyl radicals; or $R^9$ hydrogen, carboxyl, alkoxycarbonyl, carboxamido or halogen, and Z signifies $NR^{10}$—N=N, wherein $R^{10}$ is hydrogen or an alkyl or aralkyl radical, or Z is an unsaturated 3–5 member chain of nitrogen atoms or of carbon atoms, or said chain having at least one nitrogen or sulphur atom, whereby carbon atoms in the chain are unsubstituted or substituted by alkyl, alkoxy, hydroxyalkyl, alkylthio, hydroxyl, aralkyl, aryl, carboxyl, carboxamido, alkoxycarbonyl, cyano, amino, which is unsubstituted or substituted by one or two alkyl radicals which alkyl is unsubstituted or substituted by at least one hydroxyl, carboxyl or alkoxycarbonyl radicals or halogen, as well as nitrogen which are not attached via a double bond are unsubstituted or substituted by alkyl or aralkyl or two neighboring chain substituents form an alkylene which, alkylene is unsubstituted or substituted or anellated with aryl and tautomers thereof, with an organo-metallic compound of formula:

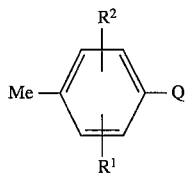  (XXVI)

wherein $R^1$ and $R^2$ have the meanings given above, Q is a hydroxyl group or a dialkylamino radical and Me is a lithium atom or a magnesium atom substituted by halogen and subsequently working up in an aqueous medium.

* * * * *

UNITED STATES PATENT AND TRADEMARK OFFICE
CERTIFICATE OF CORRECTION

PATENT NO. : 5,525,480
DATED : June 11, 1996
INVENTOR(S) : Zimmermann et al.

It is certified that error appears in the above-indentified patent and that said Letters Patent is hereby corrected as shown below:

In column 32, line 8 of the Patent, after "mixture" insert
--is poured into 100ml. 2N acetic acid. The tetrahydrofuran
is stripped off on a rotary evaporator. The reaction mixture--

In column 54, line 27 of the Patent, after "5" insert -- % --.

Signed and Sealed this

Twelfth Day of May, 1998

Attest:

BRUCE LEHMAN

Attesting Officer

Commissioner of Patents and Trademarks